(12) United States Patent
Young et al.

(10) Patent No.: US 7,262,336 B2
(45) Date of Patent: Aug. 28, 2007

(54) TRANSGENIC ANIMAL

(75) Inventors: Kathleen Young, Newtown, PA (US);
David S. Howland, Yardley, PA (US);
Karen L. Marquis, Yardley, PA (US);
Sharon Rosenzweig-Lipson, East Brunswick, NJ (US); Mark Ian Cockett, Newtown, PA (US)

(73) Assignee: Wyeth, Madison, NJ (US)

( * ) Notice: Subject to any disclaimer, the term of this patent is extended or adjusted under 35 U.S.C. 154(b) by 373 days.

(21) Appl. No.: 10/258,561

(22) PCT Filed: Apr. 24, 2001

(86) PCT No.: PCT/US01/13162

§ 371 (c)(1),
(2), (4) Date: Oct. 24, 2002

(87) PCT Pub. No.: WO01/84921

PCT Pub. Date: Nov. 15, 2001

(65) Prior Publication Data

US 2004/0025197 A1    Feb. 5, 2004

Related U.S. Application Data

(60) Provisional application No. 60/245,473, filed on Nov. 3, 2000, provisional application No. 60/199,209, filed on Apr. 24, 2000.

(51) Int. Cl.
*G01N 33/00* (2006.01)
*A01K 67/027* (2006.01)
*C12N 15/00* (2006.01)

(52) U.S. Cl. .............. 800/14; 800/3; 800/21

(58) Field of Classification Search ............ 800/3, 800/14, 21
See application file for complete search history.

(56) References Cited

FOREIGN PATENT DOCUMENTS

| WO | 97/36477 | 10/1997 |
|---|---|---|
| WO | 97/48820 | 12/1997 |
| WO | 99/18211 | 4/1999 |
| WO | 00/12704 | 3/2000 |

OTHER PUBLICATIONS

Sigmund, C.D. 2000. Arterioscler Thromb Vasc Biol.20:1425-1429.*
Jacks et al. 1992, Nature, vol. 359, pp. 295-300.*
Wall. Transgenic Livestock: Progress and Prospects for the Future. 1996. Theriogenology. vol. 45, pp. 57-68.*
Grafstein-Dunn et al., *Mol. Brain Res.* 88:113-123, 2001.
Hepler, *Trends in Pharm. Sci.* 20:376-382, Sep. 1999.
Tesmer et al., *Science* 278:1907-16, Dec. 1997.
DiBello et al. "Selective Uncoupling of RGS Action by a Single Point Mutation in the G Protein α-Subunit" The Journal of Biological Chemistry, vol. 273, No. 10, pp. 5780-5784 (1998).
Lan et al. "A Point Mutation of $G\alpha_o$ and $G\alpha_{i1}$ Blocks Interaction with Regulator of G Protein Signaling Proteins" The Journal of Biological Chemistry, vol. 273, No. 21 pp. 12794-12797 (1998).
P. Caroni, "Overexpression of Growth-Associated Proteins in the Neurons of Adult Transgenic Mice" J Neurosci Methods, vol. 71, No. 1, Jan. 1997, pp. 3-9.
P. R. DiBello et al., "Selective Uncoupling of RGS Action by Single Point Mutation in the G Protein α-subunit" Journal of Biological Chemistry, vol. 273, No. 10, Mar. 6, 1998, pp. 5780-5784.
D. J. Shuey et al., "RGS7 Attenuates Signal Transduction Through the $G\alpha_q$ Family of Heterotrimeric G Proteins in Mammalian Cells" J Neurochem, vol. 70, No. 5, May 1998, pp. 1964-1972.
A. Gilchrist et al., "A Dominant-Negative Strategy for Studying Roles of G Proteins in Vivo" Journal of Biological Chemistry, vol. 274, No. 10, Mar. 5, 1999, pp. 1964-1972.
D. Holland et al., "Transgenic Expression of an RGS-Resistant GOα Mutant (G188S) in Rat Brain" Society for Neuroscience Abstracts, vol. 26, No. 1-2, Nov. 4, 2002, entire page.

* cited by examiner

*Primary Examiner*—Celine Qian
(74) *Attorney, Agent, or Firm*—Fish & Richardson P.C.

(57) ABSTRACT

A transgenic rat containing in its genome a nucleotide sequence encoding a Ga subunit protein, which Ga protein subunit is uncoupled from regulation by Regulators of G-Protein Signaling (RGS) proteins, which Gx subunit protein is eventually the dominant-negative G188S mutant of Gax9, which nucleotide sequence is operatively associated with a neuron-specific expression control sequence, wherein the transgenic rat expresses the GA subunit protein in neural cells resulting in extended D-protein coupled receptor signaling mediated by the Ga subunit protein.

24 Claims, 41 Drawing Sheets

FIG. IA

```
     XhoI
     ctcgagccaccatgactctggagtccatcatggcgtgctgcctgagcgaggaggccaagg    60
   1 ---------+---------+---------+---------+---------+---------+
               M  T  L  E  S  I  M  A  C  C  L  S  E  E  A  K  E aagcccggaggatcaacgacgagatcgagcggcacgtgcgcagggacaagcgcgacgccc   120
  61 ---------+---------+---------+---------+---------+---------+
       A  R  R  I  N  D  E  I  E  R  H  V  R  R  D  K  R  D  A  R gccgggagctcaagctgctgctgggacaggggagagtggcaagagcaccttcatca       180
 121 ---------+---------+---------+---------+---------+---------+
       R  E  L  K  L  L  L  G  T  G  E  S  G  K  S  T  F  I  K agcagatgaggatcatccacgggtcgggctactctgacgaagacaagcgcggcttcacca   240
 181 ---------+---------+---------+---------+---------+---------+
       Q  M  R  I  I  H  G  S  G  Y  S  D  E  D  K  R  G  F  T  K agctggtgtatcagaacatcttcacggccatgcaggcaatgatcagagcgatggacacgc   300
 241 ---------+---------+---------+---------+---------+---------+
       L  V  Y  Q  N  I  F  T  A  M  Q  A  M  I  R  A  M  D  T  L tcaagatcccatacaagtatgaacacaataaggctcatgcacattggttcgagaggttg   360
 301 ---------+---------+---------+---------+---------+---------+
       K  I  P  Y  K  Y  E  H  N  K  A  H  A  Q  L  V  R  E  V  D atgtggagaaggtgtctgctttgagaatccatatgtagatgcaataaagagcttgtgga   420
 361 ---------+---------+---------+---------+---------+---------+
       V  E  K  V  S  A  F  E  N  P  Y  V  D  A  I  K  S  L  W  N atgatcctggaatccaggagtgtacgacgacgggaatatcagttatctgactcta      480
 421 ---------+---------+---------+---------+---------+---------+
       D  P  G  I  Q  E  C  Y  D  R  R  R  E  Y  Q  L  S  D  S  T
```

FIG. 1B

```
481  ccaaatactatctgaatgacttggaccgtgtagccgaccctgatacatgccgacagagc
      K  Y  L  N  D  L  D  R  V  A  D  P  E  Y  M  P  T  E  Q
                          D  V  L  R  V  R  V  P  T  T  S  I  I  E  Y  P  F  D  L  Q
541  aagacgtgcttagagttcggggtacccactacaagcatcatcgaataccctttgacttac                                                           600

601  aaagtgtcatttcagaatggtcgatgtagggggccaaaggtcagagagaagaaatgga                                                              660
      S  V  I  F  R  M  V  D  V  G  G  Q  R  S  E  R  R  K  W  I 661  tacactgctttgaaaatgtcacctccatcatgtttctagtagcgcttagcgaatatgatc                                                           720
      H  C  F  E  N  V  T  S  I  M  F  L  V  A  L  S  E  Y  D  Q 721  aagttcttgtggagtcagacaatgagaaccgcatggaggagcaaagcactctttagaa                                                              780
      V  L  V  E  S  D  N  E  N  R  M  E  E  S  K  A  L  F  R  T 781  caattatcacctacccctggttccagaactcctctgtgttcttaaacaagaaag                                                                  840
      I  I  T  Y  P  W  F  Q  N  S  S  V  I  L  F  L  N  K  K  D 841  atctttctagaggagaaaatcatgtattccaccagtcgactacttcccagaatatgatg                                                             900
      L  E  E  K  I  M  Y  S  H  L  V  D  Y  F  P  E  Y  D  G 901  gacccagagatgcccaggcagccgagaattcatcctgaaaatgttcgtgtggacctga                                                              960
      P  Q  R  D  A  Q  A  A  R  E  F  I  L  K  M  F  V  D  L  N
```

FIG. IC

```
 961 accccgacagtgacaaaatcatctactcccacttcacgtgcgccacagataccgagaaca
      ----+----|----+----|----+----|----+----|----+----|----+---- 1020
      P  D  S  D  K  I  I  Y  S  H  F  T  C  A  T  D  T  E  N  I 1021 tccgcttcgtctttgcagccgtcaaggacaccatcctgcagctgaacctgaaggagtaca
      ----+----|----+----|----+----|----+----|----+----|----+---- 1080
      R  F  V  F  A  A  V  K  D  T  I  L  Q  L  N  L  K  E  Y  N
                           XhoI
1081 atctggtctaactcgag
      ----+----|------ 1097
      I  W  S  *
```

FIG. 2
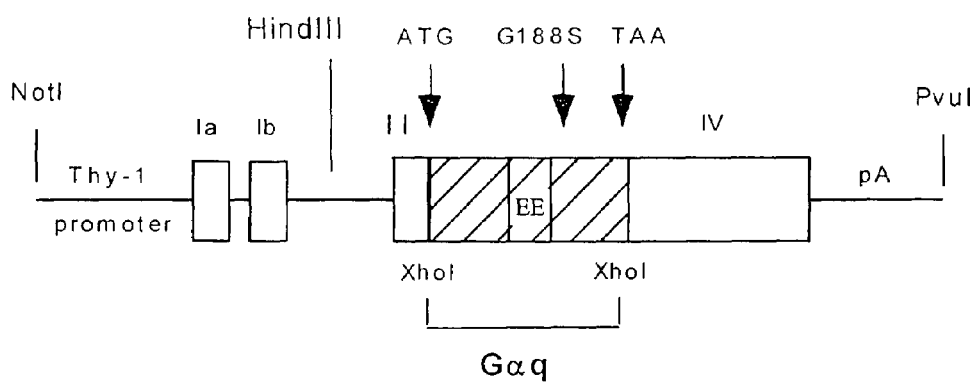
FIG. 5
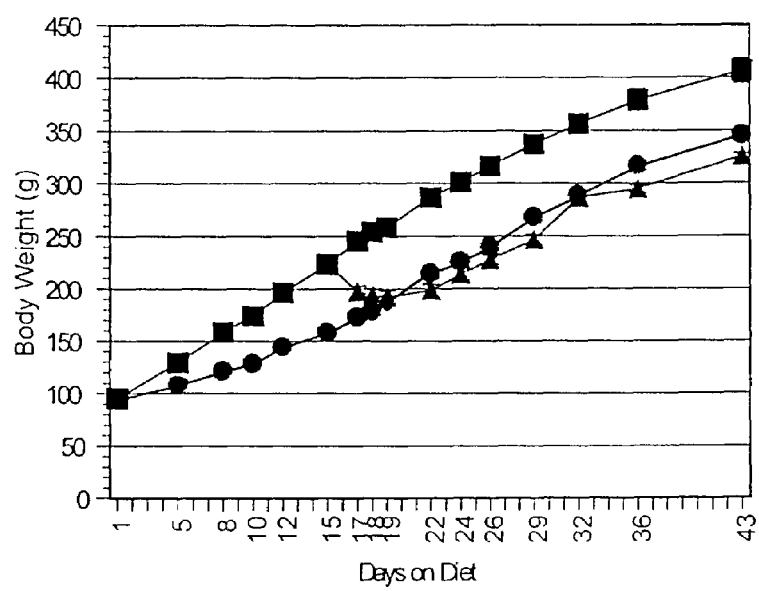
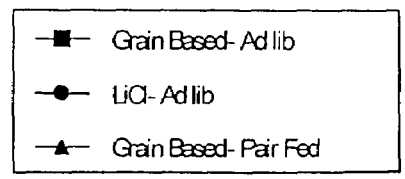

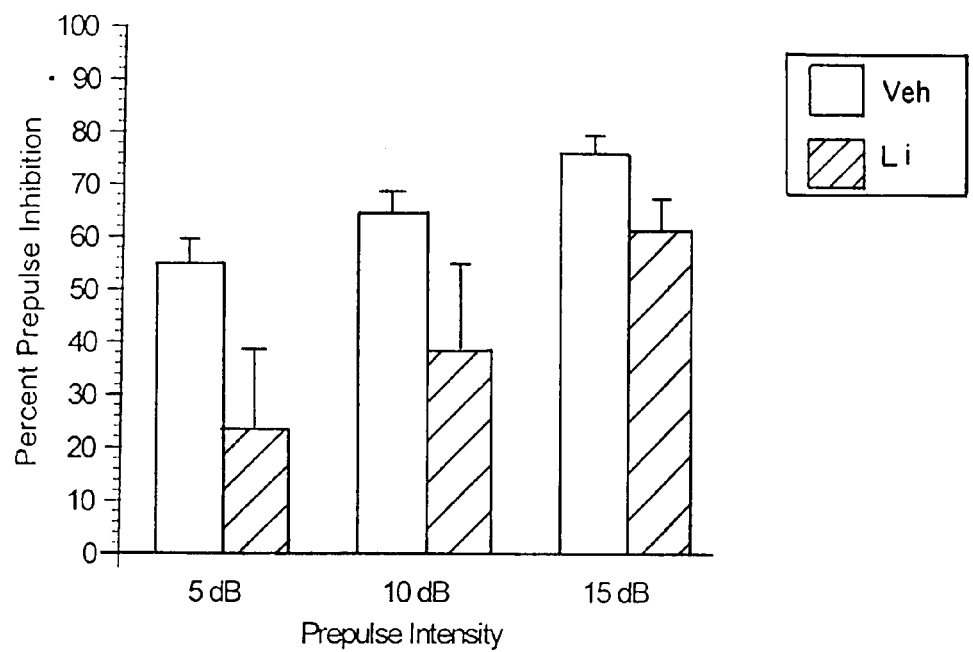
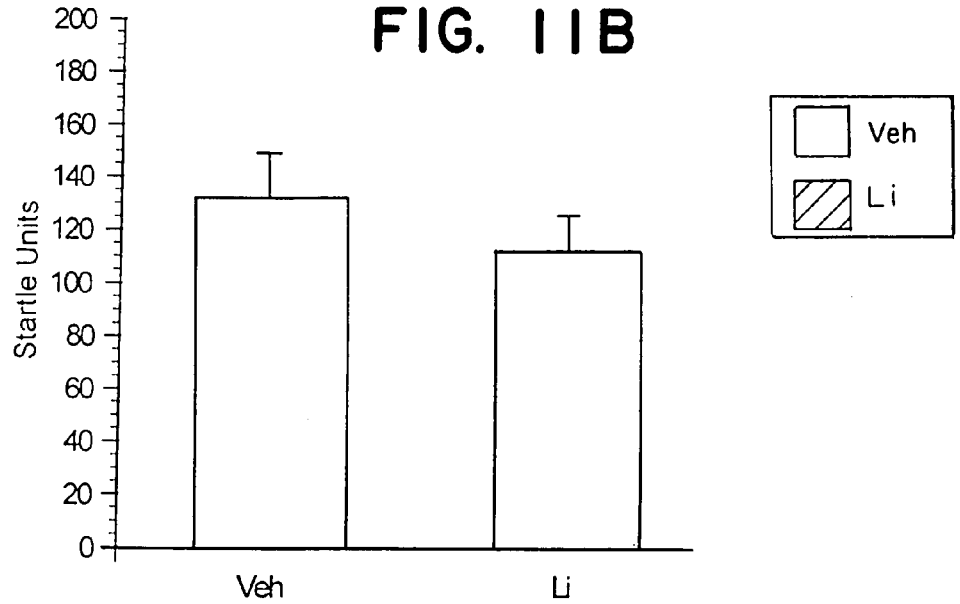

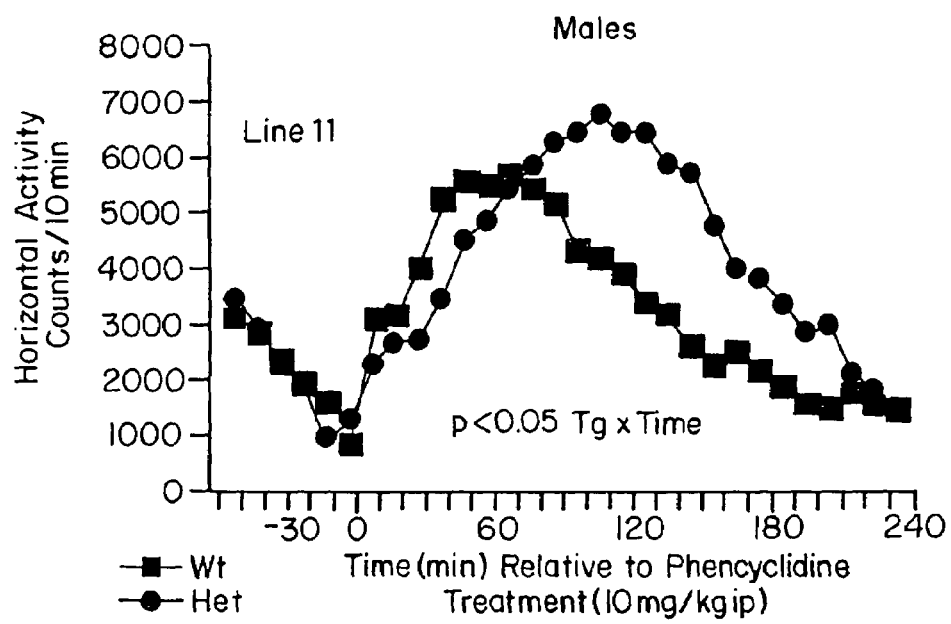
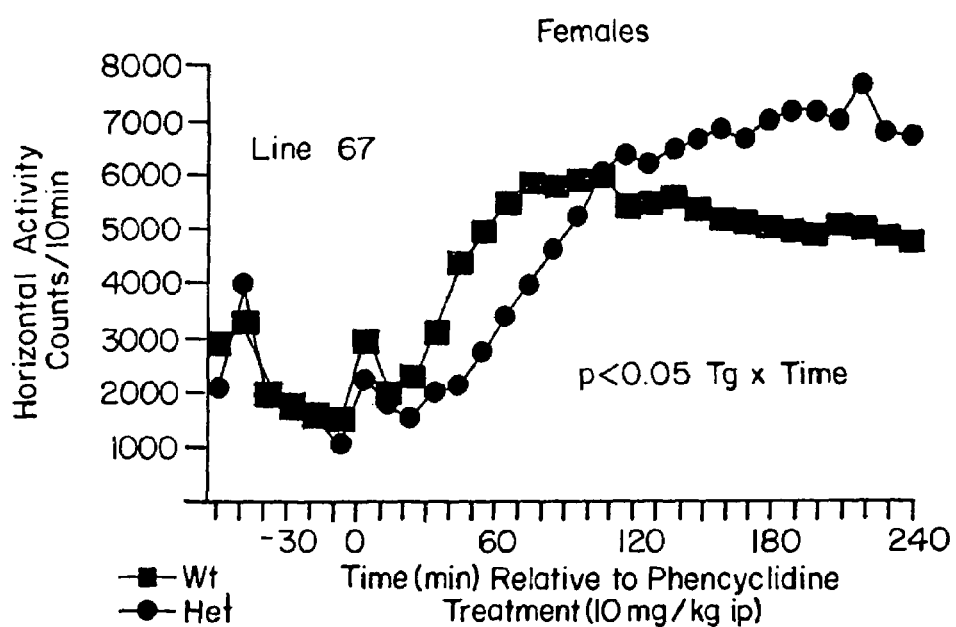

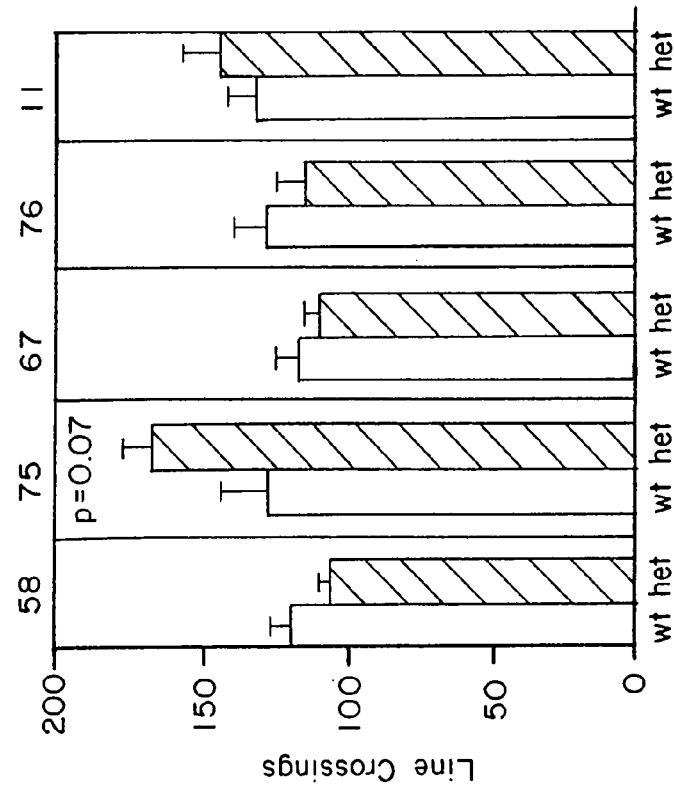
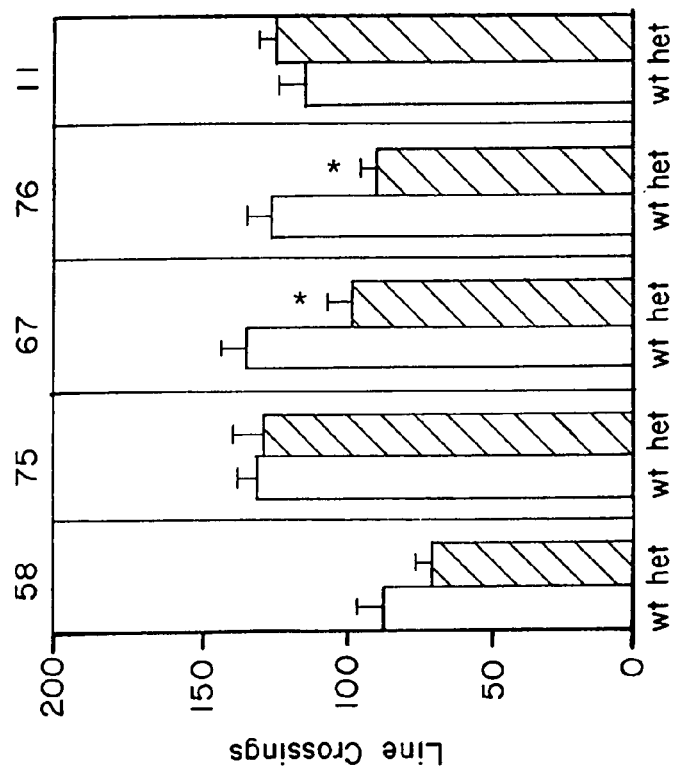
FIG. 22A
FIG. 22B

SEQUENCE LISTING

<160> NUMBER OF SEQ ID NOS: 10

<210> SEQ ID NO 1
<211> LENGTH: 1097
<212> TYPE: DNA
<213> ORGANISM: Artificial Sequence
<220> FEATURE:
<223> OTHER INFORMATION: fragment of the mouse G alpha q cDNA containing
      G to A substitution
      at the nucleotide 573 and a G to C substitution at nucleotide
      575 that converts Gly to Ser at codon 188 as well as several other
      nucleotide changes

<400> SEQUENCE: 1

```
ctcgagccac catgactctg gagtccatca tggcgtgctg cctgagcgag gaggccaagg      60
aagcccggag gatcaacgac gagatcgagc ggcacgtgcg cagggacaag cgcgacgccc     120
gccgggagct caagctgctg ctgctgggga caggggagag tggcaagagc accttcatca     180
agcagatgag gatcatccac gggtcgggct actctgacga agacaagcgc ggcttcacca     240
agctggtgta tcagaacatc ttcacggcca tgcaggccat gatcagagcg atggacacgc     300
tcaagatccc atacaagtat gaacacaata aggctcatgc acaattggtt cgagaggttg     360
atgtggagaa ggtgtctgct tttgagaatc catatgtaga tgcaataaag agcttgtgga     420
atgatcctgg aatccaggag tgctacgaca gcgacgggga atatcagtta tctgactcta     480
ccaaatacta tctgaatgac ttggaccgtg tagccgaccc tgagtacatg ccgacagagc     540
aagacgtgct tagagttcgg gtacccacta caagcatcat cgaataccccc tttgacttac     600 aaagtgtcat tttcagaatg gtcgatgtag ggggccaaag gtcagagaga agaaaatgga     660
tacactgctt tgaaaatgtc acctccatca tgtttctagt agcgcttagc gaatatgatc     720
aagttcttgt ggagtcagac aatgagaacc gcatggagga gagcaaagca ctctttagaa     780
caattatcac ctaccctgg ttccagaact cctctgtgat tctgttctta aacaagaaag     840
atcttctaga ggagaaaatc atgtattccc acctagtcga ctacttccca gaatatgatg     900
gaccccagag agatgcccag gcagcccgag aattcatcct gaaaatgttc gtggacctga     960
accccgacag tgacaaaatc atctactccc acttcacgtg cgcccacaga accgagaaca    1020
tccgcttcgt ctttgcagcc gtcaaggaca ccatcctgca gctgaacctg aaggagtaca    1080
atctggtcta actcgag                                                   1097
```

<210> SEQ ID NO 2
<211> LENGTH: 359
<212> TYPE: PRT
<213> ORGANISM: Artificial Sequence
<220> FEATURE:
<223> OTHER INFORMATION: mouse G alpha q containing Gly to Ser
      substitution at codon 188
      as well as several other changes to include an EE epitope tag

<400> SEQUENCE: 2

```
Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg His Val Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Glu Tyr Met Pro Thr Glu
                165                 170                 175

Gln Asp Val Leu Arg Val Arg Val Pro Thr Thr Ser Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 3
<211> LENGTH: 38
<212> TYPE: DNA
<213> ORGANISM: Artificial Sequence
<220> FEATURE:
<223> OTHER INFORMATION: PCR primer DH1 (+1 to +29 bp G alpha q)

<400> SEQUENCE: 3
```

```
gttaagcttc tcgagccacc atgactctgg agtccatc                              38
```

```
<210> SEQ ID NO 4
<211> LENGTH: 29
<212> TYPE: DNA
<213> ORGANISM: Artificial Sequence
<220> FEATURE:
<223> OTHER INFORMATION: PCR primer DH2 (+933 to +905 bp G alpha q)

<400> SEQUENCE: 4
attctcgggc tgcctgggca tctctctgg                                        29

<210> SEQ ID NO 5
<211> LENGTH: 32
<212> TYPE: DNA
<213> ORGANISM: Artificial Sequence
<220> FEATURE:
<223> OTHER INFORMATION: PCR primer DH3 (+916 to +947 bp G alpha q)

<400> SEQUENCE: 5
cccaggcagc ccgagaattc atcctgaaaa tg                                    32

<210> SEQ ID NO 6
<211> LENGTH: 32
<212> TYPE: DNA
<213> ORGANISM: Artificial Sequence
<220> FEATURE:
<223> OTHER INFORMATION: PCR primer DH4 (+1097 to +1074 bp G alpha q)

<400> SEQUENCE: 6
ggcgatccct cgagttagac cagattgtac tc                                    32

<210> SEQ ID NO 7
<211> LENGTH: 18
<212> TYPE: DNA
<213> ORGANISM: Artificial Sequence
<220> FEATURE:
<223> OTHER INFORMATION: PCR primer DH10 (+410 to +427 bp G alpha q)

<400> SEQUENCE: 7
gagcttgtgg aatgatcc                                                    18

<210> SEQ ID NO 8
<211> LENGTH: 18
<212> TYPE: DNA
<213> ORGANISM: Artificial Sequence
<220> FEATURE:
<223> OTHER INFORMATION: PCR primer DH14 (+349 to +332 bp G alpha q)

<400> SEQUENCE: 8
accaattgtg catgagcc                                                    18

<210> SEQ ID NO 9
<211> LENGTH: 18
<212> TYPE: DNA
<213> ORGANISM: Artificial Sequence
<220> FEATURE:
<223> OTHER INFORMATION: PCR primer DH15 (+631 to +614 bp G alpha q)

<400> SEQUENCE: 9
cctacatcga ccattctg                                                    18

<210> SEQ ID NO 10
<211> LENGTH: 18
<212> TYPE: DNA
<213> ORGANISM: Artificial Sequence
```

```
<220> FEATURE:
<223> OTHER INFORMATION: PCR primer DH16 (+2502 to +2520 bp Thy1.2)

<400> SEQUENCE: 10
ggatctcaag ccctcaag                                                    18
```

TRANSGENIC ANIMAL

This application claims priority under 35 U.S.C. § 119 from Provisional Application Nos. 60/199,209 and 60/245,473 filed Apr. 24, 2000 and Nov. 3, 2000, respectively, which are each incorporated herein by reference in their entirety.

FIELD OF THE INVENTION

The invention generally relates to transgenic animals (rats and mice) and to animal models of human disease. The invention particularly relates to transgenic animals which can serve as animal models of human diseases or conditions modulated by proteins that regulate G-protein signaling.

BACKGROUND OF THE INVENTION

The RGS (Regulators of G-protein Signaling) proteins act to desensitize G protein mediated signal transduction by accelerating the endogenous GTPase activity of activated $G\alpha$ subunits. RGS proteins have been demonstrated to function as GAPs (GTPase accelerating proteins) for $G\alpha o$, $G\alpha i$, $G\alpha z$ and $G\alpha q$ subtypes of the $G\alpha$ subunit (Grafstein-Dunn, et al. Mol. Brain Res. 2001, 88:113-123; for a review see Hepler, Trends in Pharmaceutical Sci. 1999, 20:376-382). Therefore, RGS proteins accelerate the turning-off of G-protein coupled receptor GPCR signaling. RGS proteins likely modulate signal transduction of many clinically relevant GPCRs within the CNS. In situ analyses by Gold et al., (Neurosci. 1997, 17(20):8024-37) demonstrated brain specific RGS mRNA expression. Additional in situ evaluation demonstrated overlap of mRNA expression for RGS4, RGS7, and $G\alpha q$ (Shuey et al., J. Neurochem. 1998, 70:1964-1972).

The first member of the RGS protein family (SST2p) was identified in yeast using a genetically characterized mutant yeast strain (sst) supersensitive to the ligand of the pheromone response pathway (Dohlman et a., Mol Cell Biol. 1996, (9):5194-209). The receptor for this pathway is a G-protein coupled, seven transmembrane receptor (GPCR). The components of this yeast pathway are analogous to those in mammalian GPCR signaling. Subsequently, a dominant mutation was identified in yeast that phenotypically copied a yeast strain deleted for the yeast RGS (SST2p). The mutation also resulted in a supersensitivity to the GPCR ligand, alpha factor, which stimulated the pheromone response pathway in yeast leading to cell cycle arrest. The dominant mutation was identified using genetic studies and molecular biology in yeast (Dohlman et al., (supra), and was due to a G302S mutation in the yeast G protein (Gpa1) that rendered it insensitive to regulation by (RGS) SST2. Gpa1 is homologous to mammalian $G\alpha i$ proteins. The glycine residue is conserved in mammalian $G\alpha$ subunits and is contained within the first switch region in the $G\alpha$ protein. Crystallography studies show that the switch regions of $G\alpha i$ interacts with RGS4 (Tesmer et al., Science 1997, 278 (5345):1907-16). The dominant phenotype (RGS insensitivity) resulting from the G302S mutation in the $G\alpha$ protein identified in yeast can be transferred to the mammalian $G\alpha q$ protein (Shuey et al., J. Neurochem. (1998, 70:1964-1972). This work extended the RGS insensitive phenotype of the yeast protein, Gpa1, to mammalian $G\alpha q$ protein (G188S). The mammalian $G\alpha$ protein harboring the G to S mutation is able to bind the guanine nucleotide, but is resistant to the GAP activity of RGS proteins.

Since the identification of the first member (yeast protein, SST2) of the RGS protein family in 1996, the impact and biology of the RGS proteins remains to be clarified. RGS proteins are implicated to play a role in brain function, as suggested by region specific expression.

In particular, several GPCRs couple through $G\alpha q$ to activate second messenger systems (Forse, Crit. Care Med. 2000, 32:524-30; Gudermann et al., Ann. Rev. Neurosci. 1997, 20:399-427) such as PLC, phosphotidyl inositol, Diacyl glycerol, PKC and calcium. Additionally, these messengers can link into MAP kinase pathways to further modulate cellular responses. The $G\alpha q$ coupled receptors include (but are not limited to) the α1 adrenergic receptor, muscarinic receptors (m1, m3, m5), adrenoreceptors, N-methyl D-aspartate receptors, histamine receptors, serotonin receptors, P2Y, and metabotropic glutamate receptors. Many of these receptors show distinct expression patterns in the brain. The $G\alpha q$ coupled serotonin receptors (5-HT2A, 5-HT2B, 5-HT2C) are of particular interest because this neurotransmitter system is targeted by several anti-depressant therapeutics.

Of the anti-depressant therapeutics, lithium is the most commonly used treatment for bipolar affective disorder (Jope, Mol. Psychiatry 1999, 4:21-25 and 117-28). Despite its years of usage, the therapeutic mechanism of action of lithium has not been clearly elucidated. Lithium produces a wide spectrum of behavioral and neurochemical effects leading to speculation that its mechanism(s) of action relates to its effects on one or more signaling pathways: G-proteins, IP3, cAMP, wnt, β-catenin, GSK3b, etc. (Williams and Harwood, Trends Pharmaceutical Sci. 2000, 21:61-64; Hedgepath et al., Basic Res. Cardiol. 1997, 92:385-90).

Despite the considerable efforts aimed at elucidating the mechanism of action of therapeutics such as lithium for treating bipolar disorders, there is no clear picture of how such compounds work. An understanding of how compounds such as lithium exert their effects would allow for the design and testing of novel therapeutics that produce a desired therapeutic effect while potentially avoiding adverse side effects. G-protein signaling constitutes an area where additional information could help elucidate specific mechanisms. Accordingly, there is a need for model animal systems which can be used to identify mechanisms of action of RGS blockers and to use as a model for $G\alpha q$ mediated activity, or discernment of G-protein crosstalk, in receptor function. Establishment of transgenic animals can provide insight into the biological relevance, and potential therapeutic application, for a molecular target.

To this end, transgenic rats that express the RGS insensitive $G\alpha q$ mutant (G188S) in neuronal tissue were established. These animals were assessed for transgene expression and behaviors to implicate RGS control of $G\alpha q$ mediated GPCRs of neurological importance.

SUMMARY OF THE INVENTION

The present invention provides transgenic animals having a transgene which functions as a dominant negative mutation, i.e., its expression inhibits normal cellular processes. Transgenic animals of the type described are useful in any situation where an unmutated endogenous gene regulates or is regulated in a normal function in the animal. Introducing a dominant negative transgene makes it possible to assess gradations of activity in different animal lines, depending on the level of expression of the transgene, as it overrides regulatory function of the endogenous system to varying degrees. This strategy is useful where a knockout of the endogenous gene is fatal or where the endogenous gene is a member of a group of genes encoding similar or overlapping functions. In the latter case, the related genes may interact in a hierarchical or compensatory manner such that the phenotypic effect of a simple knockout fails to provide useful or accurate information of the gene's function. An example of such related genes is provided by the genes encoding proteins of the G-protein signaling pathways which control intracellular responses to the presence of ligands like hormones, neurotransmitters, and the like outside the cell. As described herein, the RGS proteins are components of G-protein signaling and function to modulate GPCR signalling upon binding ligand, such as neuronal responses to neurotransmitters in the central nervous system, in particular by terminating or attenuating the signal. The transgenic animals exemplified in the present invention express a transgenic variant protein which is functional in G-protein signaling, but which is insensitive to RGS protein. In a specific embodiment, expression of a mutant Gα protein uncouples it from RGS regulation. Alternatively, overexpression of Gα protein competitively inhibits RGS activity, also uncoupling G protein signaling.

The present invention further includes a method for making a transgenic animal that includes the steps of identifying a variant coding sequence controlling a dominant negative function and introducing the variant coding sequence into animal cells to produce transgenic animal cells that replicate to produce a transgenic animal. The method can also include the step of providing a tissue-specific expression control element operationally linked to the variant coding sequence so that expression of the dominant negative function is confined to a desired tissue type, such as the brain, of the transgenic animal. The method can produce many animal lines bearing the same transgene but differing in transgene expression levels. Comparing the varied phenotypes of such lines permits analysis of the quantitative influence of the dominant negative transgene.

The invention also provides, as exemplified, transgenic rat lines bearing a dominant negative G protein, specifically a Gαq mutant protein, as described in detail herein. The mutant Gαq coding sequence has been combined with a neuron-specific promoter, Thy 1.2, a known pan-neuronal tissue-specific promoter. Differences in expression level among different rat lines are attributable to different loci of integration within the genome. The transgene has also been combined with a readily identifiable epitope which can be used to identify and quantitate transgene expression levels by immuno-detection. Various psychomotor and drug response effects have been identified in the transgenic rats, as described below. Unexpectedly, doses of a 5HT2A agonist which were non-toxic to normal (wt) rats were lethal to the transgenic rats of the invention. These transgenic rats also displayed increased sensitivity to the 5HT2C induced feeding response. These and other observations demonstrated that 5HT2 mediated responses were altered in the transgenic rats. Additionally, the transgenic rats showed increased sensitivity to the nuscarinic agonist pilocarpine. The transgenic rats of the invention are useful for analyzing the spectrum of pharmacological action of psychoactive drugs and as research tools for determining the activities and interactions of G-proteins in regulation and modulation of nerve cell and brain function. Such understanding is essential to the design and testing of pharmacologic agents for treatment of nerve and brain disorders including, without limitation, depression, anxiety, obsessive-compulsive disorder, hyperactivity, sleep disorders, psychoses, schizophrenia, cognition disorders, pain, mood disorders, eating disorders, autism, attention deficit disorders, bipolar affective and the like.

DESCRIPTION OF THE FIGURES

FIG. 1 (A-C) is the nucleotide (SEQ ID No: 1) and amino acid (SEQ ID NO: 2) sequence of mouse G188S Gαq.

FIG. 2 is a schematic diagram of the mutant mouse Gαq transgene.

FIG. 5 shows the results of the effect on body weight in LiCl diet treated rats.

FIG. 11 (A and B) shows prepulse inhibition (A) and acoustic startle (B) studies in rats treated with acute lithium.

FIG. 22 (A and B) shows open field behavior (line crossings) in Gq transgenic rats.

DETAILED DESCRIPTION OF THE INVENTION

Figure 3A:
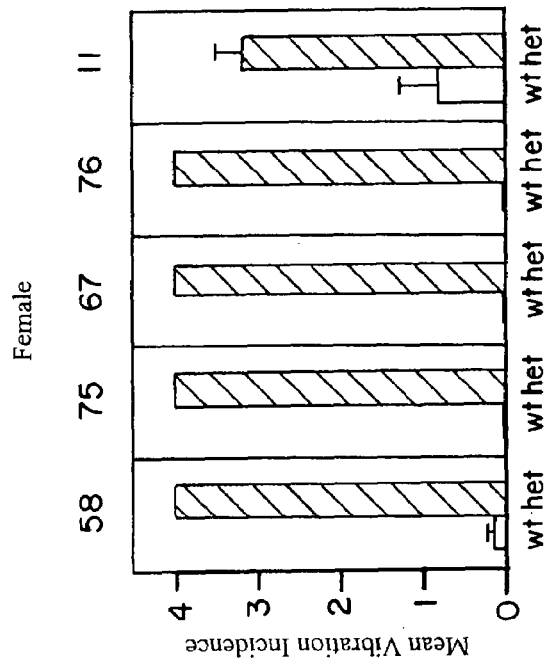
FIG. 3 (A and B) shows global behavioral assessment in male (A) and female (B) Gq transgenic rats.

The family of RGS protein contains approximately 20 members (Ross and Wilkie, Ann. Rev. Biochem. 2000,69: 795-827, especially 796-803). Systematic deletion of each individual RGS subtype would be an enormous undertaking. In addition, different RGS proteins are co-expressed in various brain regions, so the effect of a deletion of a particular RGS protein may be masked by co-expression of a different RGS. Additionally, proteins may functionally compensate for a deleted protein, a role that may be artificially induced by a knockout. To gain a more global insight into the function of RGS proteins, transgenic rats were generated that express a Gαq mutant that is resistant to the GAP activity of RGS proteins. Gαq is expressed at lower levels in the brain in comparison to Gαo or Gαi subtypes, and therefore provides a greater opportunity to observe a transgene effect. Toward this end, rats were generated that express the mouse Thy1.2-G188S Gαq transgene (FIG. 2).

It was discovered that many of the behavioral and pharmacological effects of lithium (Kofman and Petishi, Eur. Neuropsychopharmacol. 1999, 9:385-97) are exhibited by the transgenic rats of the invention. The transgenic rats of the invention overexpress a mutant form of Gαq, which is not regulated by RGS-protein, thus resulting in a model of RGS blockade. Similar to the Gαq mutant transgenics, wild-type rats treated with lithium have a mild tremor or vibration, have decreased food intake and body weight and have deficits in prepulse-inhibition. Moreover, either acute or chronic lithium attenuates the locomotor activating effects of the indirect dopamine agonist amphetamine and potentiates responses to the 5-HT2A agonist DOI, the 5-HT2C agonist RO 60-0175, the muscarinic agonist pilocarpine, and the noncompetitive NMDA antagonist PCP. In short, the Gαq mutant animals exhibit a phenotype of lithium treated animals.

The parallels observed between the Gαq mutant transgenic rats and lithium treated rats indicates that Gαq mutant transgenic rats represent a treated model of bipolar affective disorder. Since the Gαq mutant transgenic animals mimic the effects of RGS-blockade, these parallels indicate that RGS blockers are useful in the treatment of bipolar affective disorder. Moreover, the transgenic animals represent a more precise model of RGS blockade than lithium treatment, and thus are useful for studying the effects of other drugs or RGS-blocked animals.

In the disclosure below, the invention is discussed in terms of transgenic rats. It should be apparent that the invention includes transgenic mice as shown in Example 3, below, and generally relates to transgenic rodents (e.g., rabbits, hamsters, gerbils, and guinea pigs in addition to rats and mice), as well as other animals having a transgene which functions as a dominant negative. The transgenic animals of the invention are genetically modified animals in which at least one foreign gene has been inserted into the genome. These animals allow regulatory processes on the cellular level to be examined and influenced in a systematic and specific manner not achievable with any other test systems. Transgenic animals of the type described are useful in any situation where an unmutated endogenous gene controls an inhibitory function in the animal. In particular, the transgenic animals of the invention are useful for analyzing the spectrum of pharmacological action of psychoactive drugs, and as research tools for determining the activities and interactions of G-proteins in regulation and modulation of nerve cell and brain function, and function in other tissues. The transgenic animals serve as excellent models for evaluating the effect of compounds, i.e., potential or actual ligands of GPCRs, in context of decoupling GPCR signaling from RGS protein regulation. Such understanding is essential to the design and testing of pharmacologic agents for treatment of nerve and brain disorders including, but not limited to, depression, anxiety, obsessive-compulsive disorder, hyperactivity, sleep disorders, psychoses, schizophrenia, cognition disorders, pain, mood disorders, eating disorders, autism, attention deficits and the like.

Introduction of a dominant negative transgene makes it possible to assess gradations of activity in different animal lines, depending on the level of expression of the transgene as it overrides the function of the endogenous gene, to varying degrees. The strategy is useful where a knockout of the endogenous gene may be fatal or where the endogenous gene is a member of a group of genes encoding similar or overlapping functions. In the latter case, the related genes may interact in a hierarchical or compensatory manner such that the phenotypic effect of a simple knockout fails to provide useful or accurate information of the gene's function. An example of such related genes is provided by the genes encoding proteins of the G-protein signaling pathways which control intracellular responses to the presence of hormones, neurotransmitters and the like outside the cell. As described herein, the RGS proteins are a component of G-protein signaling which function to modulate neuronal responses to neurotransmitters in the central (and peripheral) nervous system. The transgenic animals exemplified in the present invention possess a transgenic variant protein which is functional in G-protein signaling but which is insensitive to RGS.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B.Perbal, A Practical Guide To Molecular Cloning (1984); F. M. Ausubel et al. (eds.), Current Protocols in Molecular Biology, John Wiley & Sons, Inc. (1994).

Molecular Biology—Definition

The transgenes herein may comprise a coding sequence (e.g., cDNA, a synthetic coding sequence, or genomic DNA) for a Gα subunit protein flanked by natural regulatory (expression control) sequences, or associated with heterologous sequences, including promoters, internal ribosome entry sites (IRES) and other ribosome binding site sequences, enhancers, response elements, suppressors, signal sequences, polyadenylation sequences, introns, 5'- and 3'- non-coding regions, and the like. The coding sequence may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include introns and regulatory DNA sequences, such as promoter sequences, 5'-untranslated region, or 3'-untranslated region which affect for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S 1), as well as protein binding domains (consensus sequences) responsible for the binding of RNA polymerase. The promoter may be operatively associated with other expression control sequences, including enhancer and repressor sequences.

Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes thymidine kinase promoter (Wagner et al., Proc. Natl. Acad. Sci. USA 1981, 78:1441-1445), the regulatory sequences of the metallothionein gene (Brinster et al., Nature 1982, 296:39-42); promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit neuronal or brain specific expression, such as the gonadotropic releasing hormone gene control region which is active in the hypothalamus (Mason et al., Science 1986, 234:1372-1378), the Thy1.2 "pan-neuronal" promoter, and synapsin I promoter (Howland D, Savage M., Huntress F., Wallace R., Schwartz D., Loh T., Melloni R., DeGennaro L., Greenberg B., Siman R., Swanson M., and Scott R. 1995. Mutant and Native Human B-Amyloid Precursor Proteins in Transgenic Mouse Brain. Neurobiol. Aging. 16: 685-699), active in neurons.

A coding sequence is "under the control of" or "operatively associated with" transcriptional and translational control sequences in a cell when RNA polymerase transcribes the coding sequence into mRNA, which is then trans-RNA spliced (if it contains introns) and translated, in the case of mRNA, into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. Furthermore, in the context of the present invention, expression includes mainfestation of decoupling of GPCR signaling from RGS proteins. A DNA sequence is expressed in or by a cell to form an "expression product" such as a protein. The expression product itself, e.g. the resulting protein, may also be said to be "expressed". An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to an ES cell or pronucleus, so that the cell will express the introduced gene or sequence to produce a desired substance in a transgenic animal.

The terms "vector", "cloning vector" and "expression vector" mean the vehicle by which a DNA or RNA sequence (e.g. a foreign gene) can be introduced into a host cell, (e.g. ES cell or pronucleus) so as to transform the host and promote expression (e.g. transcription and translation) of the introduced sequence.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature.

The terms "mutant" and "mutation" in the context of the invention mean any detectable change in genetic material encoding a Gα subunit protein, e.g., DNA, or any process, mechanism, or result of such a change that involves partial or complete uncoupling of the Gα subunit from RGS proteins. This includes gene mutations, in which the structure (e.g., DNA sequence) of a gene is altered, any gene or DNA arising from any mutation process, and any expression product (e.g., protein or enzyme) expressed by a modified gene or DNA sequence. The term "variant" may also be used to indicate a modified or altered gene, DNA sequence, enzyme, cell, etc., i.e., any kind of mutant. Specific examples of such mutations include the one corresponding to a glycine to serine substitution at position 188 of mouse Gαq protein, and Gαi mutations corresponding to the mutation in yeast Gpa1 resulting in a glycine to serine substitution at position 302.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions. In particular, Gα subunit proteins are homologous, particularly Gαq and Gαi families. Similarly, RGS proteins are homologous, especially with respect to the RGS domain (Ross and Wilkie, supra).

Gα Subunit Proteins and RGS Proteins

The present invention provides for expression of a mutant Gα subunit protein, or overexpression of a normal Gα subunit protein, so that G-protein mediated signal is uncoupled from regulation by RGS proteins without altering GTP binding by the Gα, or its ability to transduce a signal upon ligand binding to a GPCR. This can occur if a mutation in the Gα protein reduces or ablates its ability to interact with one or more RGS proteins. This can also occur on overexpression of the Gα subunit, so that some Gα not associated with the G-protein complex binds one or more RGS proteins, preventing them from regulating signaling by the complex.

In specific embodiments, mutant Gα proteins contain a glycine to serine substitution at a position homologous to amino acid residue 188 of murine Gαq, or amino acid residue 302 of yeast Gpa1. Other examples of mutants include Gαz, e.g., in which glutamine at position 205 is substituted with leucine (Q205L).

In addition to functioning in the G-protein complex, Gα mutants of the invention bind the RGS domain of RGS proteins with reduced affinity, or not at all. Thus, the RGS proteins do not regulate Gα activity, i.e., the RGS proteins do not mediate increase rate of hydrolysis of GTP bound to the Gα subunit protein. RGS proteins are described above, and in Ross and Wilkie (Annu. Rev. Biochem. 2000, 69:795-27) and Zheng (TIBS 1999, 24:411-14). Particularly preferred subfamilies of RGS proteins are the RZ, R4, R7, and R12 families. Thus, mutant variants of Gα for use in transgenic animals of the invention can be readily identified by reduction or elimination of binding to one or more RGS proteins, without inhibiting signal function.

Transgenic Animal Preparation

Transgenic animals can be produced by several methods known to those skilled in the art. One method involves taking fertilized oocytes from a female animal. A desired foreign DNA or transgene can then incorporated into the oocytes. Incorporation of the transgene into the oocyte can be accomplished by several methods such as via an appropriate retroviral vector, or by microinjection.

As noted above, any transgenic animal can be used. Preferred, especially because they are well studied for behavioral responses, are rats (or any species, including Sprague-Dawley (Taconic Labs), Long Evans (Taconic), Fischer 344 (Taconic), and Wistar. (Taconic). Because of their close evolutionary relationship, mice are also useful. Mouse strains include but are not limited to BALB/C, BL-6, DBA/2, etc. In addition to Taconic, suitable rats, mice and other animals are available from Charles River, Jackson Laboratories, and colonies in accredited animal care facilities.

Techniques for creating a transgenic animal, particularly a mouse or rat are well known (Gordon, International Review of Cytology1989, 115:171-229). Various approaches to introducing transgenes are available, including microinjection of nucleic acids into cells, developed in 1973 (in this technique, as of 1980, frequency of gene transfer ranged from 5% to 20%), retrovirus vector methods, and gene transfer into embryonic stem (ES) cells. The ES technique in particular permitted manipulation of the cells in culture (see also Bradley and Liu (Nature Genetics 1996, 14:121). For example, Capecchi developed a method by which transgenes can be incorporated into embryonic, fetal or adult pluripotent stem cells (*Science* 244:1991, 1288-1292). In Capecchi's method, embryonic stem cells are isolated from blastocysts cultivated in vitro. These embryonic stem cells can be kept stable in culture over many cell generations without differentiation. The transgene can then incorporated into the embryonic stem cells by electroporation or other methods of transformation. Stem cells carrying the transgene were selected for and injected into the inner cell mass of blastocysts. The blastocysts were then implanted into pseudopregnant females. Since not all the cells of the inner cell mass of the blastocysts carry the transgenes, the animals are chimeric with respect to the transgenes. Crossbreeding of the chimeric animals allows for the production of animals which carry the transgene. An overview of the process is provided by Capecchi Trends in Genetics 1989, 5:70-76.

The control of gene expression is accomplished by a variety of means well-known in the art. Expression of a transgene can be constitutive or regulated to be inducible or repressible by known means, typically by choosing a promoter that is responsive to a given set of conditions, e.g. presence of a given compound, or a specified substance, or change in an environmental condition such as tissue type or temperature. In examples described herein, the mutant Gαq coding sequence has been combined with a neuron specific promoter, Thy 1.2, a known pan-neuronal tissue-specific promoter. The term "inducible expression" extends to any means for causing gene expression to take place under defined conditions, the choice of means and conditions being chosen on the basis of convenience and appropriateness for the host organism.

Transformation can be carried out by a variety of known techniques, depending on the organism, on characteristics of the organism's cells and of its biology. Stable transformation involves DNA entry into cells and into the cell nucleus. For organisms that can be regenerated from single cells (which includes some mammals), transformation can be carried out in in vitro culture, followed by selection for transformants and regeneration of the transformants. Methods often used for transferring DNA or RNA into cells include microinjection, particle gun bombardment, forming DNA or RNA complexes with cationic lipids, liposomes or other carrier materials, electroporation, and incorporating transforming DNA or RNA into virus vectors. Other techniques are known in the art. For a review of the state of the art of transformation, see standard reference works such as Methods in Enzymology, Methods in Cell Biology, Molecular Biology Techniques, all published by Academic Press, Inc. N.Y. DNA transfer into the cell nucleus occurs by cellular processes, and can sometimes be aided by choice of an appropriate vector, by including integration site sequences which can be acted upon by an intracellular transposase or recombinase (see e.g, [Craig, *Ann. Rev. Genet.* 1988, 22:77; Cox. In *Genetic Recombination* (R. Kucherlapati and G. R. Smith, eds.) 1988, American Society for Microbiology, Washington, D.C., pages 429-493; Hoess. In *Nucleic Acid and Molecular Biology* (F. Eckstein and D. M. J. Lilley eds.) Vol. 4, 1990, Springer-Verlag, Berlin, pages 99-109. Direct transformation of multicellular organisms can often be accomplished at an embryonic stage of the organism. For example, in *Drosophila*, as well as other insects, DNA can be microinjected into the embryo at a multinucleate stage where it can become integrated into many nuclei, some of which become the nuclei of germ line cells. By incorporating a marker as a component of the transforming DNA, non-chimeric progeny insects of the original transformant individual can be identified and maintained. Direct microinjection of DNA into egg or embryo cells has also been employed effectively for transforming many species. In the mouse, the existence of pluripotent embryonic stem (ES) cells that are culturable in vitro has been exploited to generate transformed mice. The ES cells can be transformed in culture, then micro-injected into mouse blastocysts, where they integrate into the developing embryo and ultimately generate germline chimeras (see, e.g. Haren et al, *Annu. Rev. Microbiol.* 1999 53:245-281; Reznikoff et al., *Biochem. Biophys. Res. Commun.* 1999, 266(3):729-734; Ivics et al, Methods Cell Bid. 1999, 60:99-131; Hall et al., *FEMS Microbiol. Rev.* 1997, Sep:21(2):157-178; Craig *Annu. Rev. Biochem* 1997, 66:437-474; Beall et al. *Genes Dev.*, 1997, 11(16):2137-2151). By interbreeding heterozygous siblings, homozygous animals carrying the desired gene can be obtained.

In general transgenic animals of the invention include any transformable species except humans. Of particular interest are mammals, including known transformable species such as mouse, rat, sheep, and pig, and others, as transformation methods are developed, including bovine and non-humans primates and model organisms such as *C. elegans*, zebra fish, and yeast (*S. cerevisiae, S. pombe* and *P. Pastoris*).

Phenotype

As used herein, the term "phenotype" includes biochemical characteristics, such as extended GPCR signaling, i.e., due to uncoupling of RGS protein regulation of GPRC signaling, to physical manifestations of such uncoupling in the animal like increased sensitivity to various compounds and GPCR, and behavior changes in the animal. As used herein, the term "uncoupling" means inhibition or blockade of RGS protein interaction with the Gα protein, whether by action of a Gα mutant or by overexpression of Gα.

A variety of behavioral tests are known to those skilled in the art which can be used to characterize transgenic animals and which can be used to determine the therapeutic indications of transgenic animals and animals used in the methods of the invention. Such behavioral tests include, but are not limited to, open field, global assessments, body weight, food intake, startle and prepulse inhibition, contextual fear and auditory cue conditioning, responsiveness to shock, pharmacological responses, and locomoter activity.

Uses of Transgenic Animals of the Invention

The transgenic animals of the invention can be used to identify compounds or compositions that block RGS function or activate or prolong Gα signaling. This is defined herein as "modulating activity". Particularly, the transgenic animals of the invention are useful for analyzing the spectrum of pharmacological action of psychoactive drugs, and as research tools for determining the activities and interactions of G-proteins in regulation and modulation of nerve cell and brain function. Such understanding is essential to the design and testing of pharmacologic agents for treatment of nerve and brain disorders including, but not limited to, depression, anxiety, obsessive-compulsive disorder, hyperactivity, sleep disorders, psychoses, schizophrenia, cognition disorders, pain, mood disorders, eating disorders, autism, attention deficits disorders, bipolar affective disorders, and the like.

Agents That Mimic The Phenotype of the RGS Insensitive Transgenic Rats

The results presented in this application support the parallels observed between the RGS insensitive Gαq mutant transgenic rats, and lithium treatment of wildtype rats; thereby indicating that an agent (e.g., small molecules, peptides, antibodies, antisense oligonucleotides) capable of modulating RGS function (i.e., blocking) can be used to treat diseases treated by lithium, such as bipolar affective disorder.

Comparative use of the animals described herein can be used to identify novel therapeutics. For example, unknown agents (compounds or peptides etc.) can be administered (using various concentrations) to untreated normal rats, lithium exposed normal rats, and untreated transgenic rats. Animals are scored for agent effect in a plurity of tests similar to (but not limited to) behavioral analysis as described herein.

Key tests for the lithium phenotype are those that specifically relate to the IP3 pathway, including RO food intake, DOI headshakes, and pilocarpine cholinergic signs, all of which link to Gq-mediate receptor signals. These are the preferred minimum tests for establishing a link to the effect of lithium.

In one embodiment, untreated control rats are administered a test compound, or vehicle, while transgenic rats receive vehicle only. Comparison of these three groups (wildtype+vehicle, wildtype+compound, transgenic rat+vehicle) using one or more behavorial phenotype or other phenotype characterization of tests such as those described herein, allows for scoring differences in behavior. Wildtype animals that received a potential agent that scored similarly to transgenic rats+vehicle, identify an agent which functions through a mechanism similar to that observed in the transgenic rat. If the results of these tests in the transgenic animals are substantially the same as those obtained in the treated group then the drug interacts as in the RGS pathway and can be used to treat, e.g., bipolar diosorders. As used herein, the term "substantially the same" means that the same qualitative (alteration of phenotype) or quantitative (shift in potency) change. For example, transgenic rats and lithium treated rats both have uncreased sensitivity to DOI (a qualitative change), and similar shifts in potency of RO and pilocarpine (a quantitative change).

EXAMPLES

The following examples are provided as illustrations of specific preferred embodiments and are not intended to limit the scope of the invention.

Example 1
Cloning of The TransgenePCR
Amplification and Cloning of The Gαq G188S
Transgene Plasmid pcDNAamp Gqsst (DiBello et al. J. Biol. Chem. 1998, 273:5780-5784) was used as a template to PCR a 1.1 kb fragment of the mouse Gαq cDNA. Gqsst contains a G to A conversion at nucleotide 573 and a G to C conversion at nucleotide 575 that converts a glycine residue to serine at amino acid residue 188 (G188S) (see FIG. 1). In addition, several nucleotide changes were incorporated 5' to the mutation to convert an endogenous Gαq amino acid sequence portion to that of an EE epitope tag (FIG. 1) to allow mutant Gαq protein detection using anti-EE antisera. "EE" refers to a two glutamate sequence that is part of an epitope recognized by a commercially available mouse monoclonal antibody Glu-Glu (Babco, Berkley Antibody Company, Richmond, Calif.). This antibody was raised against the sequence CEEEEYMPE and is specific for either six amino acid sequences EYMPME or EFMPME. The EE epitope is known to be insertable into many G proteins without altering function. Primers (summarized in table 1) DH1, DH2, DH3, and DH4 were used in overlap PCR with elongase polymerase (BRL) to PCR the 1.1 kb mutant Gαq DNA. Primer DH1 contains an Xho I restriction endonuclease sequence just upstream of a consensus Kozak sequence (CCACCATG) which was incorporated into the 5' end of the Gαq cDNA. Primer DH4 overlaps the TAA stop codon also contained the Xho 1 restriction site enabling the 1.1 kb PCR product to be cloned as an Xho I restriction fragment. In the first round of PCR, primers DH1 and DH2 were used to generate a 0.9 kb DNA fragment in which nucleotide T at position 926 bp was converted to a C to destroy an endogenous Xho I restriction site. Primers DH3 and DH4 were used to generate the 3' end 0.2 kb of Gαq DNA which had partial overlap with the DH1/DH2 product at the destroyed Xho I site. The second step of PCR was done using products DH1/DH2 and DH3/DH4 and outside primers DH1 and DH4 to generate the final 1.1 kb mutant Gαq cDNA flanked by Xho I restriction sites. The 1.1 kb Xho I fragment was electrophoresed using a 1% agarose gel and was eluted by Gene-Clean (Bio-101) and subcloned into vector pGemT (Promega, Madison, Wis.). DNA sequence analysis confirmed that the 1.1 kb Gαq cDNA was authentic and contained the expected nucleotide changes for the glycine at position 188 change to serine (G188S) mutation as well as the incorporated EE epitope tag and modified Kozak consensus sequence.

point agarose gel (BRL) to allow separation of the 7.8 kb Thy1.2-Gαq G188S transgene DNA from smaller sized 2 kb and 1 kb fragments generated from restriction of the pUC19 vector (New England Biolabs) backbone. The 7.8 kb fragment was excised from the LMP gel and heated to 70° C. to melt the agarose. Once liquefied, an equal volume of phenol was used to extract the gel mix. The aqueous portion was re-extracted using a phenol-chloroform mix followed by chloroform. The aqueous fraction was then precipitated using 2 volumes of 95% ethanol, followed by a 70% ethanol wash. The DNA pellet was resuspended in 2.5 ml TE buffer. One gram of cesium chloride (Sigma, St. Louis, Mo.) was added for every 1 ml of DNA-TE mix and gently dissolved.

TABLE 1

| | PCR Primer Sequences | Coordinates | Seq Id No. |
|---|---|---|---|
| DH1 | GTTAAGCTTCTCGAGCCACCATGACTCTGGAGTCCATC | +1 to +29 bp Gαq | 3 |
| DH2 | ATTCTCGGGCTGCCTGGGCATCTCTCTGG | +933 to +905 bp Gαq | 4 |
| DH3 | CCCAGGCAGCCCGAGAATTCATCCTGAAAATG | +916 to +947 bp Gαq | 5 |
| DH4 | GGCGATCCCTCGAGTTAGACCAGATTGTACTC | +1097 to +1074 bp Gαq | 6 |
| DH10 | GAGCTTGTGGAATGATCC | +410 to +427 bp Gαq | 7 |
| DH14 | ACCATTGTGCATGAGCC | +349 to +332 BP Gαq | 8 |
| DH15 | CCTACATCGACCATTCTG | +631 to +614 bp Gαq | 9 |
| DH16 | GGATCTCAAGCCCTCAAG | +2502 to +2520 bp Thy1.2 | 10 |

Example 2

Construction of Tissue Specific Transgene

Expression Construct Cloning of Thy1.2-Gαg (G188S)

Plasmid Gαq (G188S)-GemT was cut with Xho I and the 1.1 kb Gαq cDNA was excised from a 1% agarose gel and eluted by Gene-Clean (Bio-101) according to manufacturer's protocol. Plasmid Thy1.2 containing a 6.7 kb NotI-PvuI mouse Thy1.2 minigene cloned in pUC19 was described previously. The 1.1 kb Gαq DNA was ligated to Thy1.2 vector DNA cut with Xho I and treated with calf intestinal alkaline phosphatase to remove 5' phosphate ends (Sambrook et al., 1982). Clone Thy1.2-Gαq (G188S) containing the 1.1 kb mutant Gαq cDNA in the correct orientation in the XhoI cloning site of the Thy1.2 expression cassette was verified by restriction mapping as well as DNA sequence analysis (see FIG. 2).

Example 3

Preparation of Transgenic Rat

Transgene Preparation For DNA Microinjection

Construct Thy1.2-Gαq G188S DNA (100 micrograms) was cut with NotI and PvuI restriction enzymes overnight at 37° C. The DNA was electrophoresed on 1% low melting Ethidium bromide (10 mg/ml) was added to a final concentration of 0.74 mg/ml and the sample was loaded into 3.9 ml heat sealable ultracentrifuge tubes (Beckman) and spun at 100,000 rpm for 4 h at 25° C. in a Beckman Optimax table top ultracentrifuge. Linear Thy1.2-Gαq G188S was eluted from the CsCl gradient and extracted 5 times with isopropanol to remove the ethidium bromide. The DNA was then dialyzed against microinjection buffer (5 mM Tris-HCl, pH 7.4, 0.1 mM Na$_2$ EDTA) overnight. Dialyzed DNA was diluted to 2 mg/ml for microinjection.

Transgenic Rat Production

Transgenic rats were produced using modifications of procedures described by (Hogan et al., Manipulating the Mouse Embryo. Cold Spring Harbor, N.Y.: Cold Spring Harbor Laboratory Press; 1986). Glass needles for microinjection were prepared using a micropipet puller and microforge. Injections were performed using a Nikon microscope with Hoffman Modulation Contrast optics, with Narashigi micromanipulators and a pico-injector driven by N$_2$ (Narashigi).

Fertilized Sprague-Dawley rat embryos were surgically removed from the oviducts of superovulated female rats and placed into M2 medium. Cumulus cells were removed from the embryos with hyaluronidase at 300 μg/ml. The embryos were then rinsed in fresh M2 medium, and transferred into M16 medium for storage at 37° C. prior to injection. After injecting the DNA solution into the male pronucleus, embryos were implanted into avertin-anesthetized SD recipient females made pseudo-pregnant by mating with vasectomized males. Embryos were allowed to develop to term, and the newborn rats were analyzed for the presence of the transgene as described below.

Founder Identification

A transgene-specific polymerase chain reaction (PCR) was developed to screen for founder transgenic rats. To obtain samples for PCR analysis, rat tail biopsies were at 6 to 8 days postnatal, and the biopsy material digested in proteinase K buffer containing 50 mM Tris-HCl, pH 7.5, 100 mM $Na_2EDTA$, 100 mM NaCl, 1% SDS, 1.6 mg/ml proteinase K at 56° C. overnight. Extracts were then spun at 14,000 rpm for 15 min to remove debris. To prepare for PCR, proteinase K digested samples were diluted 1:200 in water and then heated for 15 min at 95° C. 1 µl of diluted heat inactivated sample was then used in the PCR reaction. The DH16 primer sequence lies approximately 100 bp upstream of the ATG translation start codon in exon 2 of the Thy1.2-Gαq transgene. Primer DH14 lies 318 bp 3' to the ATG start in the Gαq coding sequence. PCR amplification was done using PCR supermix (Life Technologies, Gaithersburg, Me.) 22 mM Tris-HCl, pH 8.4, 55 mM KCl, 1.65 mM $MgCl_2$, 220 µM each nucleotide (dATP, dCTP, dTTP, dGTP), 22 units recombinant Taq DNA polymerase, and 1 µl DNA sample. PCR was performed using the following step conditions: 94° C., 5 min, 1 cycle, followed by 94° C., 1 min, 60° C., 1 min, 72° C., 1 min for 30 cycles, followed by 72°then a 4° C. soak using a MJ Research PTC 200 thermocycler. The 420 bp PCR product was resolved on a 2% Nusieve agarose-1% Seakem agarose gel (FMC).

A total of 11 founder rats were identified using the transgene specific PCR. Of these 10 rats were confirmed to contain integrated transgene DNA by Southern blot analysis (Sambrook et al., 1978). Founder number 80 was later shown to be nontransgenic. Two founders (# 37, # 64) died prior to reaching sexual maturity however the remaining 8 founders all produced transgenic f1 progeny upon mating to wild types.

Example 4

Preparation of Transgenic Mice

Transgene Preparation and DNA Microinjection

Construct Thy1.2-Gαq G188S DNA (100 micrograms) is obtained and treated as described above in Example 3. Because this is a murine sequence it is used identically as described in Example 3 above for production of transgenic rats to produce transgenic mice.

Transgenic mice are produced using modifications of procedures described by (Hogan et al., Manipulating the Mouse Embryo. Cold Spring Harbor, N.Y.: Cold Spring Harbor Laboratory Press; 1986). Glass needles for microinjection are prepared using a micropipet puller and microforge. Injections are performed using a Nikon microscope with Hoffman Modulation Contrast optics, with Narashigi micromanipulators and a pico-injector driven by $N_2$ (Narashigi).

Fertilized mouse embryos are surgically removed from the oviducts of superovulated female mice and placed into M2 medium. Cumulus cells are removed from the embryos with hyaluronidase at 300 µg/ml. The embryos are then rinsed in fresh M2 medium, and transferred into M16 medium for storage at 37° C. prior to injection. After injecting the DNA solution into the male pronucleus, embryos are implanted into avertin-anesthetized recipient females made pseudo-pregnant by mating with vasectomized males. Embryos are allowed to develop to term, and the newborn mice are analyzed for the presence of the transgene as described below.

Example 5

Analysis of Transgene Expression

Expression Analysis of Thy1.2-Gαq Transgenic Lines

To determine the levels and sites of expression of the mutant Gαq transgene in the rat, an RNase protection assay capable of detecting both transgene-derived Gαq and endogenous rat Gαq was done on brain and peripheral tissues including liver, kidney, spleen and heart for each of the Thy1.2-Gαq transgenic lines. A 221 bp fragment of mouse Gαq cDNA was amplified by PCR using primers DH10 and DH15 that encompasses the Gαq EE epitope tag as well as the G188S mutation. The 221 bp product by cloned into vector pGemT (Promega) to yield plasmid 1015/GemT and was verified by DNA sequence analysis. Plasmid 1015/GemT was linearized with NcoI on the 5' end of the insert in the polylinker of the pGemT vector and was used as a template for riboprobe synthesis. The riboprobes were synthesized using an in vitro transcription kit (Promega) and the protocols as described by the vendor. The 319 base riboprobe (221 bases Gαq plus 98 bases polylinker sequence) was synthesized in 1× transcription buffer containing 10 mM DTT, 0.05 mM each GTP, ATP, CTP, 10 µM $^{32}$P-labeled UTP (Amersham; 600 Ci/mmol activity), 1 µg Nco I linearized 1015/GemT and 5 units of SP6 RNA polymerase for 1 h at 37° C. followed by treatment with RQ1 DNAse for 30 min at 37° C. Labeled RNA was separated over a G50 spin column (Boehringer Mannheim, Indianapolis, Ind.) and the eluate was counted by liquid scintillation.

The RNAse protection assay was done as previously described (Howland et al., Neurobiol. Aging. 1995, 16: 685-699) using RNAse A/T1 mix. Total RNA was isolated using Trizol (Life Technologies) from whole brain or heart, liver, kidney, thymus as previously described (Howland et al. supra. The products of the RPA were electrophoresed on a 5% polyacrylamide/8M urea gel followed by exposure overnight to X-ray film (Kodak). Quantitation of transgene Gαq and endogenous Gαq bands was done using a Storm phosphoimager (Molecular Dynamics). For comparison, transgenic rats harboring the mutant Gαq cDNA driven by the neuron-specific rat synapsin I promoter (Howland et al., supra) was also analyzed in the RPA assay.

Using RNAse protection, the expected 221 base protected product representing the transgene-derived Gαq mRNA was apparent in all Thy1.2-Gαq transgenic brain samples.

Smaller molecular weight products of 80 to 120 bases represent protection of the endogenous mouse Gαq mRNA. For comparison, transgenic rats harboring the mutant Gαq cDNA driven by the neuron-specific rat synapsin I promoter (Howland et al., supra was also analyzed in the RPA assay. In each case, expression of the mutant Gαq RNA driven from the mouse Thy1.2 promoter was more robust than that seen from any of the Syn-Gαq transgenic lines. The 221 base protected Gαq transgene RNA product was not apparent in any surveyed tissue outside of the brain confirming that expression of the Thy1.2 minigene cassette is restricted to the CNS and PNS (Caroni, P. 1997. Overexpression of growth-associated proteins in the neurons of adult transgenic mice. J. Neurosci. Methods, 71 (1): 3-9). Quantitation of Gαq transgene expression in brain indicates that lines 67, 76 and 77 express higher levels than endogenous rat Gαq mRNA in brain. Lines 58 and 75 express comparable levels, while lines 11 and 70 express lower levels of transgene Gαq mRNA relative to endogenous Gαq in the brain.

Immunoblot of Gαq Protein Expression

Rats were euthanized with $CO_2$ and decapitated. The brains were then removed and frozen directly on dry ice. For Western blot analysis, one-half brain per animal was homogenized in 5 ml 1×RIPA solution (50 mM Tris-HCl, 150 mM NaCl, 2 mM $Na_2$EDTA, 1% Triton X-100 (x-octylphenoxypolyethoxyethanol), 0.25% sodium deoxycholate, 0.1% SDS, 1 mM benzamidine (Sigma), 0.05 mM leupeptin (Sigma), 0.02 mM pepstatin A (Sigma). Extracts were centrifuged at 14,0000×g, and supernatants were removed and assayed for total protein concentration by the Bradford assay (Bradford, Anal. Biochem. 1976, 72: 248-254). Fifty mg total protein was electrophoresed on 8% SDS-polyacrylamide gels and blotted to nitrocellulose (Howland et al., supra). Filters were blocked overnight in TBS containing 5% non fat milk and then treated with either 1:1000 rabbit anti-Gαq/G11 antibody or 1:500 mouse anti-EE antibody (Berldey Antibody Co.) for 4 h at room temperature. Following serial washes with TBS containing 0.05% Tween 20 (polyoxyethylene sorbitan monolaurate, blots were incubated with either goat anti-rabbit or goat anti-mouse IgG conjugated to horseradish peroxidase (BioRad; 1:2000) for 1 h. Following serial washes with TBS/0.05% Tween 20, filters were treated with ECL reagent (Amersham) and exposed to X-ray film to visualize the bands.

Detection of the protein product of the transgene was determined using anti-EE antisera to detect a strongly immunoreactive signal from each of the transgenic brain samples. A polyclonal antibody which recognizes both Gαq and G11 by Western blots was used to also detect mutant Gαq expression in the Thy1.2-Gαq transgenic rat brains. Brain extracts from the Thy1.2-Gαq transgenics show overexpression of Gαq protein when compared to nontransgenic (SD) brain samples. Highest levels of mutant Gαq protein were detected in brains from Thy1.2-Gαq line 5, 67 and 76, which is in accordance with the high mRNA levels as determined by RNase protection assay. These data indicate that Gαq driven from the Thy1.2 promoter is capable of overexpressing normal endogenous levels of Gαq in brain.

In situ Analysis

To localize transgene Gαq RNA expression in the subregions of the rat brain, in situ hybridization analysis was done using Thy1.2-Gαq G188S lines 11, 58, 67, 75 and 76. Animals were euthanized by $CO_2$ followed by decapitation and the brains were removed and frozen on dry ice and stored at −70° C. Brain sections were cut in the coronal plane on a Bright model OTF cryostat. In situ hybridization was performed essentially as previously described (Lewis et al., Biochem. Biophys. Res. Comm. 1993, 196:553-60) Mounted sections were treated with paraformaldehyde for 1 h at 25° C. Sections were washed 5 times in 2×SSC followed by incubation in 0.5 µg per ml proteinase K at 37° C. for 1 h. After a 1 min wash in water, sections were acetylated with 0.25% acetic anhydride in 0.1 M triethanolamine for 10 min and then washed with water for 5 min. Sections were then dehydrated through graded alcohols. The 1015/GemT riboprobe, as described above, was labeled using $^{33}$P-UTP (>1000 Ci/mmol, NEN) and 15,000,000 cpms were added per slide and hybridized in 50% formamide hybridization buffer at 52° C. overnight. The following day, coverslips were removed in 2×SSC and washed 5 times. Slides were incubated in RNAse A (Ambion) for 30 min at 37° C. and then rinsed in 2×SSC. Following washes in 1×, 0.5×, and 0.1×SSC at room temperature, slides were washed in 0.1× SSC at 70° C. for 1 h. Slides were then washed in 0.1×SSC at room temperature for 5 min followed by a water wash for 5 min. After dehydration through graded alcohols. Slides were air dried and exposed to X-ray film (Kodak) overnight.

To further localize transgene Gαq mRNA expression within subregions of the rat brain, in situ hybridization analysis was performed using Thy1.2-Gαq G188S rat lines. These lines (11, 58, 67, 75 and 76) demonstrated a range of mRNA expression levels in brain as shown by RNAse protection analysis. It has been previously documented (Caroni, 71 (1): 3-9) that the integration site of the Thy1.2 transgene can affect the pattern of transgene expression in the brain. These reported data indicate that certain brain regions (i.e., hippocampus, cortex, and amygdala) consistently exhibit Thy1.2-transgene expression across all lines. However, other regions including the striatum and hypothalamus exhibit variability in expression across transgenic lines carrying the Thy1.2 expression cassette. In situ hybridization studies with the Thy1.2-Gαq transgenic brains has confirmed the findings of Caroni (1997) in terms of expression pattern differences. Thy1.2-Gαq lines 11 and 76, demonstrated similar expression patterns. These two lines exhibited the most pan-neuronal expression patterns of all the lines analyzed. In particular, transgene expression in these lines was evident in the hypothalamus as well as the striatum. Expression patterns were similar between lines 58 and 67. These two lines show an absence of transgene expression in the hypothalamus and striatum. Outside of these two areas however, distribution of transgene mRNA was similar to that observed for lines 11 and 76. Thy1.2-Gαq line 75 exhibited an expression pattern that was more intermediate to lines 11, 76 and lines 58, 67. Only very low levels of transgene mRNA were detectable in the striatum and hypothalamus of this line. A summary of the expression profile of mutant Gαq in Thy1.2-Gαq lines 11, 58, 67, 75, and 76 is shown in Table 2.

TABLE 2

Gαq RNA Localization in Thy1.2-Gaq Transgenic Rat Brains

|  | 58 | 67 | 11 | 75 | 76 |
|---|---|---|---|---|---|
| Cerebral cortex | ++ | ++++ | +++ | +++ | ++++ |
| Thalamus | + | ++++ | +++ | +++ | ++++ |
| Caudoputamen | − | − | ++ | + | + |
| Accumbens nu | − | − | ++ | + | + |
| Amygdala | ++ | +++ | + | +++ | ++++ |
| Hypothalamus |  |  |  |  |  |
| paraventricular nu | − | − | +++ | + | ++ |
| hypothalamic nu (VMH, VMHDM, VMHC) | − | − | ++ | + | ++ |
| arcuate nu | − | − | + | + | + |
| DMD | − | − | ++ | + | ++ |
| Hippocampus |  |  |  |  |  |
| CA1 pyramidal cells | ++ | ++++ | ++ | ++ | ++++ |
| CA2 pyramidal cells | ++ | ++++ | ++ | ++ | ++++ |
| CA3 pyramidal cells | ++ | ++++ | ++ | ++ | ++++ |
| dentate gyrus | + | +++ | + | + | +++ |
| Perinquductal gray | ++ | ++ | − | + | +++ |
| Red nu | +++ | − | + | + | ++ |
| Pontine nu | +++ | +++ | +++ | + | + |
| Cerebellum |  |  |  |  |  |
| Purkinje cells | + | ++ | ++ | + | +++ |
| Granule cells | + | ++ | ++ | + | +++ |
| Deep cerebellar | +++ | +++ | + | + | +++ |

Example 6

Characterization of Animal Behavior

Overview of Behavioral Testing Strategy

To assess the effect of the RGS insensitive G188S Gαq mutant transgene on behavior, the following assessments were conducted in the following order:

Open Field
Global Assessment
Body Weight
Feeding Studies
Startle and Prepulse Inhibition*
Contextual Fear/Auditory Cue Conditioning
Responsiveness to Shock
Locomotor Activity*
5-HT2A Headshakes
Pilocarpine Cholinergic Signs**

*Prepulse inhibition was re-evaluated in a second cohort of Lines 58 and 75 followed by locomotor activity assessments.
**Pilocarpine cholinergic signs was conducted in females from lines 67, 76, and 11 only.

Animals—General

In general, 10 male and 10 female heterozygotes of each line were compared with a similar number of wild-type littermate controls. Testing began at 7-8 weeks of age. Subjects were individually housed in hanging metal mesh cages with ad libitum access to food and water under a 12 h light/dark cycle. For Lines 76, 67, and 11 the subjects were maintained on powdered rodent chow for the duration of the study. Subjects from Lines 58 and 75 were adapted to powdered chow for the feeding studies and then maintained on that chow for the remainder of the study. Subjects were evaluated in a series of tests outlined below over a period of approximately 12 weeks.

For acute lithium studies, male Sprague-Dawley rats (250-300 g, Charles River) were used. Rats were treated acutely with LiCl (3-10 mEq/kg i.p.) or vehicle (saline) 20-24 h prior to behavioral or pharmacological assessment by the methods described below. Animals were group housed in the locomotor and prepulse inhibition studies and singly housed for studies investigating open field behavior, feeding and DOI or pilocarpine-induced behaviors.

For chronic lithium studies, male Sprague-Dawley rats (23 days of age on arrival, Charles River) were used. Following 1 week acclimation, these subjects were housed in groups of 5 and fed standard grain-based rodent diet or diet containing LiCl (1.7 g/kg) beginning at 29 days of age. Food and water were available ad libitum and body weights were measured at least twice weekly. At 45 days of age, the regular diet group was divided in half. One half continued on regular diet ad libitum (ad-lib), while the other half was fed a restricted amount of regular diet daily to reduce body weights to a level equivalent to the lithium-fed group (pair-fed). Subjects were individually housed at 47 days of age. Behavioral testing began in these subjects at approximately 8 weeks of age (after 4 weeks of lithium diet) and followed a schedule of testing similar to the transgenic rats (see below) while continuing feeding on either the regular diet (ad-lib or pair-fed) or lithium diet. Behavioral testing was interrupted after locomotor studies. At 17 weeks of age (13 weeks of 1.7 g/kg Li diet), the concentration of LiCl was increased to 2.2 g/kg and saline (0.9%) was provided. DOI headshake studies and pilocarpine studies were conducted between 20 and 24 weeks of age. A separate group of male rats (young adult 200-250 g) were exposed to LiCl diet (4.3 g/kg). Prepulse inhibition studies and locmotor activity studies were conducted between 6 and 8 weeks of exposure.

Global Behavior Assessment

A schedule of behavioral testing was arranged to determine the phenotype of heterozygous versus wild type littermate controls. These tests evaluated animals for a number of behaviors to assess any visual/obvious effects due to transgene expression.

Subjects were weighed and transferred from their home cages to a rack of metal hanging cages in groups of 10. The rack was then moved to an observation room, and the subjects given an acclimation period. An observer, blind to the genetic identity of the subject, evaluated each subject once every 15 min for an hour following the acclimation period. A checklist of behaviors, reflexes and autonomic signs (see Table 3 for summary) was marked for presence of each sign. (See Crawley et al., 1998).

Figure 3B:
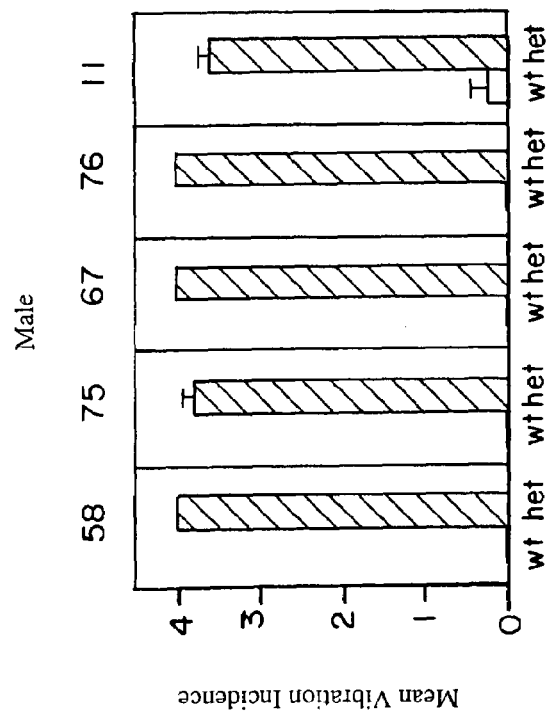

Only "tremors" appeared consistently and in the majority or all of the transgenic positive rats. This behavior was described by the observer as a "vibration" upon handling and increased involuntary movement of the lower extremities when an animal was held around the torso, and the lower extremities were suspended (FIG. 3, A and B).

Observations of the rats were made after approximately 4 weeks on the 1.7 g/kg lithium diet. Only "tremors" appeared consistently and in the majority of rats. The observer described this behavior as a "vibration" upon handling and restraint (Table 3).

TABLE 3

Global Assessment of Behavior: Detection of Vibration Induced by Chronic Exposure to LiCl

|  | Ad Lib Regular Diet | Pair Fed Regular Diet | LiCl Diet |
|---|---|---|---|
| N | 10 | 10 | 10 |
| % Subjects Showing Vibration | 0 | 30 | 90 |
| Mean (+/− sem) Incidence of Vibration (max score = 4) | 0 | 0.5 +/− 0.3 | 2.4 +/− 0.5 |

Body Weight

Measurements were recorded across a number of time points and behavioral assays. Body weight was measured at toe clip (Day 6; lines 67, 76, and 11), weaning (Day 21; lines 67 and 76), at the time of the global evaluation (6-8 weeks; all lines), food intake studies (9-10 weeks; all lines), and prepulse inhibition studies (11-12 weeks; all lines). Repeated measures ANOVA and post hoc comparisons using least squares determined statistical significance.

Figure 4B:
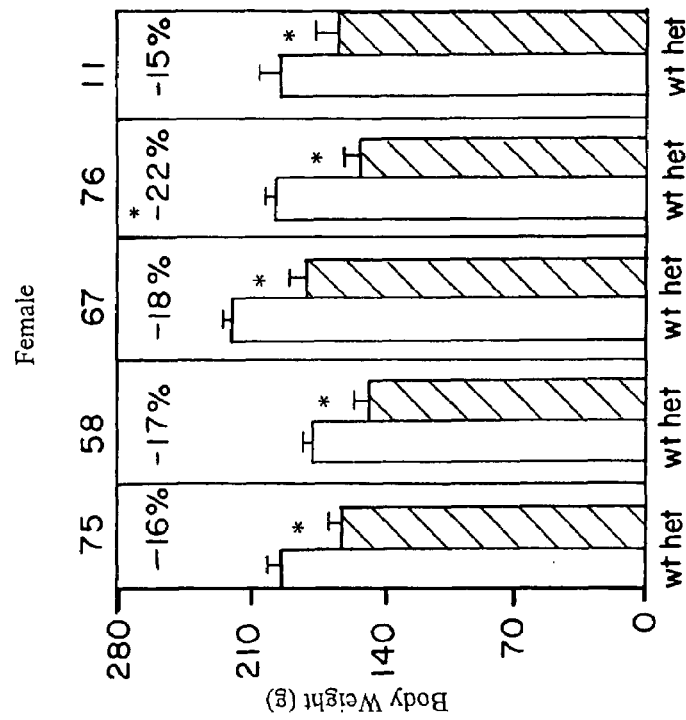
FIG. 4 (A and B) shows body weight effects in male (A) and female (B) Gq transgenic rats.
Figure 4A:
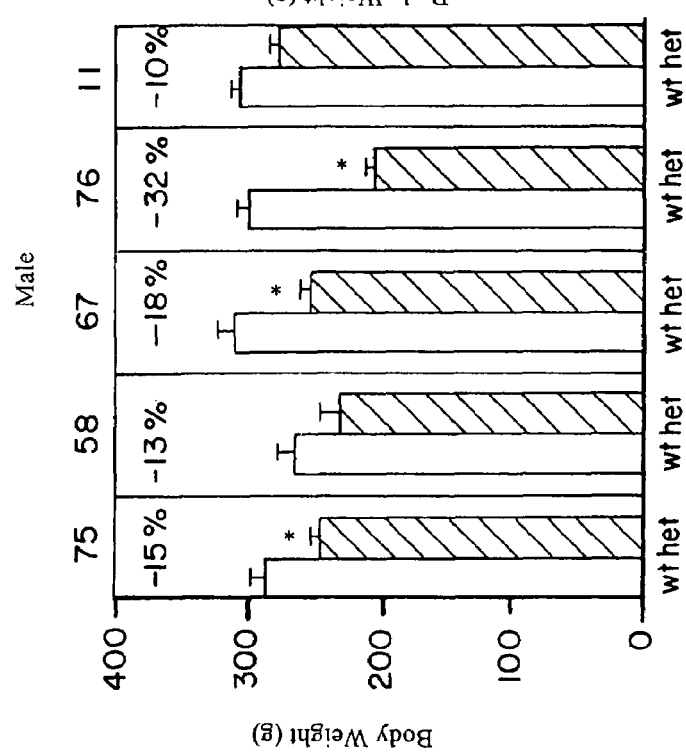

In general, rats expressing the transgene were observed to be somewhat smaller than littermate controls. To assess this more accurately, body weight measurements were obtained at various times, as noted previously. For rat lines 58 and 75, (with the exception of line 58 males), the body weight difference was statistically significant (P<0.05) at the earliest time point measured (6-7 weeks). For rat line 58 males, a significant difference in weight was observed later, between weeks 8 and 9. For rat lines 67 and 76, transgenically negative males from both lines 67 and line 76 showed a similar growth curve. Line 67 and line 76 male +/− rats weighed significantly less than the −/− rats, with an apparently greater effect in line 76. Although there were no differences at day 6, by day 21 there were statistically significant differences between the groups (data not shown). A similar effect occurred in line 67, 76, and 11 females, with significant differences occurring by week 7-8 (FIG. 4). The plateau that occurs in all of the growth curves coincides with food intake studies in which animals were fasted for 24 h 3 times over a 2 week period and the animals were treated with a 5-HT$_{2c}$ receptor agonist.

Rats were maintained on a lithium (LiCl) diet (1.7 g/kg) starting at 29 days of age. Rats maintained on the chronic lithium diet weighed 20-30% less than those maintained on grain-based chow (FIG. 5).

Food Intake

Figure 6B:
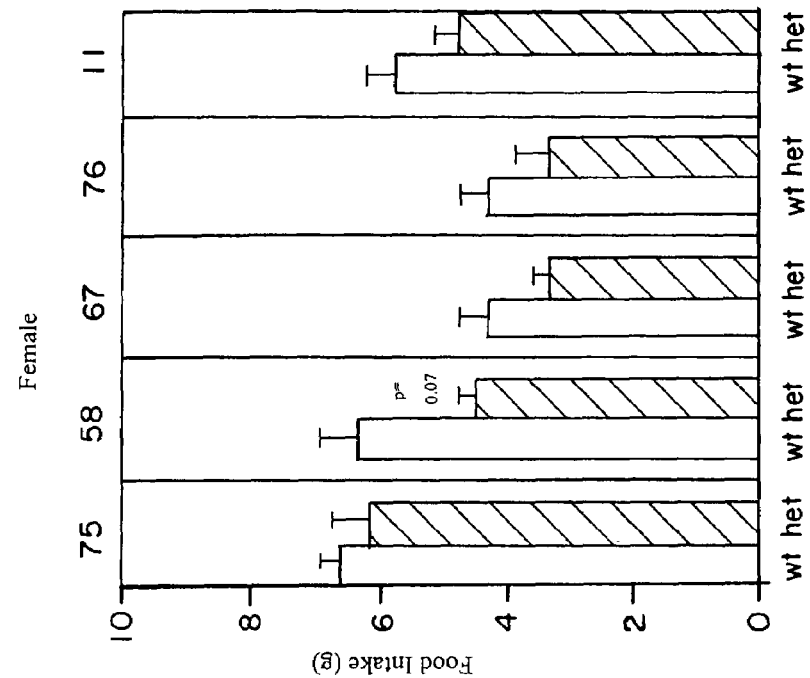
FIG. 6 (A and B) shows effects on food intake in vehicle treated male (A) and female (B) Gq transgenic rats.
Figure 6A:
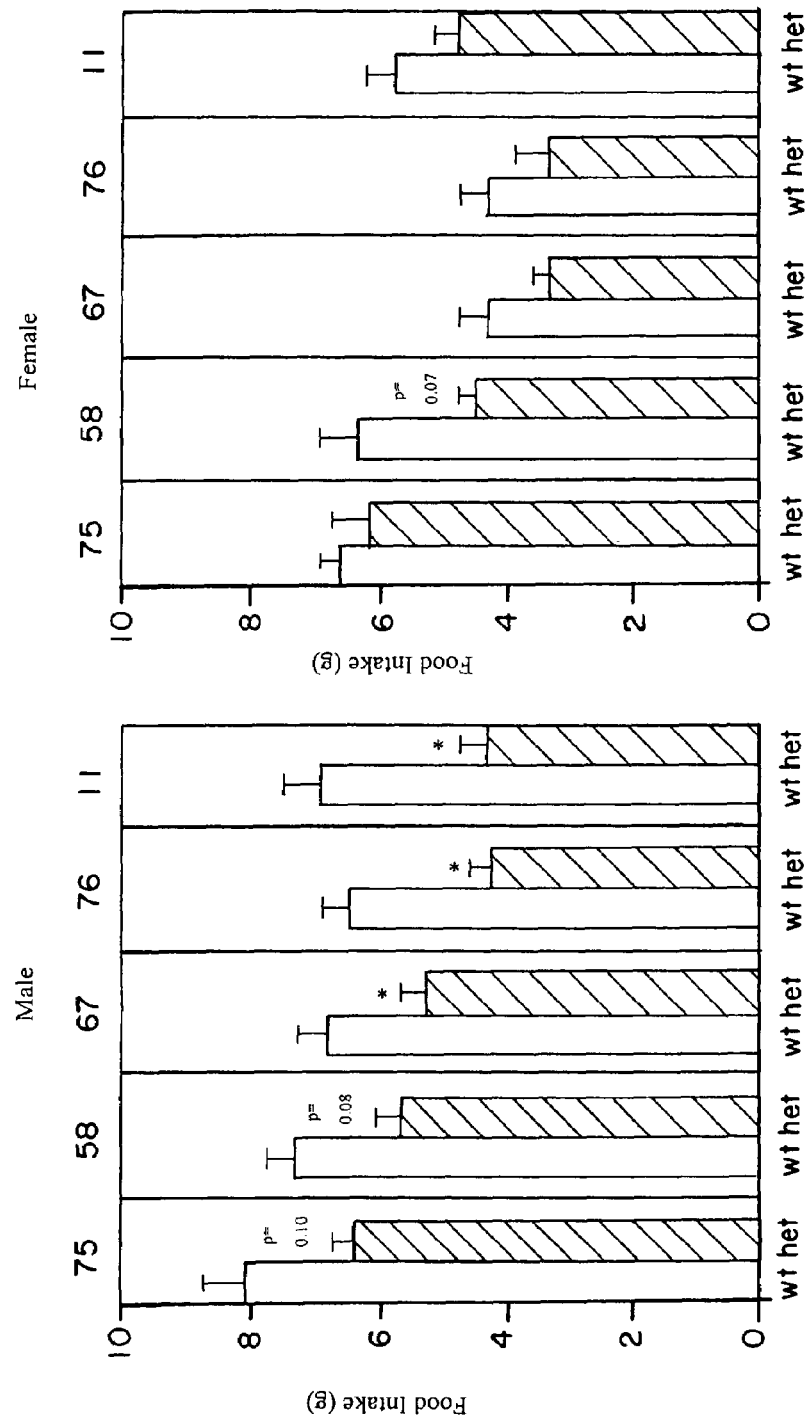

Wild-type and transgenic rats were maintained on powdered chow in their home cages. Rats were fasted for 24 h prior to evaluation of food intake. Food intake was measured at 2, 4, and 24 h timepoints following ip injection of vehicle, 1, or 1.7 mg/kg RO 60-0175. Experimental sessions were generally conducted on Tues and Fri with 24 h fasts initiating on Mon and Thurs. Repeated measures ANOVA and post hoc comparisons using least squares determined statistical significance. 5-HT2C agonists decrease food intake via a Gαq modulated pathway. Studies using the selective 5-HT2C agonist RO 60-0175 were conducted to determine if 5-HT2C agonist activity was modified in transgenic rats. The results are summarized in FIGS. 6 and 7. Food intake was reduced at 1 or more time points following vehicle administration in male and female transgenic heterozygotes of all lines with the exception of line 75 females, who did not show differences in food intake (2 hr timepoint shown in FIG. 6; other data not shown).

Figures 7A, 7B:
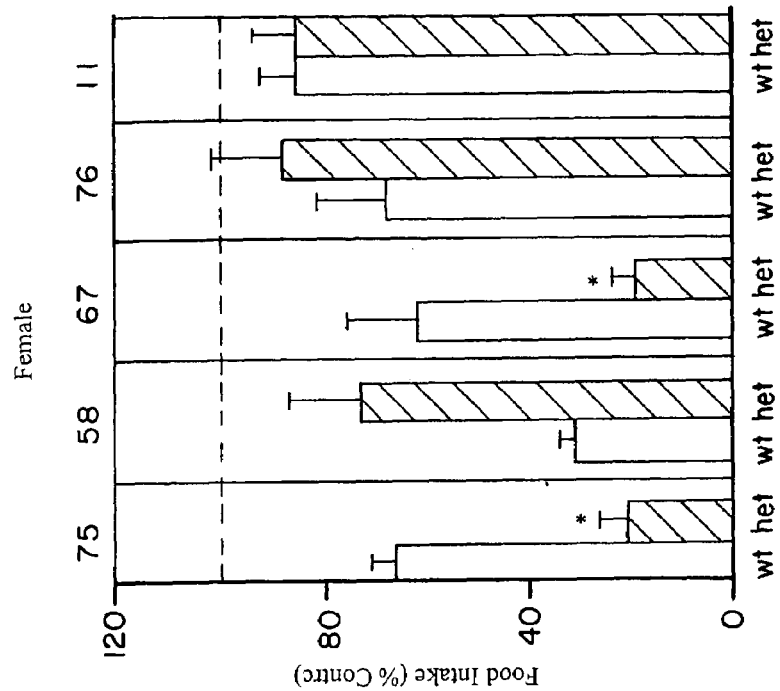
FIG. 7 (A and B) shows effects on food intake in 5-HT2C agonist treated male (A) and female (B) Gq transgenic rats.

To account for the baseline differences in food intake between wild-type and transgenic rats, the effects of RO 60-0175 were calculated as a percentage of the vehicle food intake. The effects of 1.7 mg/kg RO 60-0175 were greater in both males and females for transgenic heterozygotes for lines 75 and 67 (FIG. 7). The effects of 1.0 mg/kg RO 60-0175 were greater in males of line 67 as well (data not shown). However, in line 75 females, the effects of 1.0 mg/kg RO 60-0175 was greater in wildtype than in transgenic rats (data not shown). There was no change in the effects of RO 60-0175 in rats from lines 58, 76, or 11. These data indicate that 5-HT2C agonist effects that are mediated through Gαq can be potentiated in the presence of Gαq mutants that are not regulated by RGS proteins.

Figure 8A:
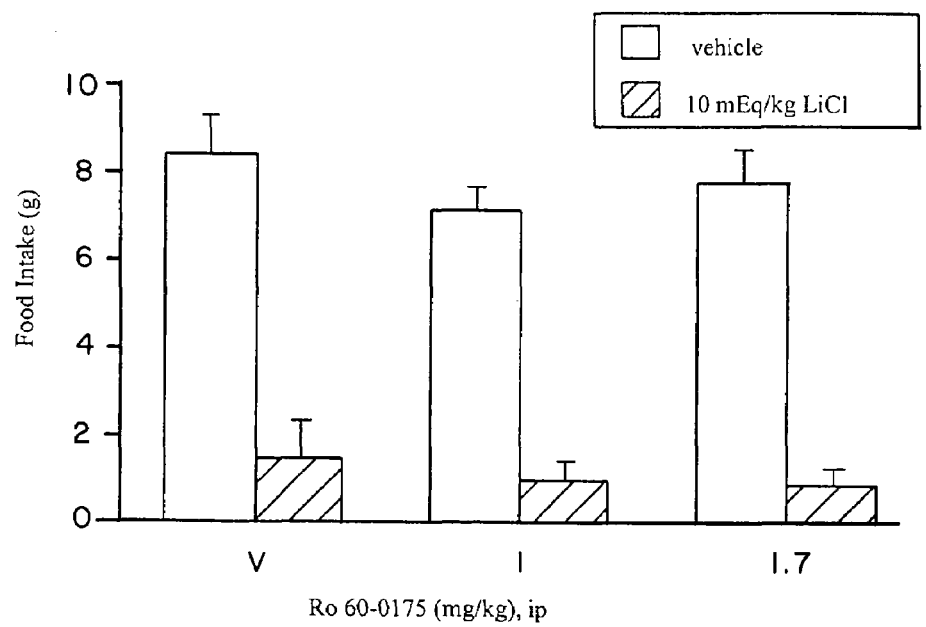
FIG. 8 (A and B) shows effects of acute lithium on food intake in vehicle and 5-HT2C agonist treated rats based on amount in grams, A) or percent control (B).
Figure 8B:
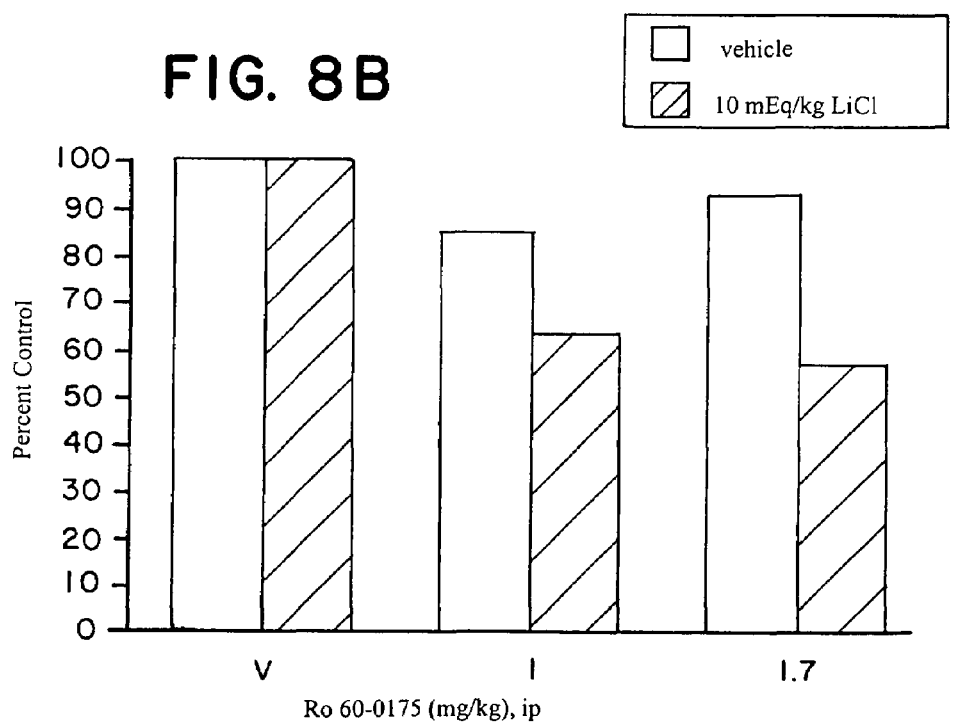

Two-hour food intake was markedly decreased following acute lithium administration in a separate group of rats. 5-HT2C agonists decrease food intake via a Gαq modulated pathway. Studies using the selective 5-HT2C agonist RO 60-0175 were conducted to determine if 5-HT2C agonist activity was modified by lithium. Due to the marked decreases in food intake produced by lithium, 5-HT2C agonist-induced decreases in food intake are difficult to interpret. Nonetheless, as a percent of baseline intake, RO 60-0175 produced a greater decrease in food intake in lithium treated animals (FIG. 8).

Figure 9:
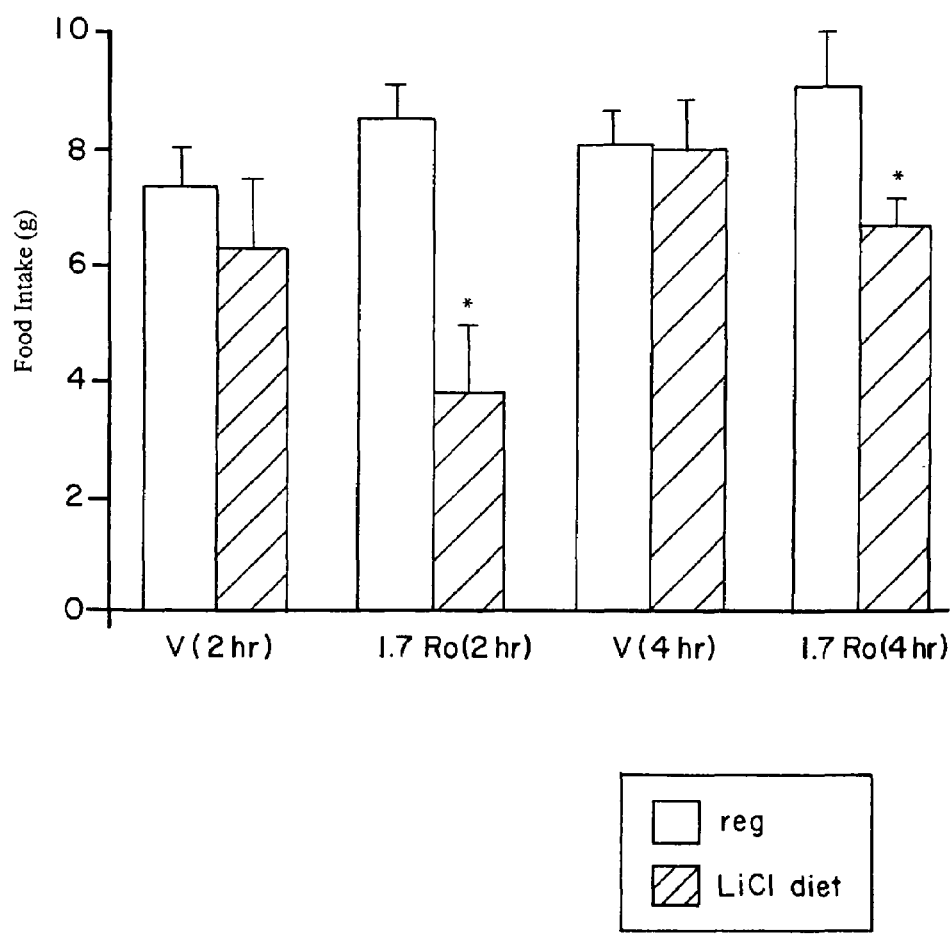
FIG. 9 shows effects of vehicle or 5-HT2C agonist on food intake in LiCl diet treated rats.

Two-hour food intake was not affected in animals maintained on the chronic lithium diet (FIG. 9). 5-HT2C agonists decrease food intake via a Gαq modulated pathway. Studies using the selective 5-HT2C agonist RO 60-0175 were conducted to determine if 5-HT2C agonist activity was modified by lithium. The effects of RO 60-0175 on food intake were potentiated in animals maintained on a lithium diet (FIG. 4).

Prepulse Inhibition and Startle

Subjects were weighed and transported from their home cages to the laboratory testing room. Acoustic startle habituation was evaluated in the morning, and prepulse inhibition was evaluated in the afternoon. Between testing, subjects were returned to their home cages. For acoustic startle habituation, each subject was placed inside a restrainer mounted on a platform inside the startle test chamber (San Diego Instruments, San Diego, Calif.). Movements of the subject were detected by a transducer connected to a digitizer and computer. Following a 5 min habituation period at a background noise level of 64 dB, a burst of white noise (120 dB, 20 ms) was delivered from a speaker mounted 12 in above the rat on a random interval 15 sec schedule. The movement of the subject in response to each startle stimulation was digitized over the 100 ms period following the onset of the burst and expressed in arbitrary startle units. Data were analyzed by LSD following 2-way ANOVA (transgene×trials) with one repeated measure (trials), with significance determined as p<0.05.

For prepulse inhibition testing, subjects were again placed in the restrainer inside the startle test chamber for a 5 min acclimation period at a background noise level of 64 dB. After the acclimation period, each subject was exposed to four types of acoustic stimuli: a startle stimulus (20 ms duration, 120 dB) and three different intensities of prepulse stimuli (20 ms duration; 69, 74 and 79 dB presented 100 ms (onset to onset) prior to the startle stimulus). A test session consisted of an initial startle stimulus followed by 15 sequences of the four stimulus types, presented in a pseudorandom order against a constant 64 dB white noise background. Intertrial intervals averaged 15 sec. Mean startle amplitude was determined by averaging 100 1 ms readings taken from the beginning of the stimulus. PPI was defined as 100-([startle amplitude on prepulse trials/startle amplitude on startle alone trials]×100) for each prepulse intensity. (Swerdlow et al., Ann. N.Y. Acad. Sci. 1999, 877:202-216). Data were analyzed by LSD following a 3-way ANOVA (transgene×gender ×prepulse intensity) with one repeated measure (prepulse intensity) for Lines 58 and 75, or following a 2-way ANOVA (transgene×prepulse intensity) with one repeated measure (prepulse intensity), with significance determined at p<0.05.

Acoustic startle habituation was evaluated in rat lines, along with an assessment of sensorimotor gating (prepulse inhibition of acoustic startle). Startle habituation is influenced by changes in serotonin neurotransmission (impaired by SSRIs, and LSD; accelerated by 5-HT2A antagonists). Prepulse inhibition (PPI) of acoustic startle response is an unlearned behavior where presentation of a weak stimulus immediately prior to a startle eliciting stimulus results in a dampening of the motor startle reflex response. PPI is disrupted in certain disease states such as schizophrenia, Huntington's disease and possibly OCD (Swerdlow et al., supra). It can be modeled in several species and is dependent on a basal ganglia circuitry and controlled by limbic cortical inputs. The 5-HT2A agonist DOI disrupts PPI and this effect is mediated by 5-HT2a receptors in the ventral pallidum.

Figure 10A:
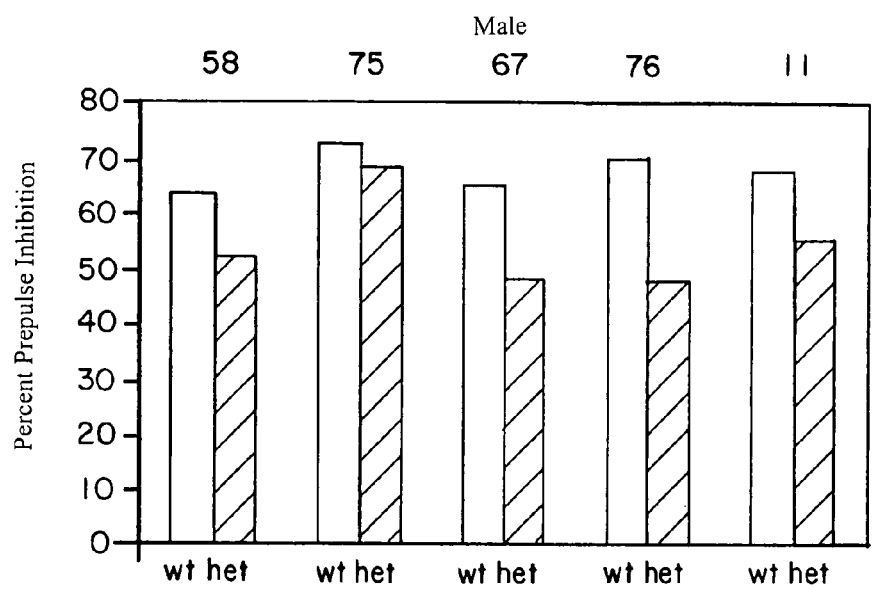
FIG. 10 (A and B) shows prepulse inhibition and acoustic startle studies in male (A) and female (B) Gq transgenic rats.
Figure 10B:
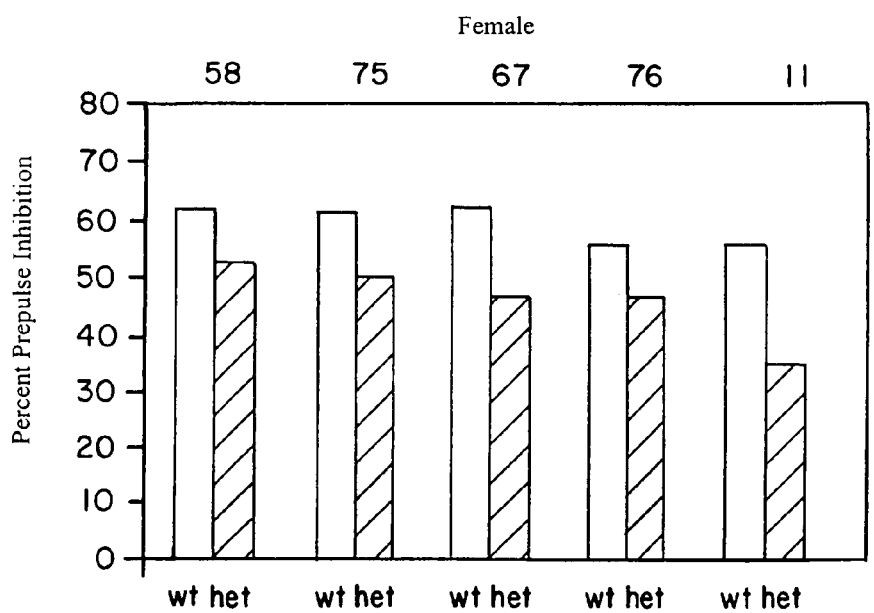

FIG. 10 summarizes the differences between heterozygotes vs wildtype littermate controls of each line for prepulse inhibition. Line 58 transgenic males, but not females, demonstrated a significant decrease (p<0.05) in startle habituation (data not shown). In line 67, the transgenic females demonstrated a significant decrease (p<0.05), while a decrease trend was noted for line 67 transgenic males for startle habituation (data not shown). No differences in startle habituation were observed for lines 75, 76, or 11 (data not shown). However, all lines demonstrated a transgenic effect on prepulse inhibition suggesting some commonality with other phenotypes appearing in all lines (decreased body weight, "vibration") (FIG. 10). Deficits in prepulse inhibition have been related to attentional deficits in certain neuropsychiatric disease states. These data reflect attentional deficits induced by the mutant transgene expression. The lines differ in their pattern of expression of the transgene in basal ganglia structures. Thus, there is a reduced likelihood that this phenotype is related to that brain region.

Acute lithium produced deficits did not affect acoustic startle. Lithium produced deficits in PPI at all stimulus intensities (FIG. 11).

Figure 12A:
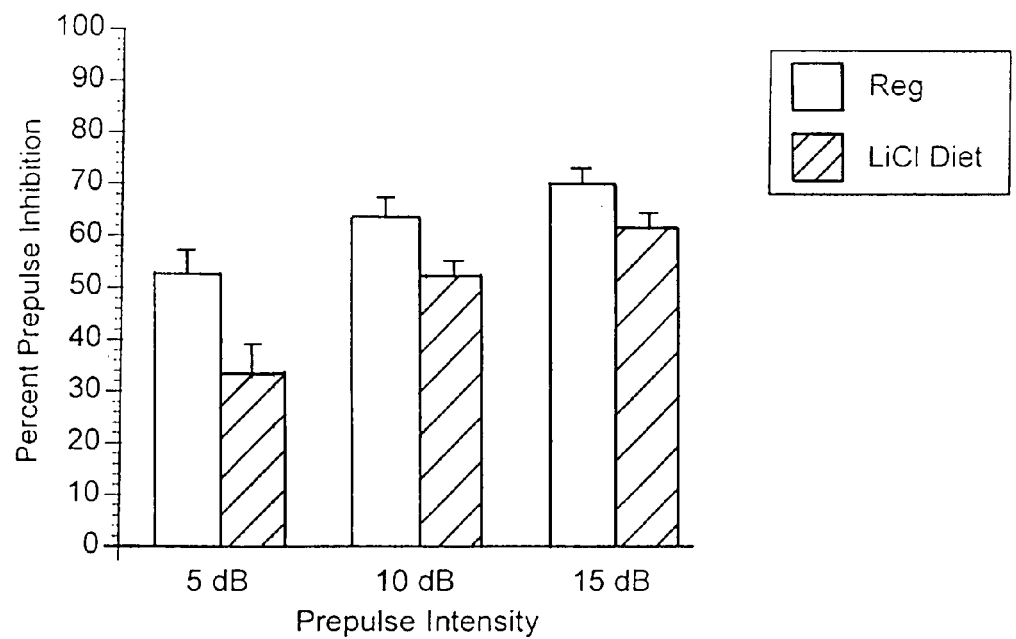
FIG. 12 (A and B) shows prepulse inhibition (A) and acoustic startle (B) studies in rats maintained on LiCl diet.
Figure 12B:
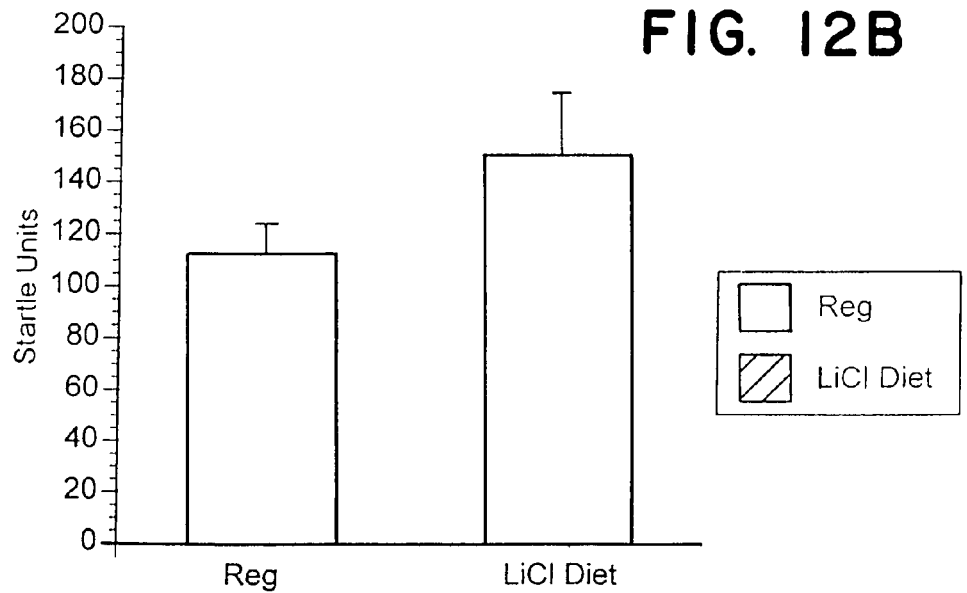

Exposure to high concentration LiCl diet (4.3 g/kg) for one week resulted in a decrease in prepulse inhibition (FIG. 12).

Contextual Fear and Auditory Cue Conditioning

Subjects were placed in a rectangular operant chamber and allowed to habituate for 2 min, following which a tone was presented for 20 sec. Immediately following the tone, a 1 mA scrambled shock was administered through a grid floor for 2 sec. The animals were removed from the chamber and returned to their home cages 30 sec after the termination of the shock. Approximately 15 h later animals were returned to the original test chambers (context), and the incidence of freezing at ten sec intervals was recorded for 5 min (maximum response =30). At the end of the 5 min test period animals were returned to their home cages. Approximately 60 min later, subjects were placed in a novel environment (new room, square chamber, plastic floor, red lights) and freezing was recorded for 5 min (novel). At the end of the 5 min period, the auditory tone was presented, and freezing behavior was recorded for 5 min (see Rudy and O'Reilly Behavior Neurosi. 1999,113:867-880; Pugh et al., Behavioral Neurosci. 1997,111:503-11, Anagnostaras et al., Neuropsychopharmacology 1999, 21:731-44).

Figure 13A:
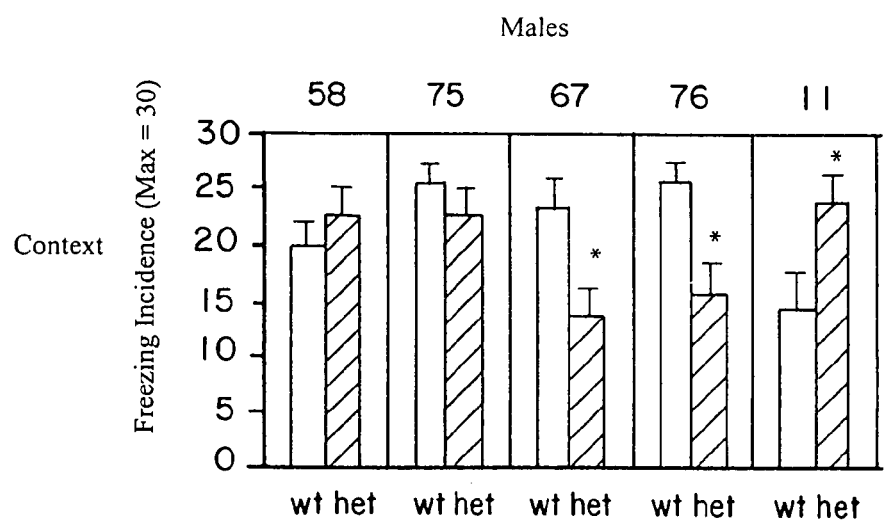
FIG. 13 (A-F) shows contextual fear conditioning and auditory cue conditioning in male (A-C) and female (D-F) Gq transgenic rats.
Figure 13B:
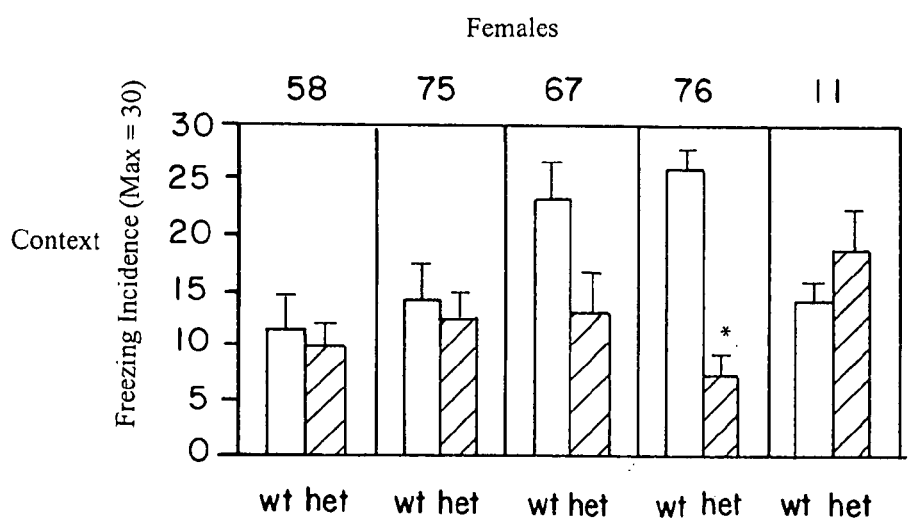
Figure 13C:
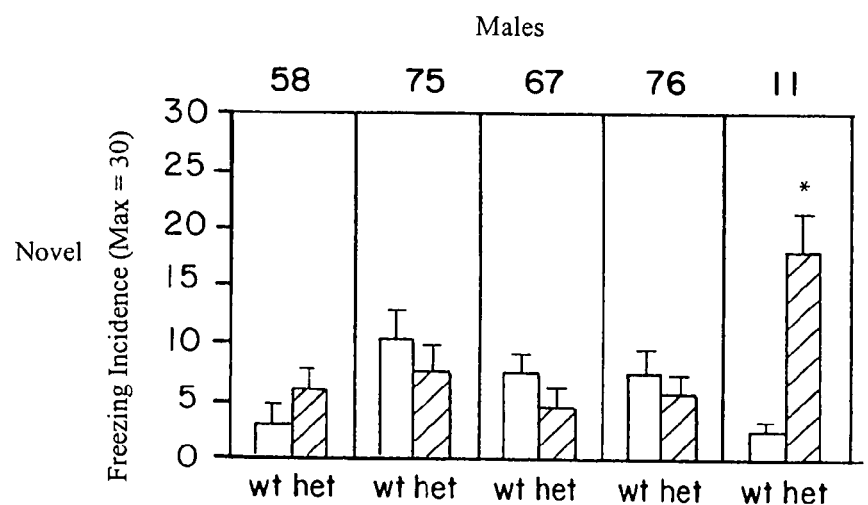
Figure 13D:
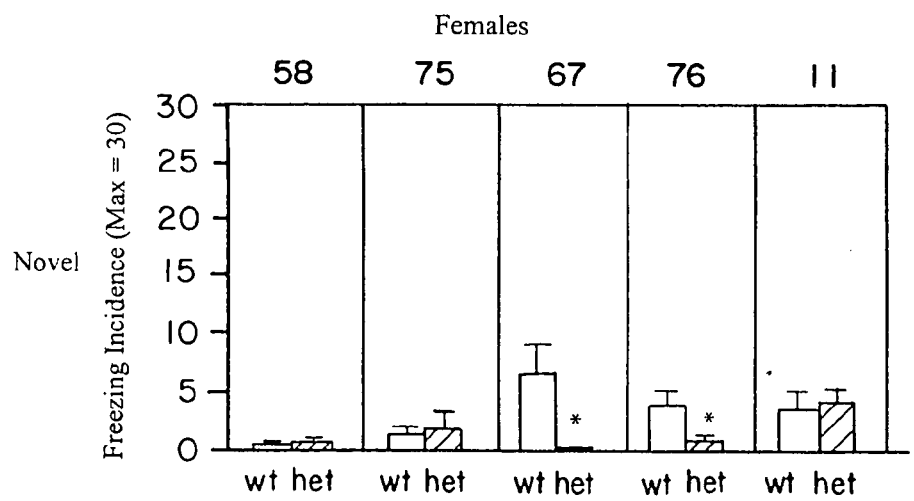
Figure 13E:
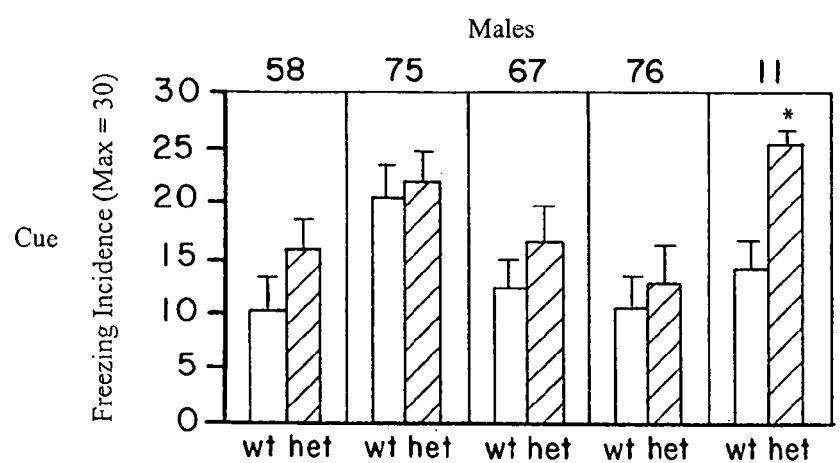
Figure 13F:
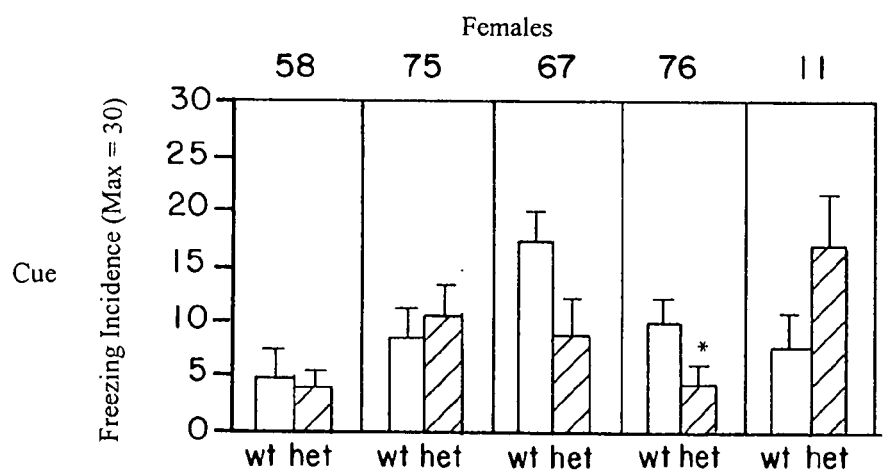
Figure 14A:
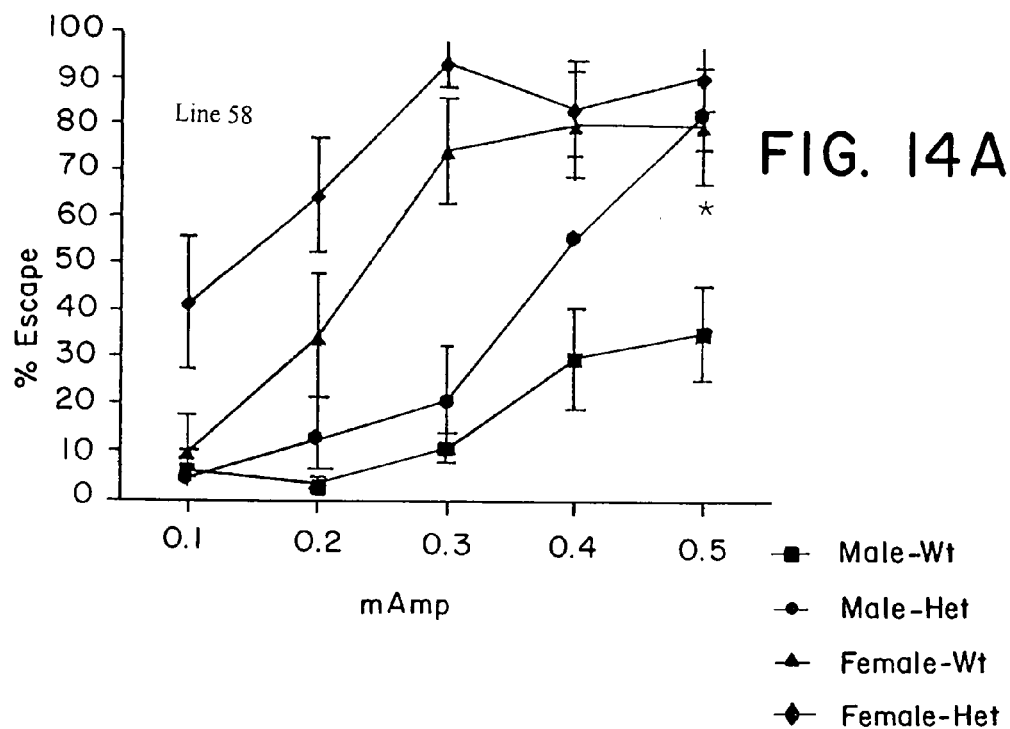
FIG. 14 (A-E) shows shock escape behavior in Gq transgenic rats.
Figure 14B:
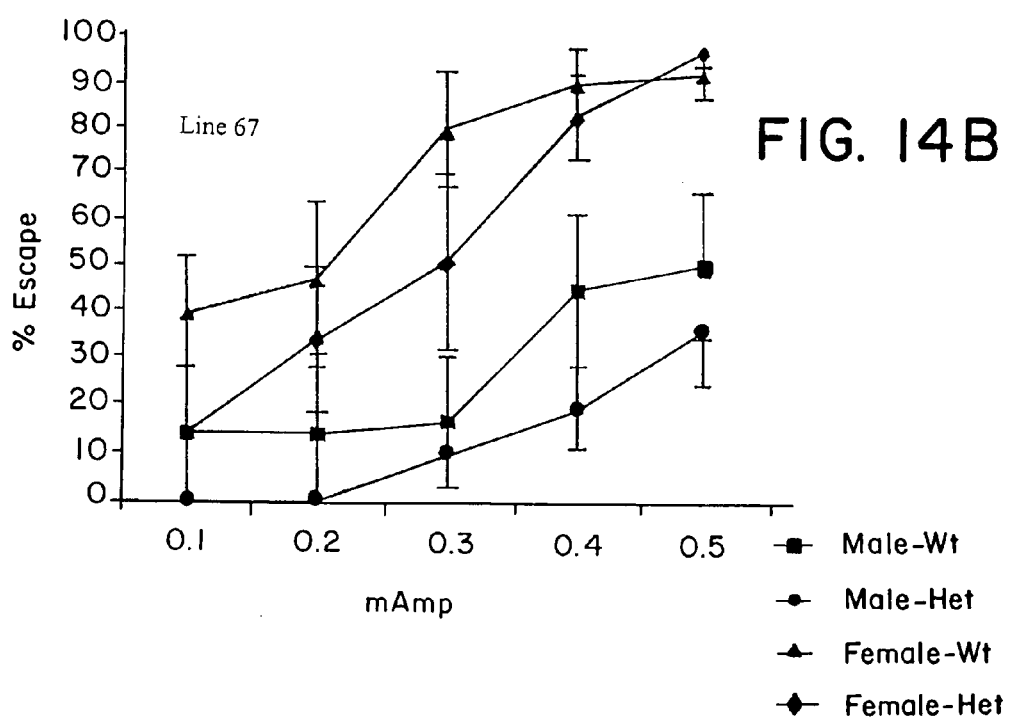
Figure 14C:
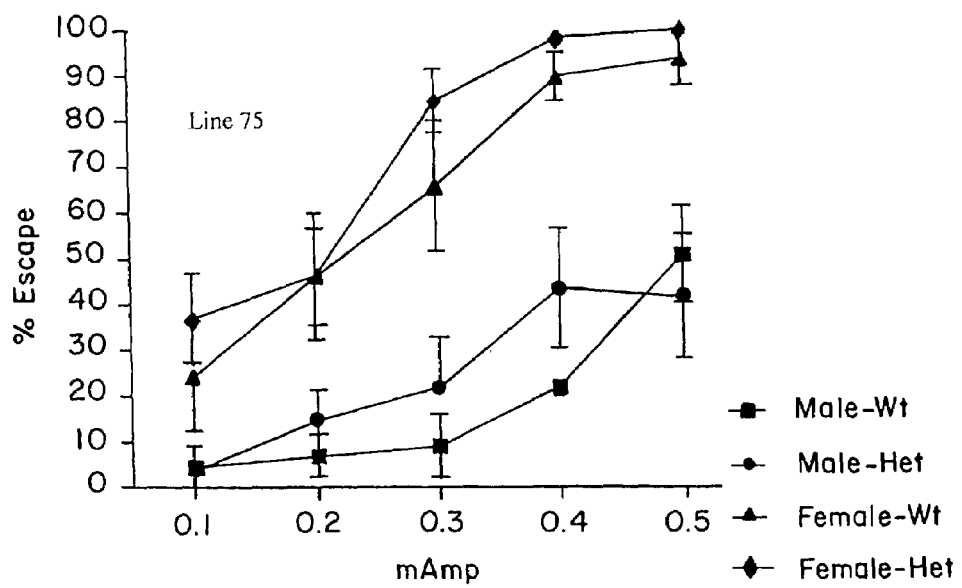
Figure 14D:
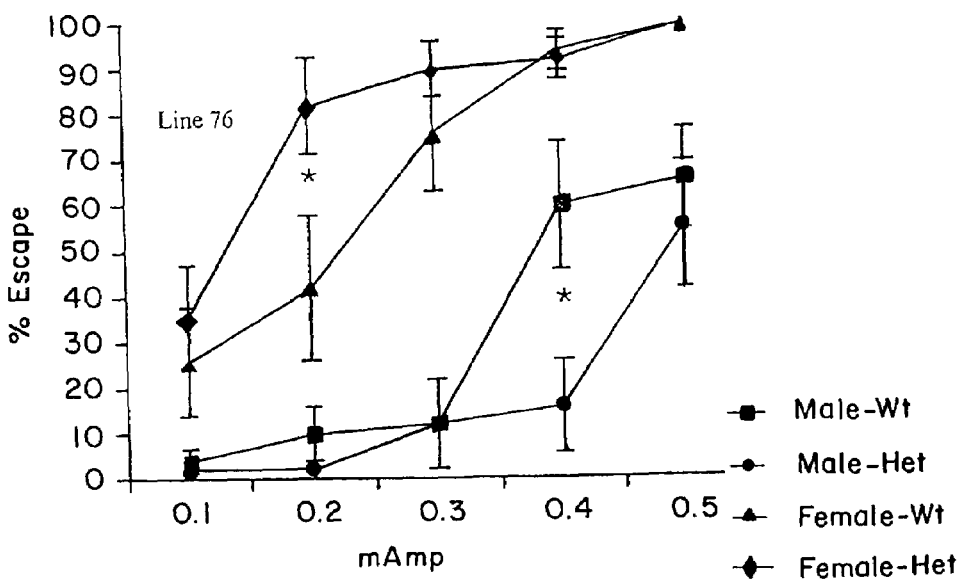
Figure 14E:
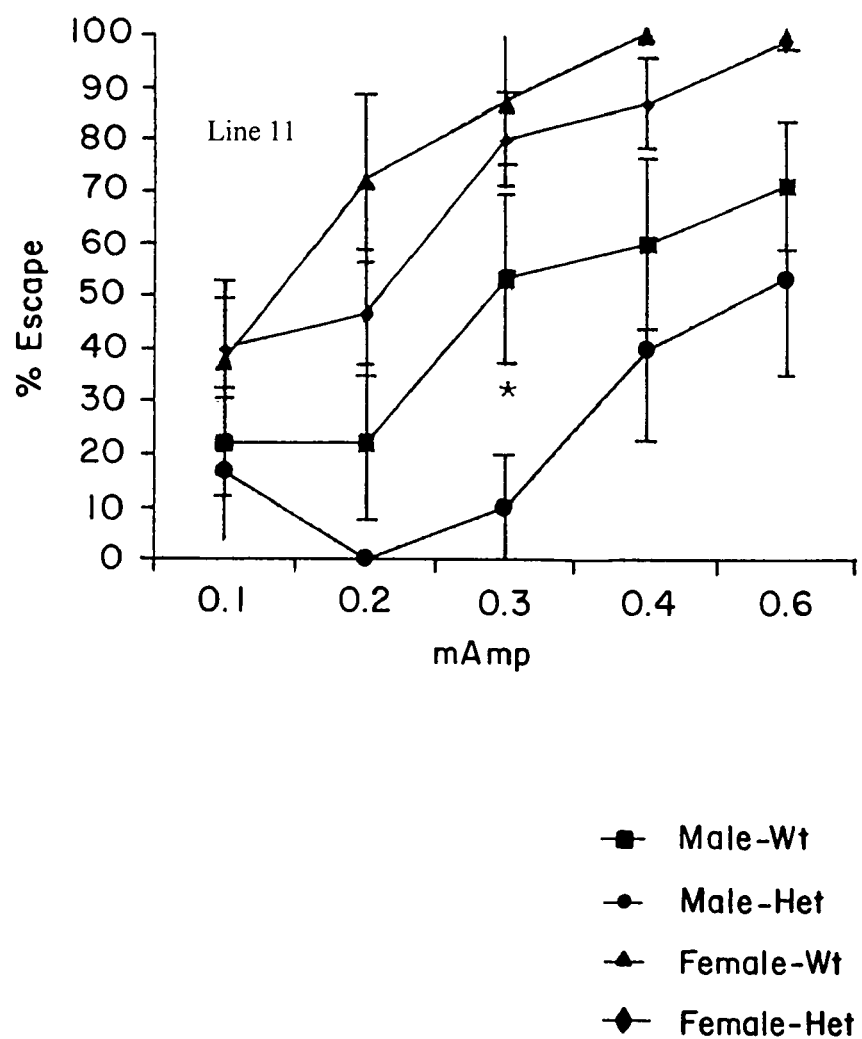
Figure 15A:
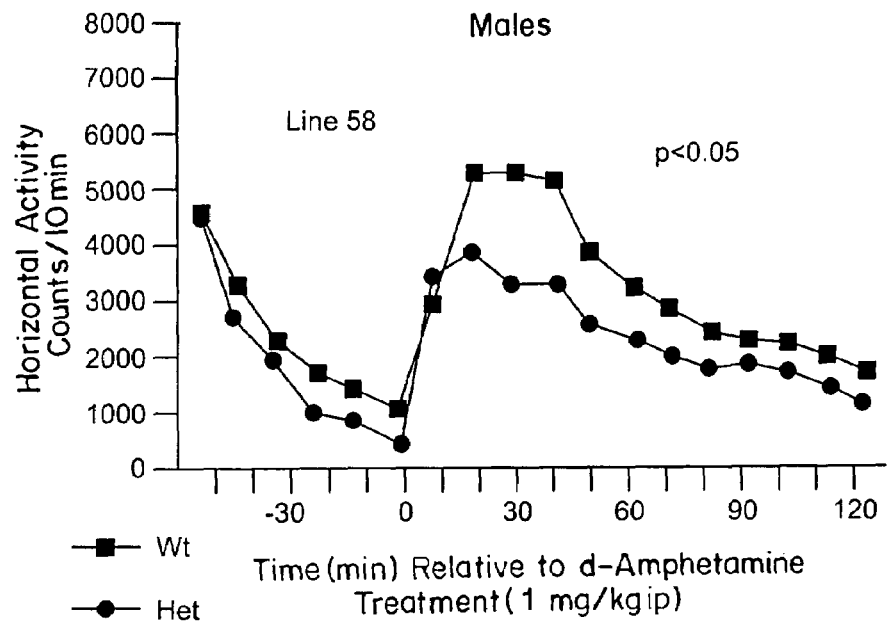
FIG. 15 (A-H) shows effects on d-amphetamine on locomotor activity in male (A-E) and female (F-H) Gq transgenic rats.
Figure 15B:
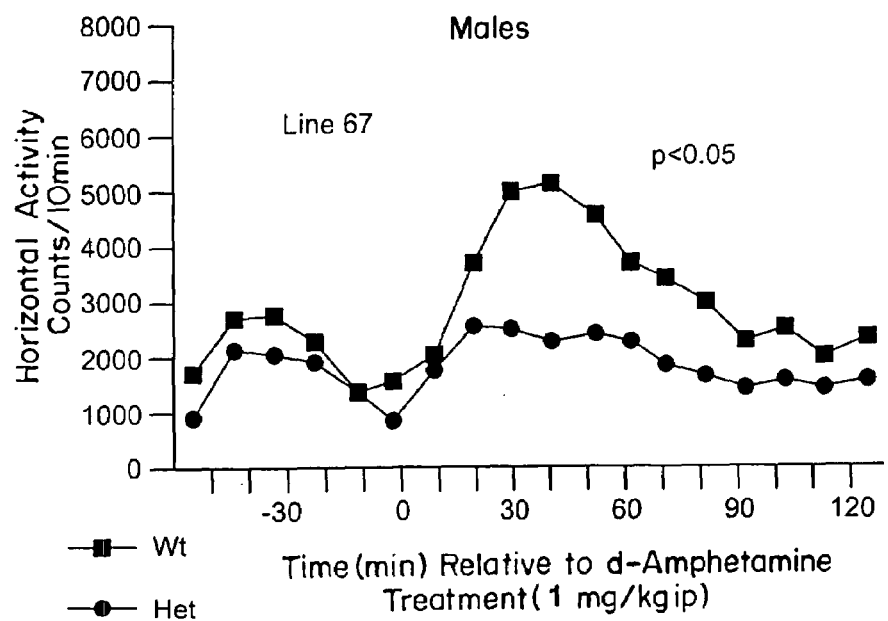
Figure 15C:
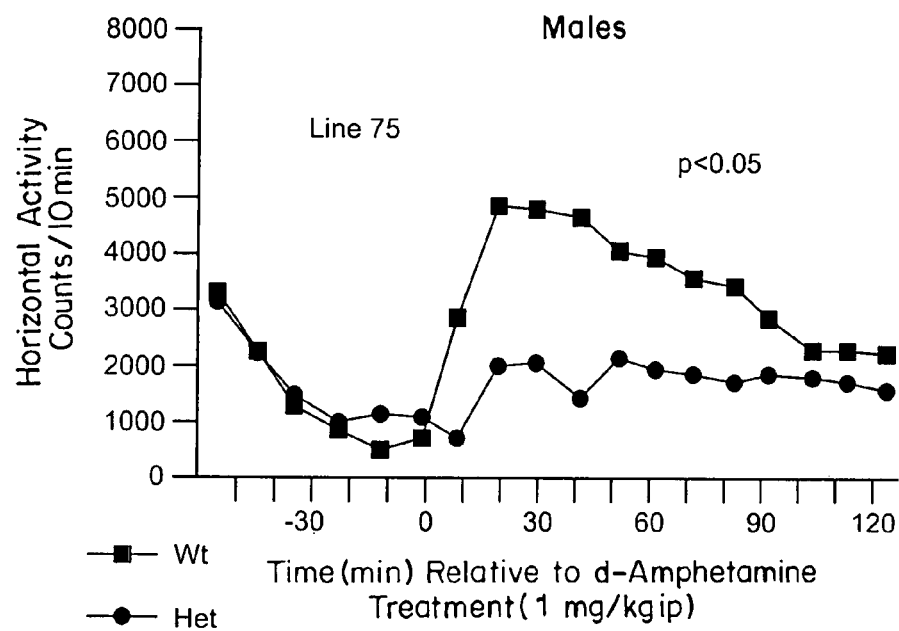
Figure 15D:
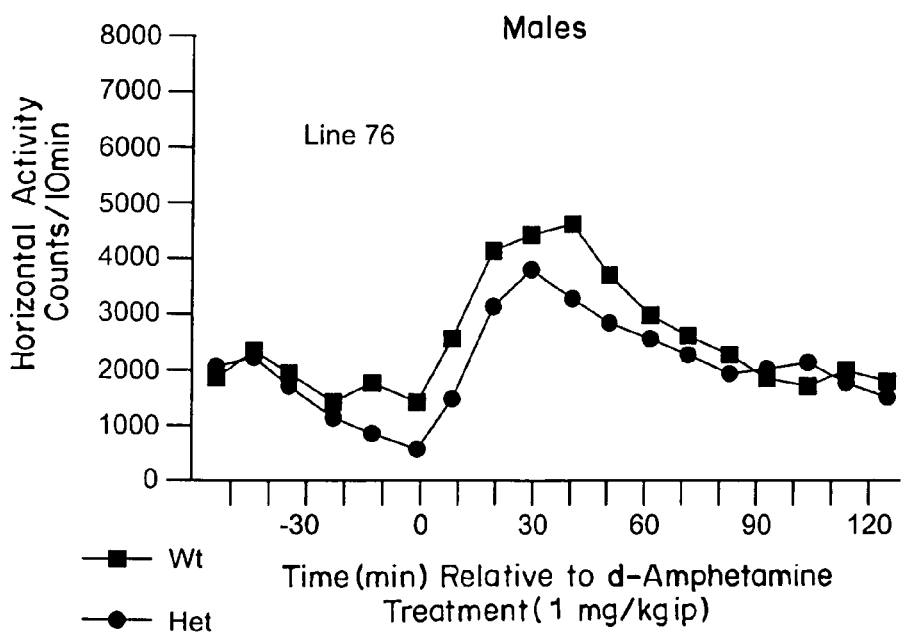
Figure 15E:
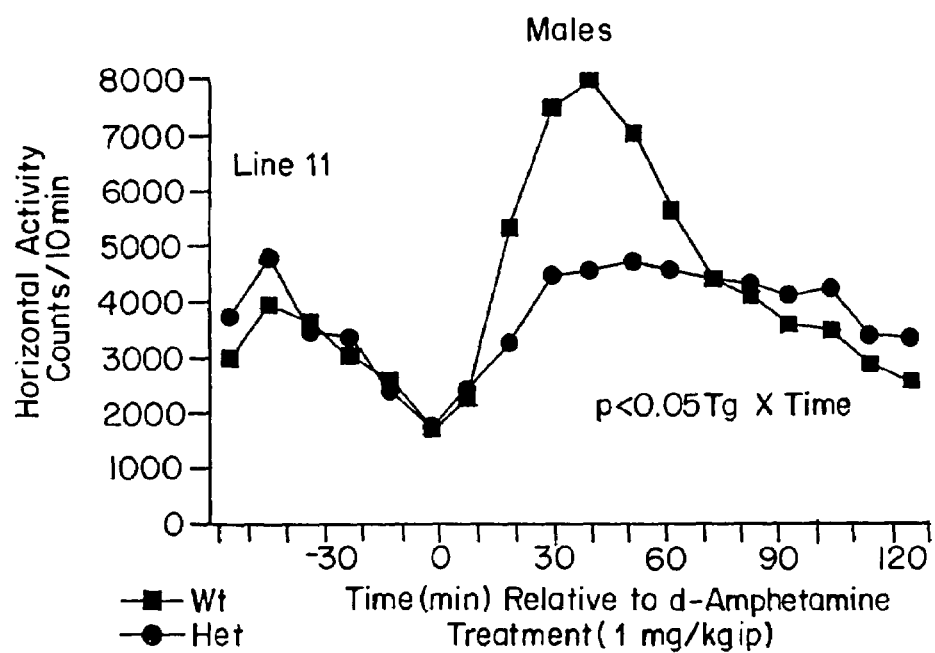
Figure 15F:
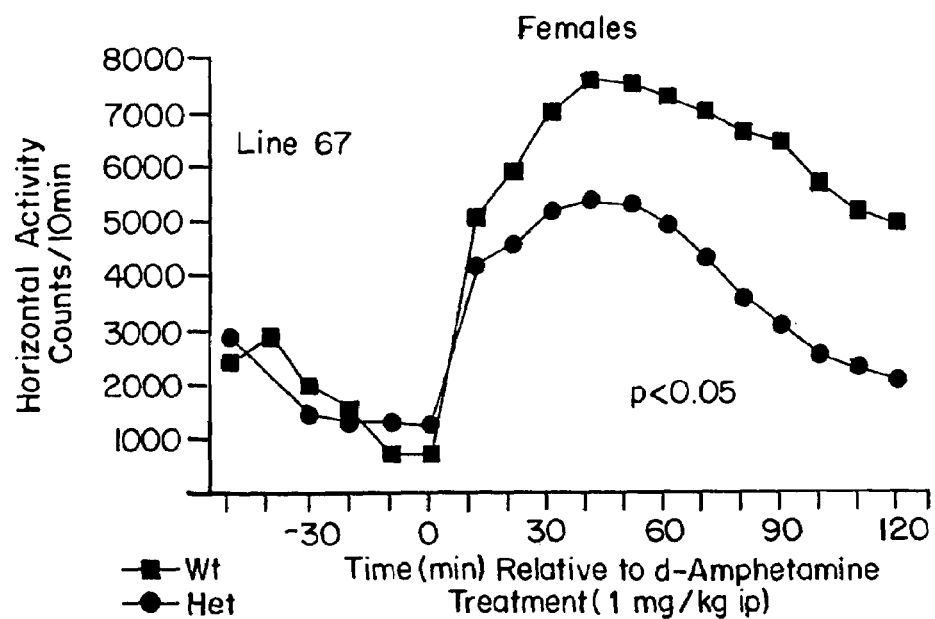
Figure 15G:
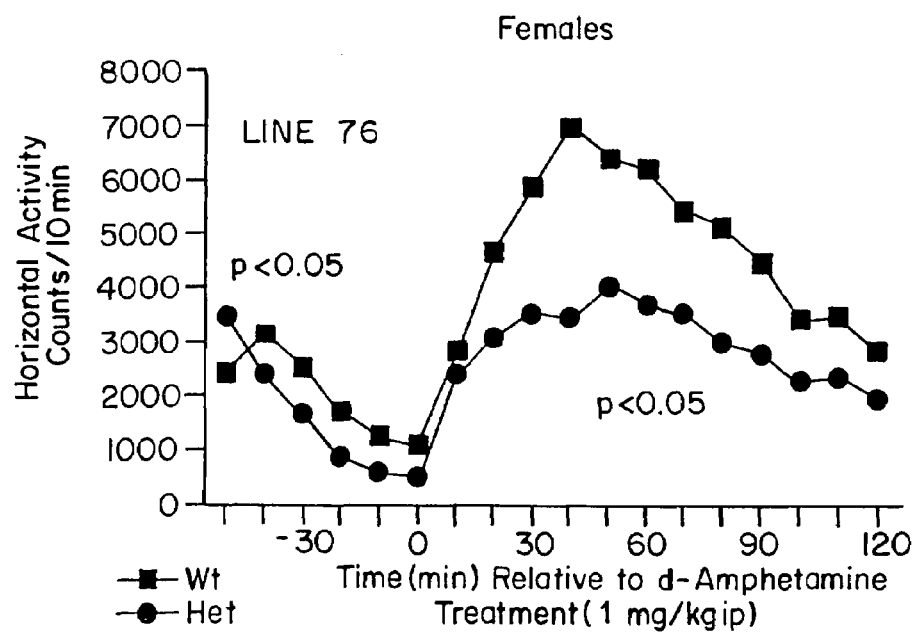
Figure 15H:
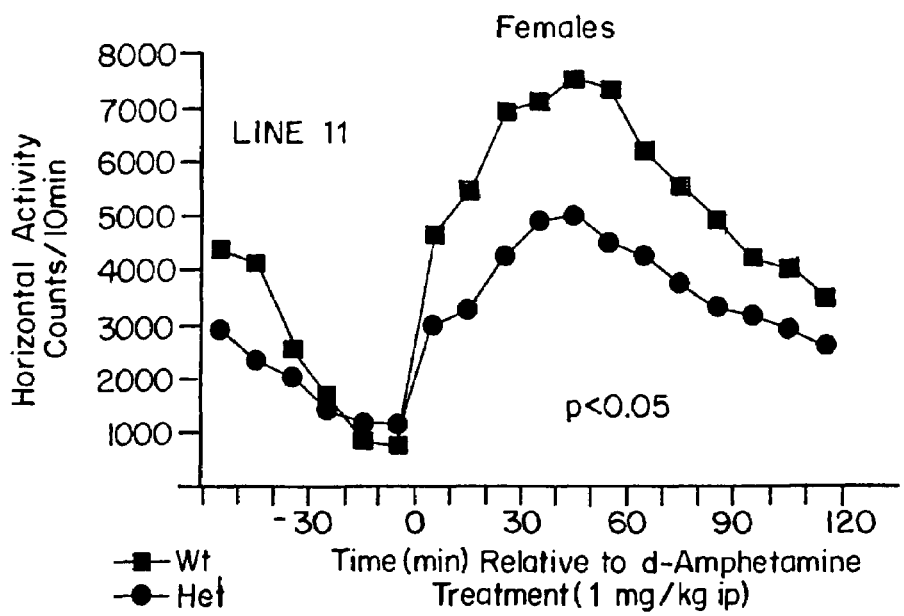
Figure 16A:
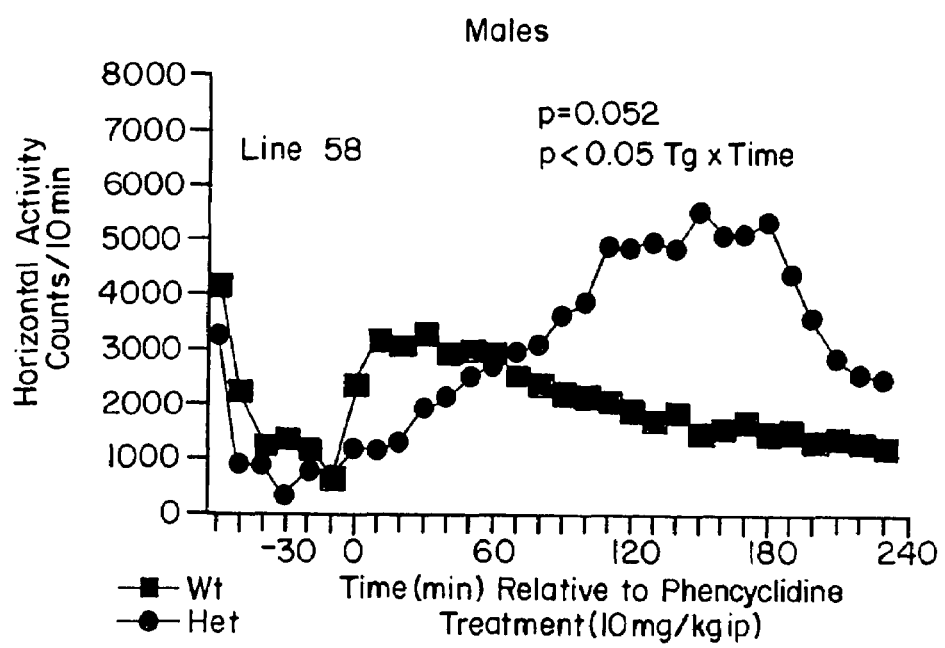
FIG. 16 (A-H) shows effects on phencyclidine on locomotor activity in male (A-E) and female (F-H) Gq transgenic rats.
Figure 16B:
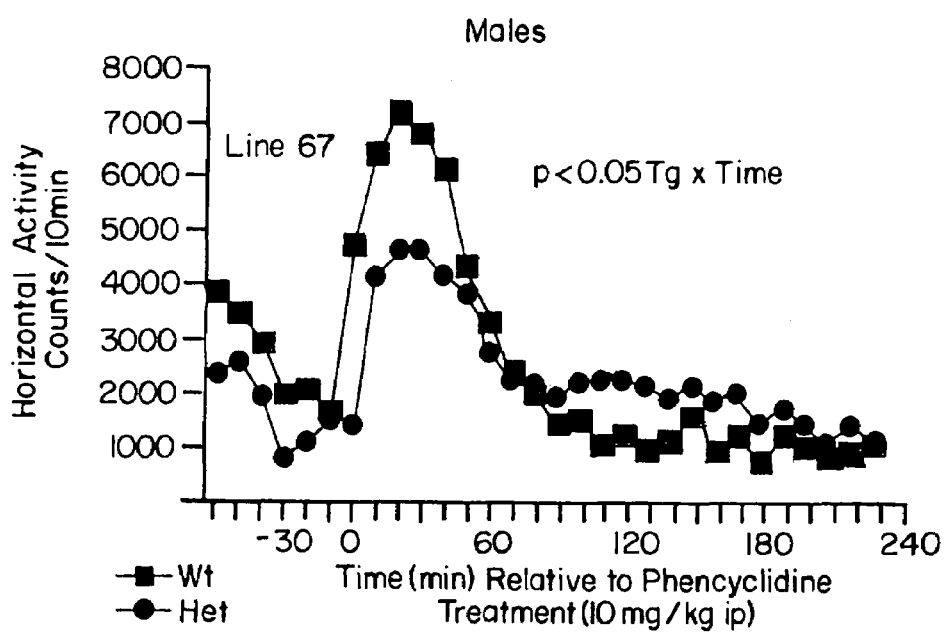
Figure 16C:
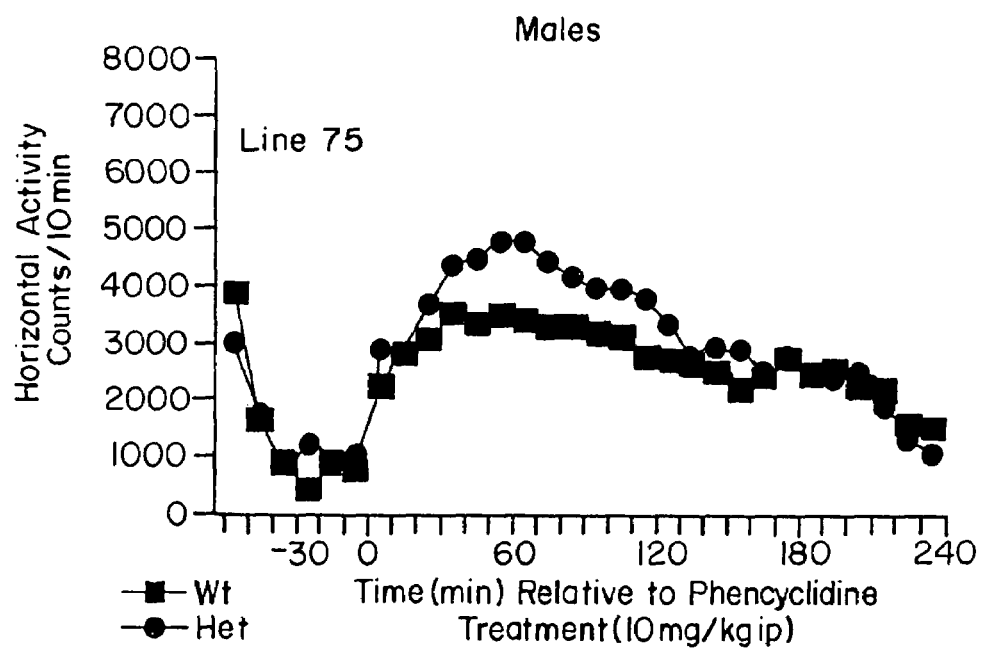
Figure 16D:
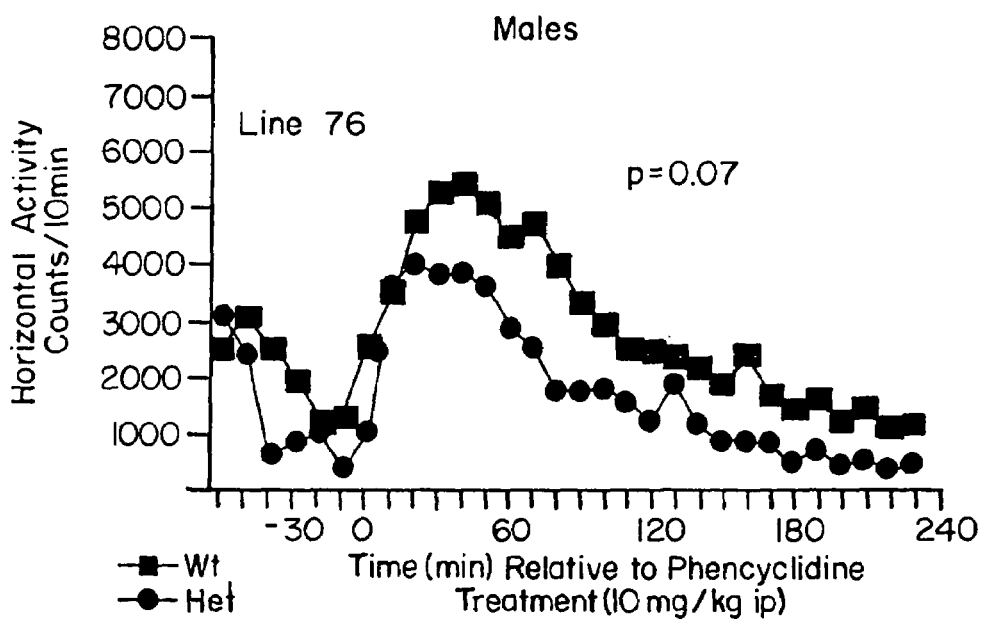
Figure 16G:
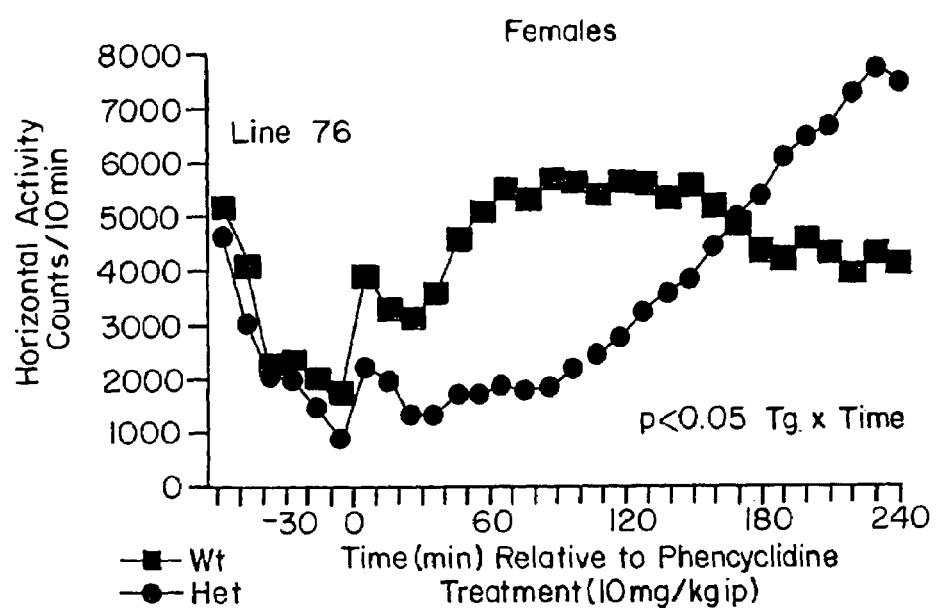
Figure 16H:
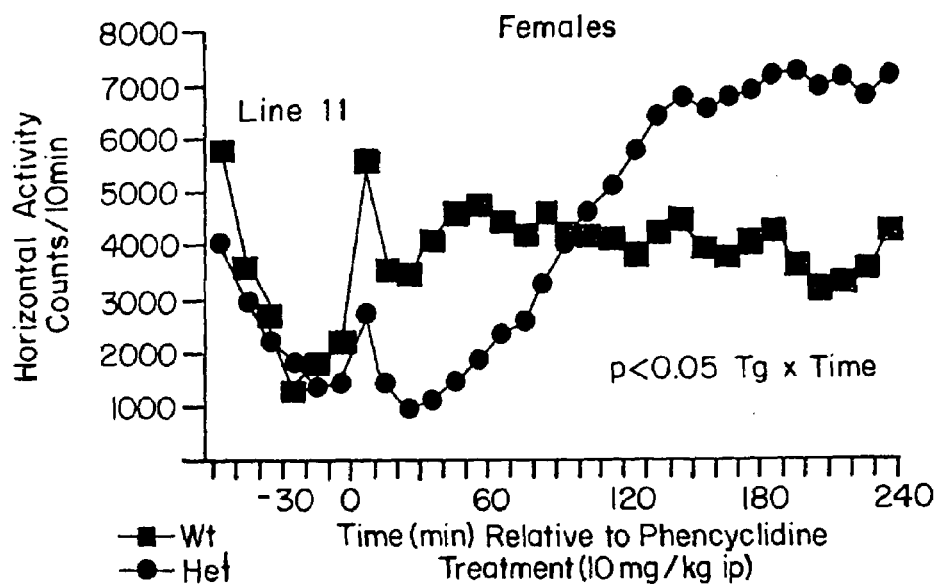

To determine an effect of the RGS insensitive Gαq mutant transgene on associative learning, contextual fear conditioning (hippocampal dependent, amygdala dependent) and auditory cue conditioning (hippocampal independent, amygdala dependent) were evaluated in rat lines. All subjects showed evidence of increased freezing in the context and in the presence of the auditory cue compared with the novel environment. FIG. 13 (A-F) summarizes the differences in freezing behavior observed in heterozygotes vs wildtype littermate controls of each line under each condition of the test. Line 76 females were demonstrated significant decreases in each condition of the test (FIG. 13D-F). Males of Line 76 showed only reduced contextual fear conditioning (FIG. 13A). Males of Line 67 also showed reduced contextual fear conditioning (FIG. 13A), whereas females of Line 67 showed trends to reduced responses on all measures (FIG. 13D-F). Lines 58 and 75 showed no significant effect and line 11 males showed increased freezing in all conditions (FIG. 13B). As Lines 67 and 76 show more hippocampal expression of the transgene, these data point toward altered hippocampal function in these lines.

No significant effects were observed in lithium diet exposed rats (data not shown).

Response to Shock

Since electric shock was used to examine associative learning, attempts to evaluate the sensitivity to this stimulus using an active escape procedure were used. A procedure was designed where subjects were first trained to escape an electric shock. Subsequently, the level of shock was reduced and incremented over trials. The percentage of trials in which the subject escaped the shock was plotted as a function of the current of shock applied.

Animals were placed into a rectangular chamber and allowed to habituate for 4 min. At the end of the habituation, the learning phase of the experiment began. During both the learning and the testing phases, shocks were presented to the ½ of the grid floor on which the animals was standing for a maximum of 10 sec or until the animal moved to the opposite end of the chamber (where no shock was being presented, i.e., escaped). Percent escape behaviors and mean escape latency were calculated across each block of 5 trials. The learning phase consisted of 5 trials at a shock intensity of 0.5 mA. Immediately following the learning phase, a testing phase began with the presentation of 5 blocks of 5 trials at increasing shock intensities (beginning at 0.1 mA and increasing in 0.1 mA increments) until the shock intensity reached 0.5 mA. Animals were then removed from the testing chamber and returned to their home cages. Data were analyzed using a paired t-test following 2-way ANOVA (transgene by condition) with one repeated measure (condition) with significance determined at $p<0.05$.

FIG. 14 summarizes the differences between heterozygotes vs wildtype littermate controls for the learning and testing phases of the assay. All lines learned to escape the shock. In the case of Line 67 there was one subject that did not meet an acquisition criterion (greater than 50% of the trials escaped) and his data was not included in the subsequent assessment of sensitivity to shock. Males and females of Line 58 showed a greater sensitivity to shock as evidenced by a shift left of the response current curve (FIG. 14A). Another line showing a difference in shock sensitivity was Line 76 where females also appeared more sensitive to shock, but males appeared less sensitive (FIG. 14A). Line 11 males also appeared less sensitive to shock but showed increased freezing behavior in the contextual fear conditioning study. Since Line 58 showed no difference in contextual fear conditioning, and Line 76 males showed decreased contextual fear conditioning, the altered sensitivity to shock appears not to play a role in the altered learning when it is observed in the mutant rats.

No consistent effects were observed in rats exposed to lithium diet (data not shown).

Spontaneous and Stimulant-Induced Locomotor Activity

To complement the observations of motor activity obtained using the open field test, heterozygotes and wildtype littermate controls were evaluated for spontaneous locomotor activity using an automated data collection system and a more extended test period. Data in this test was collected in multiple time bins over the test period allowing for some assessment of both the exploratory activity level in a novel environment as well as the rate of habituation to that environment. Having habituated the subjects, a stimulant was administered to determine the responsiveness of these subjects to the stimulant using locomotor activity as a measure. In this study we used an indirect-acting dopamine agonist, d-amphetamine, and a NMDA excitatory amino acid antagonist, phencyclidine, to induce locomotion. The ability of d-amphetamine to increase motor activity is dependent on dopaminergic neurotransmission in the striatum, in particular the nucleus accumbens, but can be influenced by other neurotransmitters. The ability of phencyclidine to induce locomotor activity is dependent on changes in both dopamine and glutatmate neurotransmission (Adams and Moghaddam, J. Neurosci. 1998, 18:5545-54). The differences in locomotor activity observed under spontaneous and stimulant-induced conditions in heterozygotes vs. wildtype littermate controls are summarized in FIGS. 15 and 16.

Subjects were placed in activity monitors (Model RXYZCM16, Omnitech, Columbus, Ohio) equipped with infrared beams to detect movements on both the horizontal (16×16 in field) and vertical axes. The testing room was equipped with white noise. Following a 60 min habituation period during which activity was monitored for differences in spontaneous locomotor activity, each subject was treated with a dose of 1 mg/kg d-amphetamine ip and returned to the activity monitor. Activity induced by d-amphetamine was monitored for 2 h. On a separate occasion, these same subjects were placed in the activity monitors and allowed to habituate for 60 min. Following this re-habituation, each subject was treated with 10 mg/kg phencyclidine ip and monitored for activity for an additional 4 h. The doses of d-amphetamine and phencyclidine were selected based on other studies as doses that induce a hyperactive state in normal rats (see Adams and Moghaddam, supra; Krebs-Thomson et al., Fur. J. Pharmacol. 1998, 343:135-43). Data were analyzed using LSD following a 2-way ANOVA (transgene×time) with one repeated measure (time). Outcomes were determined significant at $p<0.05$.

No significant change in spontaneous locomotor activity was detected in any line except in the Line 76 females, where the reduction in activity observed in heterozygotes compared to wildtype was minimal, but consistent over the majority of the test period. Males of Lines 58, 75,67, and 11 as well as females of Line 67,76, and 11, but not males of Line 76, showed reduced amphetamine-induced locomotor activity. Females of Line 58 and 75 were not tested. Because Lines 58 and 67 fail to show evidence of transgene expression in the nucleus accumbens, the reduced responsiveness to amphetamine at the challenge dose must be based on other brain regions and/or interactions of other neurotransmitters with dopamine.

Phencyclidine locomotor activity was reduced in Line 67 males (FIG. 16). There was a slight trend toward a similar reduction in phencyclidine-induced activity in Line 76 male (p=0.07). In contrast, Line 58 males showed an increase in locomotor activity induced by phencyclidine that was delayed in the onset and resembled the pattern of motor activation associated with a higher dose of phencyclidine (pronounced ataxia and sedation followed by intense motor activity). The same delayed hyperactivity was observed in Line 76 females, Line 11 males and females, and to a lesser degree in Line 67 females. Females for Lines 58 and 75 were not tested. There was not a consistent phenotype associated with an expression pattern of the transgene. Since 5-HT2A agonists have been reported to influence phencyclidine-induced locomotor activity (Krebs-Thomson et al., 1998), the current results may represent an interaction of a modified serotonergic neurotransmitter system (see results reported below with DOI head shakes).

Figure 17:
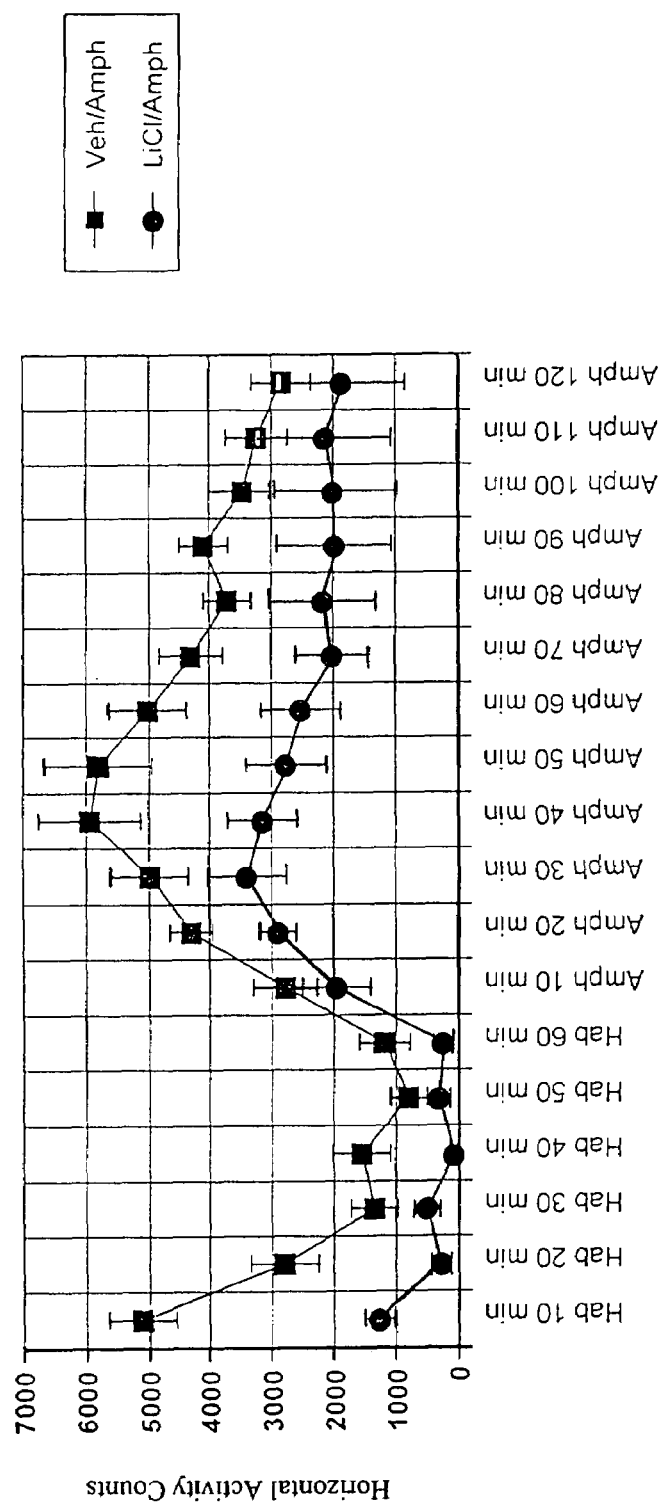
FIG. 17 shows effects of d-amphetamine on locomotor activity following acute lithium treatment.
Figure 18:
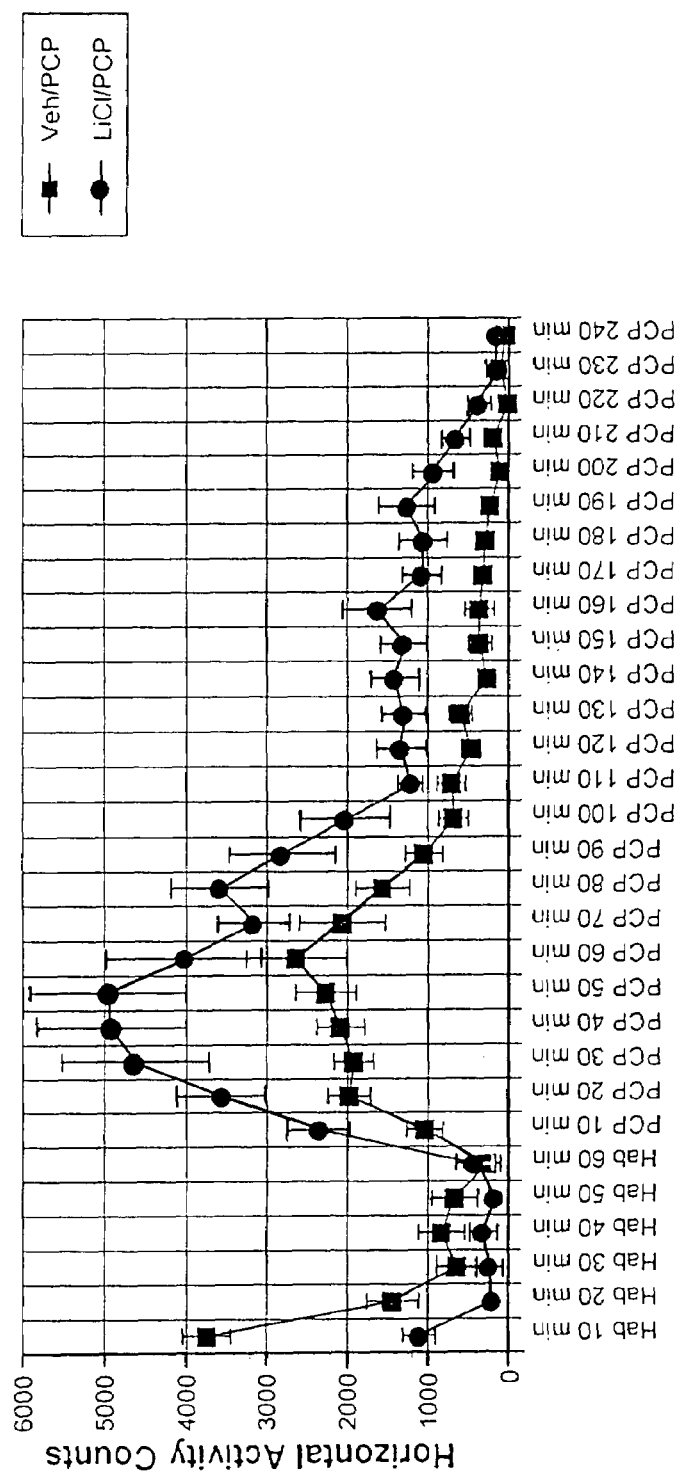
FIG. 18 shows effects of phencyclidine on locomotor activity following acute lithium treatment.

Acute lithium decreased spontaneous locomotor activity during the habituation period (FIGS. 17 and 18, habituation periods). Lithium attenuated the increases in locomotor activity produced by d-amphetamine (1 mg/kg) (FIG. 17) and enhanced the locomotor activating effects of PCP (10 mg/kg) (FIG. 8).

Figure 19:
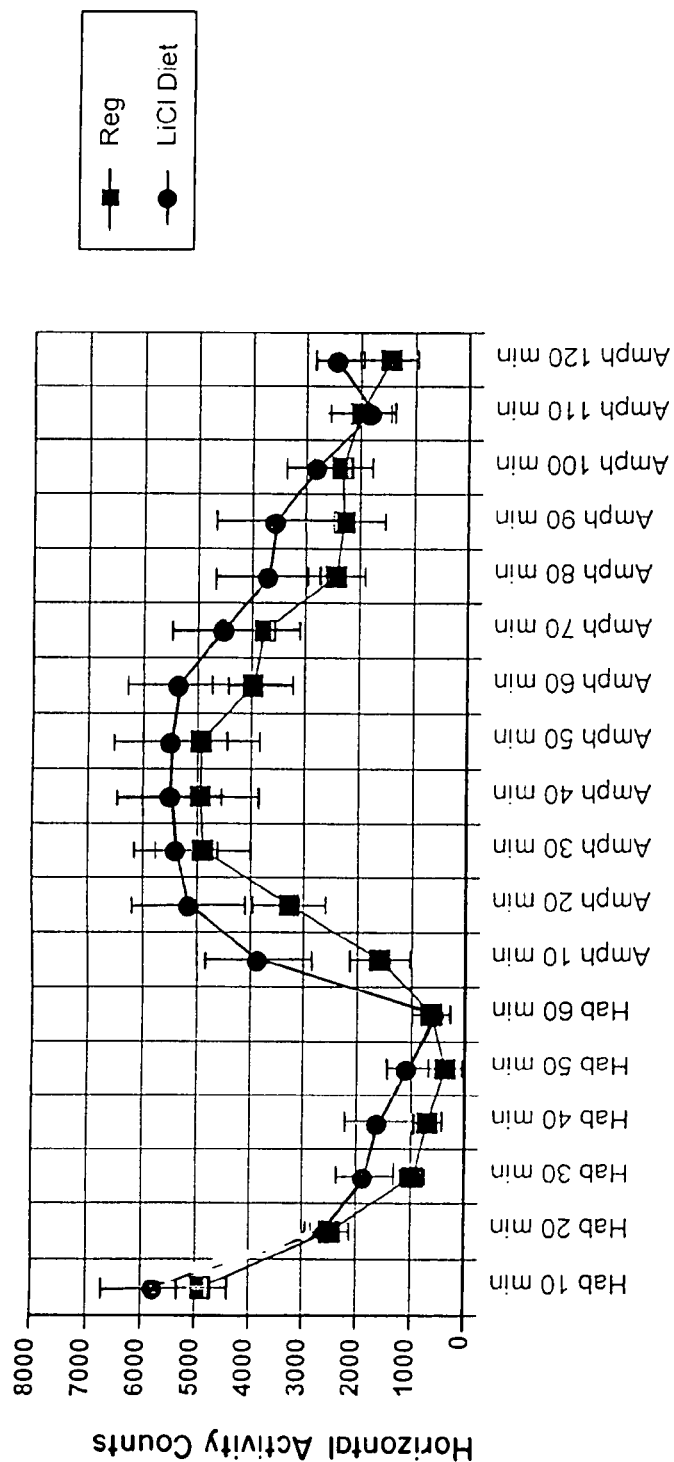
FIG. 19 shows effects of d-amphetamine on locomotor activity in rats maintained on lithium chloride diet.
Figure 20:
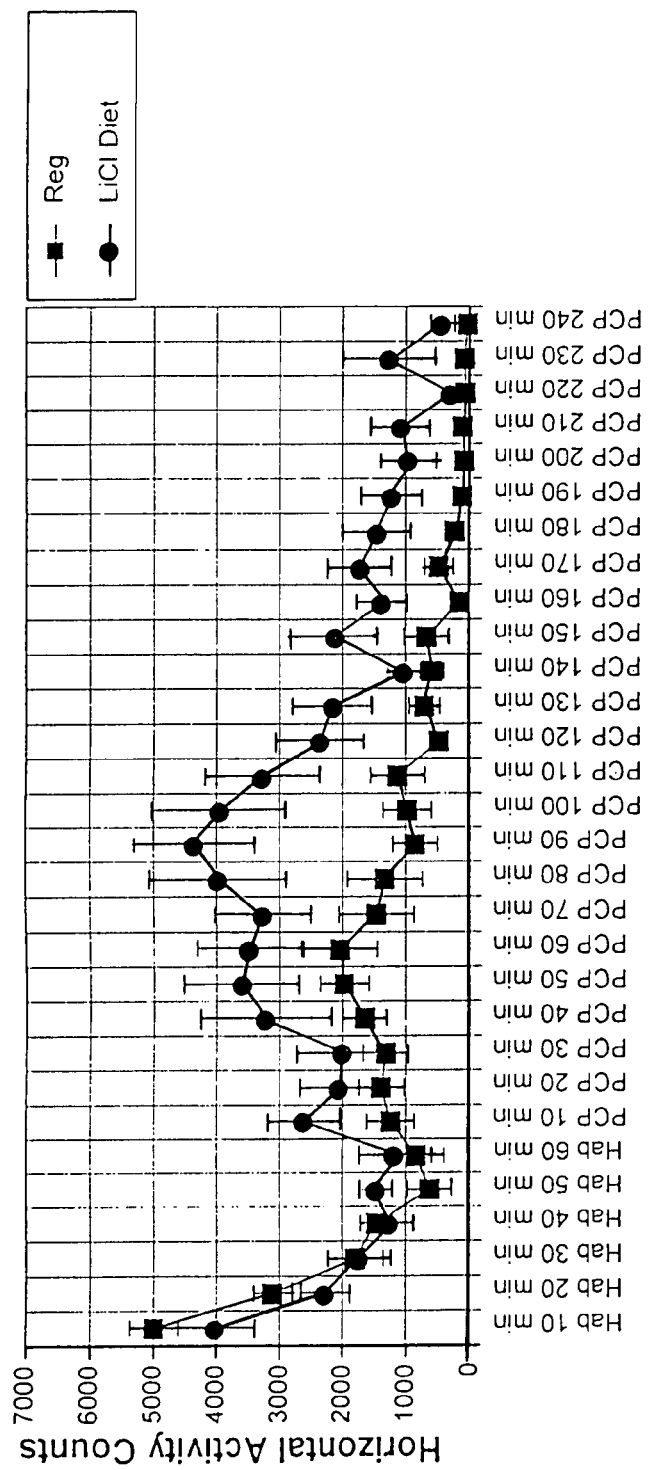
FIG. 20 shows effects of phencyclidine on locomotor activity in rats maintained on lithium chloride diet.

Male rats exposed to high concentration of lithium diet (4.3 g/kg) for one week did not show any differences from control in spontaneous or d-amphetamine-stimulated locomotor activity (FIG. 19); however these rats did show enhanced phencylidine-stimulated activity (FIG. 20).

Open Field

To assess the effect on general 'anxious' behavior of the animal, an open field test paradigm is used. The open field model evaluates two primary measures. The latency to return to the center square is indicative of an "anxiolytic-like" (decreased latency) or an "anxiogenic-like" (increased latency) effect. The number of line crosses and rears is indicative of changes in motor activity.

Typically, a rat placed within the center of a 3'×3' square field will move to an outside square (along a wall). Returning to the center square is a demonstration of 'non-anxious' or 'less anxious' behavior. The time recorded to return to the center square serves as an index to 'anxiolytic' or 'anxiogenic' activity. For example, a longer return (to center-square) time is associated with a more anxious phenotype (anxiogenic).

Experiments were conducted in a 3'×3' black Plexiglas open field. The height of the walls on the open field was 18 inches. On the floor of the field were white lines that divided the field into 9 squares. Wild type and transgenic rats were placed singly into the center square of the open field. The latency of the rat to exit the center square (center exit time) was recorded. The latency of the rat to return to the center square (center return time) was recorded. In addition, the number of line crosses and the number of rears were recorded. All experiments were 15 min in duration and were conducted in dimly lit rooms (2-4 lux). Wild type and transgenic rats were approximately 7 weeks of age at the time of these experiments. Statistical significance was determined by ANOVA and set to $p<0.05$.

Figure 21A:
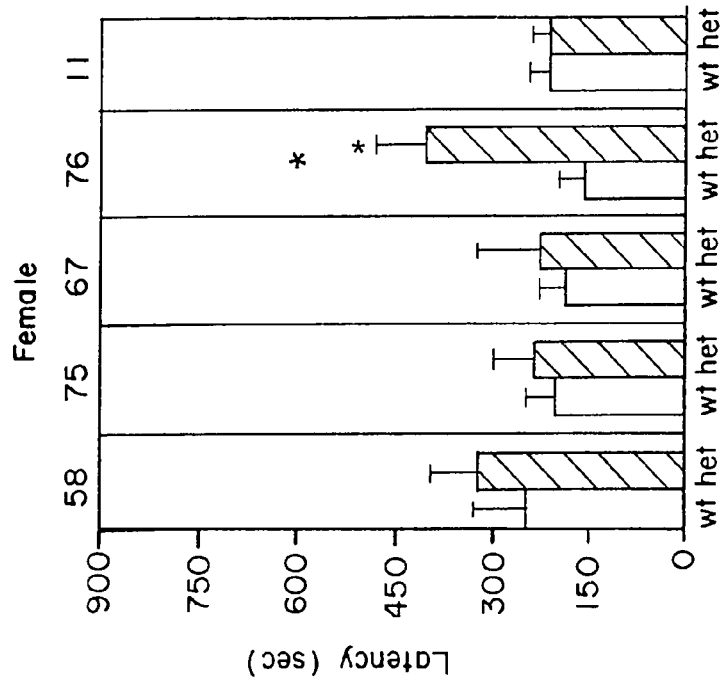
FIG. 21 (A and B) shows open field behavior (center return time) in male (A) and female (B) Gq transgenic rats.
Figure 21B:
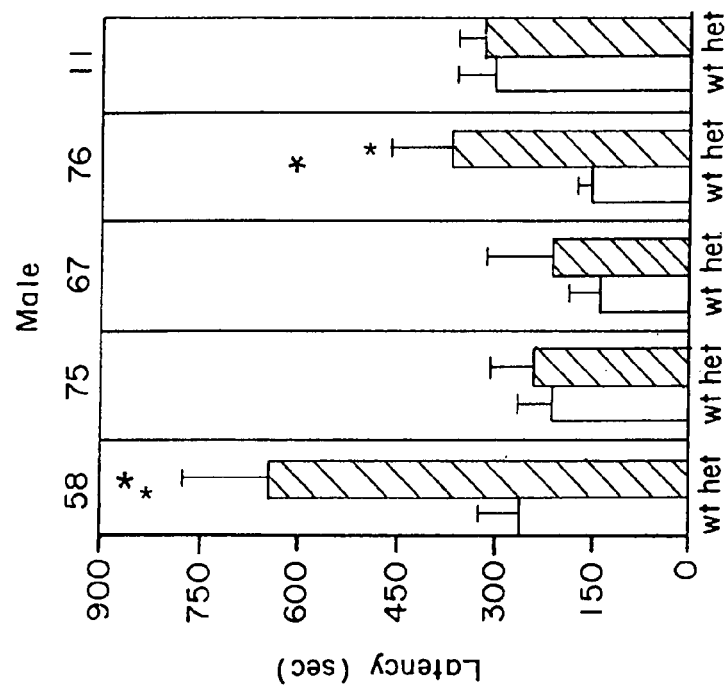
Figure 23A:
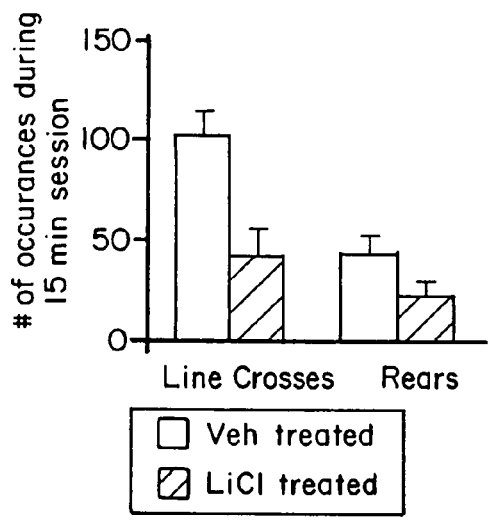
FIG. 23 (A-D) shows open field behavior following acute lithium treatment based on number 4 occurrences in a 15 minutes session (A), center exit times (B), center Return time (C), time spent (D).
Figure 23B:
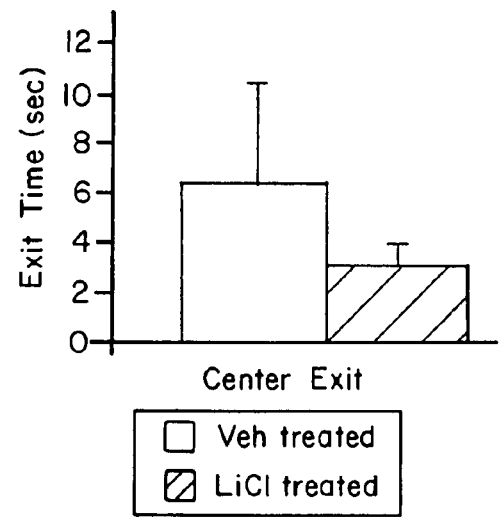
Figure 23C:
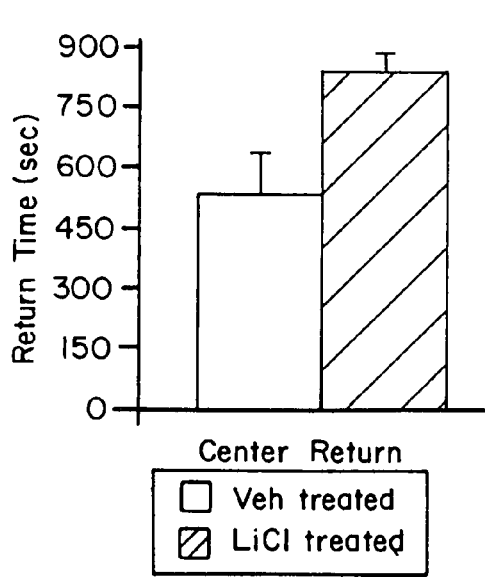
Figure 23D:
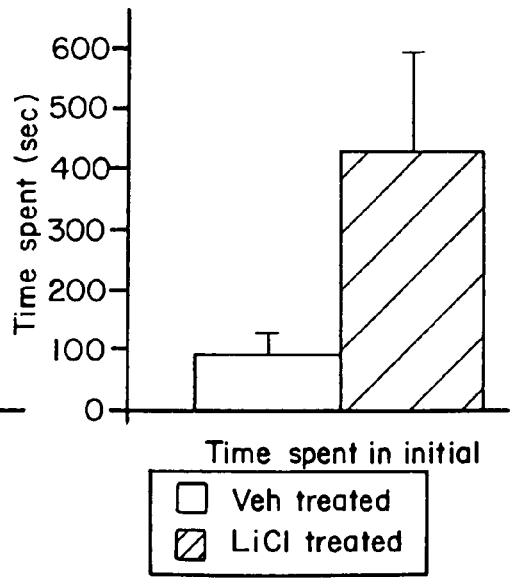
Figure 24B:
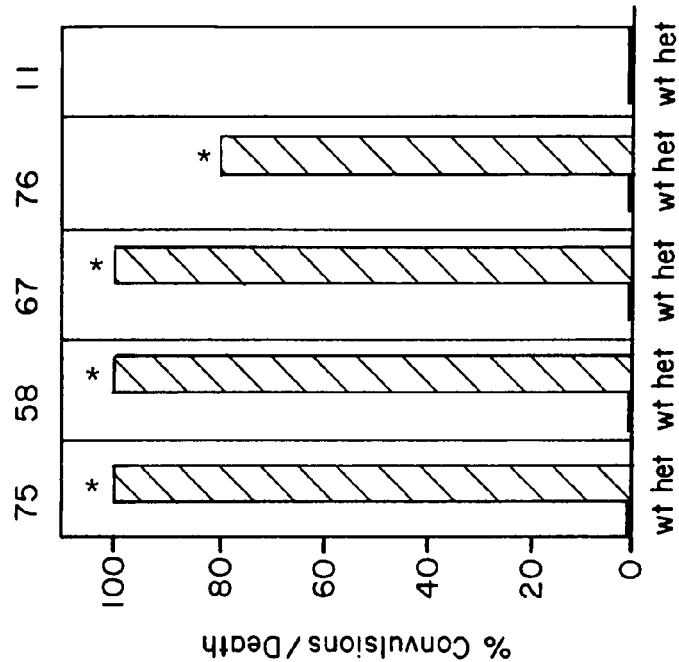
FIG. 24 (A and B) shows effects of a 5-HT2A agonist on headshakes (A) and convulsions (B) in Gq transgenic rats.
Figure 24A:
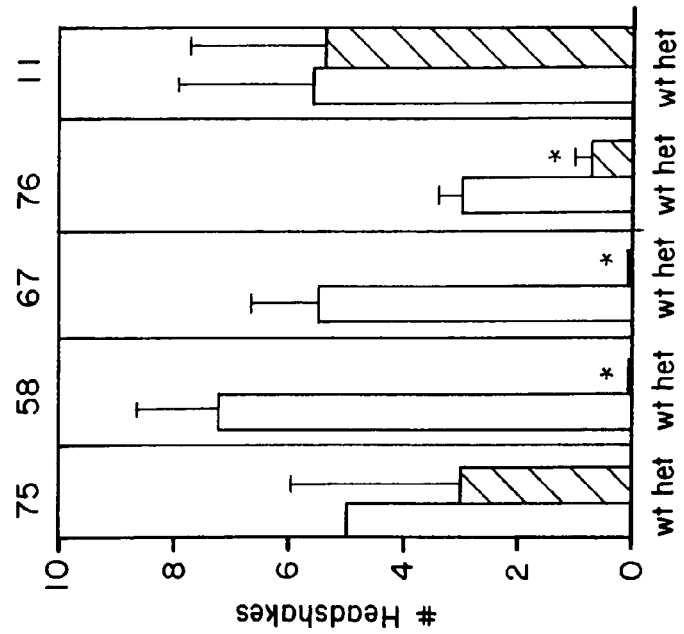

Male transgenic heterozygote rats from line 58 and both males and females from line 76 showed an increased latency to return to the center of the open field, suggesting a possible "anxiogenic-like" profile for these animals (FIG. 21). Male transgenic heterozygote rats from lines 67 and 76 showed a decreased activity profile with a decreased number of line crosses (FIG. 22). This pattern of results across the transgenic rat lines demonstrates that these behaviors can be doubly dissociated. That is, the "anxiogenic-like" effects can occur in the presence (line 76 male) or absence (line 58 male; line 76 female) of decrease in motor activity. In addition, decreases in motor activity can occur in the presence (line 76 male) or absence (line 67 male) of "anxiogenic-like" effects. Results of the open field test for animals subjected to the acute lithium treatment are shown in FIG. 23. Animals maintained on lithium diet did not differ from control animals (data not shown).

DOI Induced Headshakes

Wild type and transgenic rats were injected ip with either vehicle or DOI (0.001, 0.01, 0.1, 1.0 mg/kg) and were then housed singly in clear Plexiglas chambers (10"×18"×8") for observational studies. A trained observer counted the number of headshakes for each rat during 2 observation periods (0-30 min; 45-75 min).

Assessing the effect of the RGS insensitive Gαq mutant transgene on receptors coupled via Gαq to the IP3 pathway in transgenic rats was an interest. 5-HT2A agonists produce large increases in headshakes in rats via this pathway. DOI (−1[2,5-dimethoxy-4-iodophenyl]-2-aminopropane) is a 5-HT2A receptor agonist, which increases headshakes in rats, and it has been used to investigate this pathway (Wettstein et al., 1999). DOI administration was used herein to determine if 5-HT2A agonist activity was modified in transgenic rats; results are shown in FIG. 27.

Surprisingly, transgenic rats from lines 58, 75, 67 and 76 that were administered 1 mg/kg of DOI were found dead within 24 hours of administration. Higher doses of DOI (3-10 mg/kg) were required to produce similar effects in line 11 (data not shown). In separate experiments, doses of DOI as high as 30 mg/kg in normal Sprague-Dawley rats did not result in lethality. A lower dose of DOI (0.1 mg/kg) increased the number of headshakes in line 75 male transgenic heterozygote rats and showed a trend toward increased headshakes in line 67 male transgenic heterozygote rats (dta not shown). These data demonstrate 5-HT2A agonist effects that are mediated through Gαq can be potentiated in the presence of Gαq mutants that are not regulated by RGS proteins.

Figure 25:
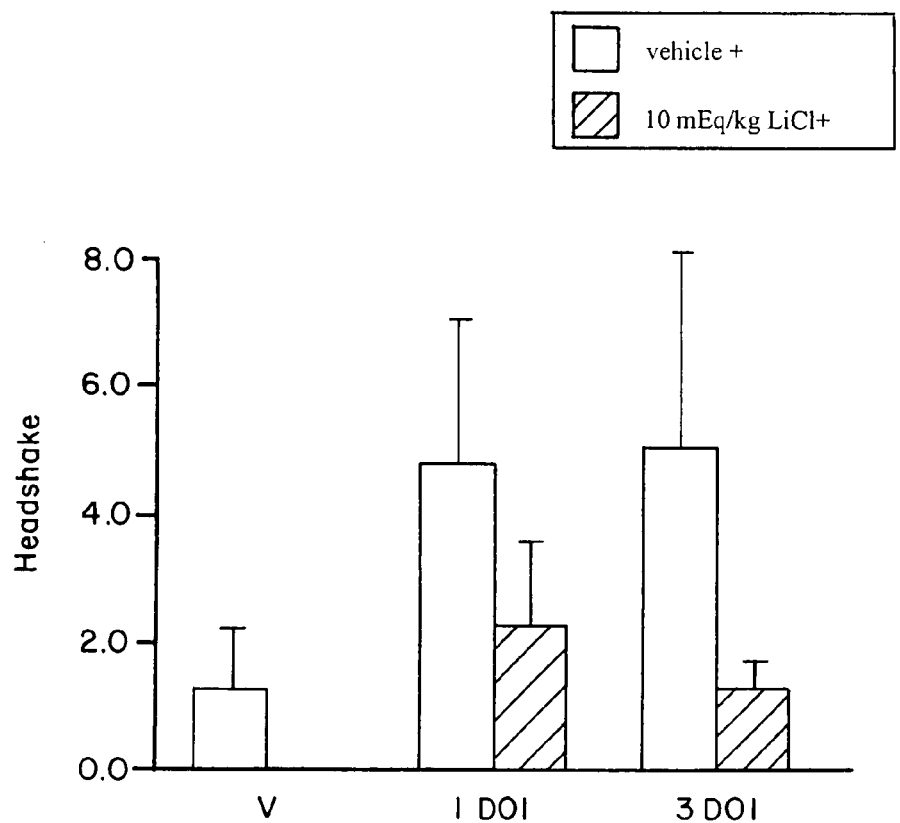
FIG. 25 shows effects of a 5-HT2A agonist on headshakes following acute lithium treatment.
Figure 26:
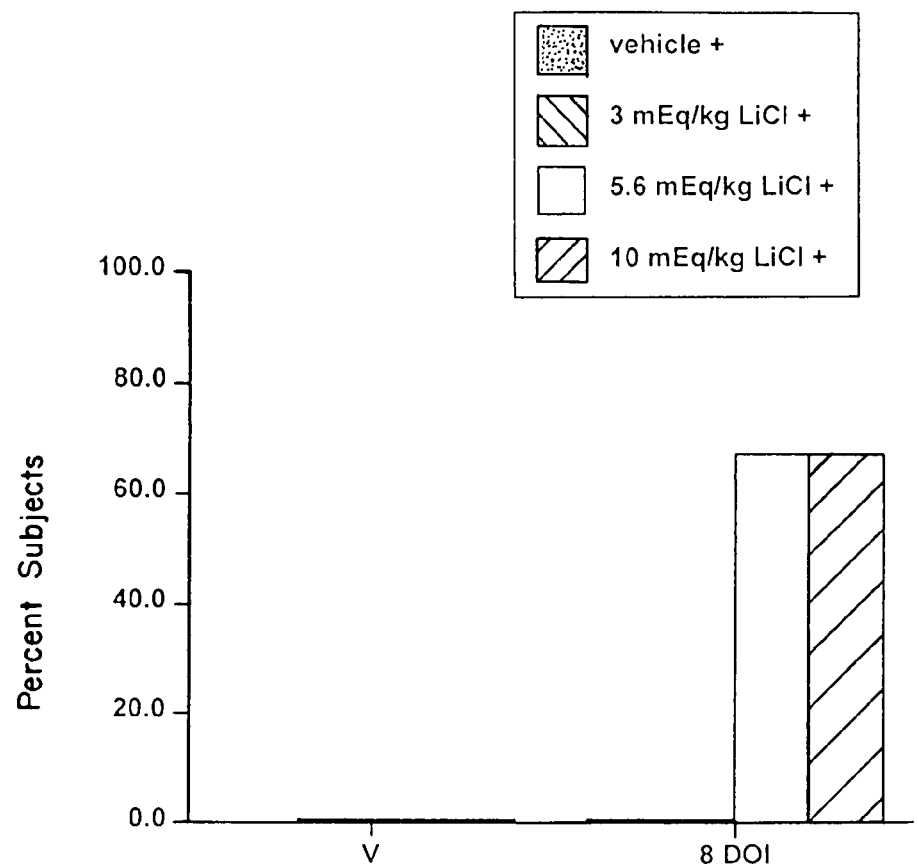
FIG. 26 shows effects of a 5-HT2A agonist on convulsions following acute lithium treatment.
Figure 27B:
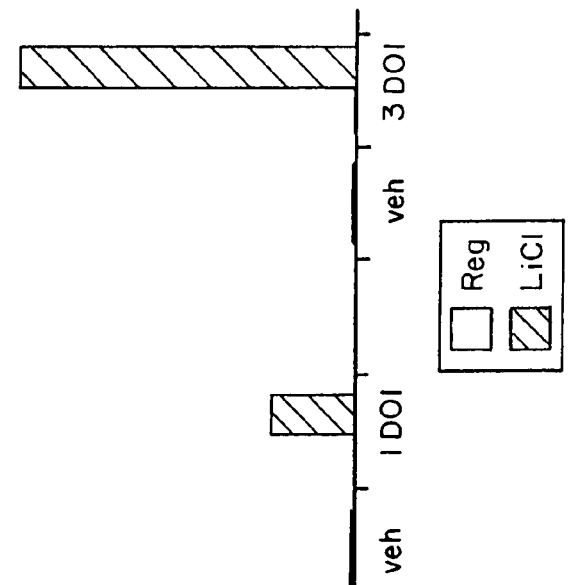
FIG. 27 (A and B) shows effects of a 5-HT2A agonist on headshakes (A) and lethality (B) in rats maintained on chronic lithium diet.
Figure 27A:
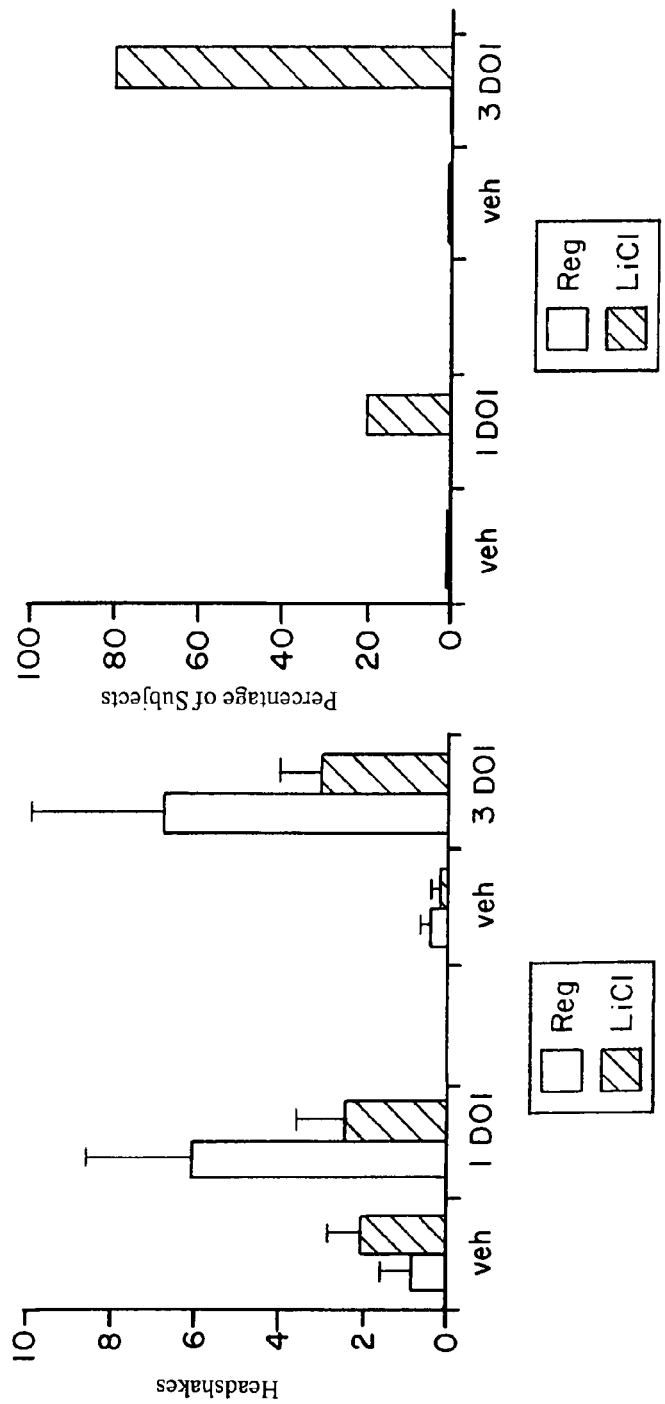

Studies using the selective 5-HT2A agonist DOI were conducted to determine if 5-HT2A agonist activity was modified by acute or chronic lithium (FIGS. 25-27). Acute lithium attenuated the increases in headshakes produced by 1 or 3 mg/kg DOI (FIG. 25). In addition, lithium pretreatment (5.6 -10 mEq/kg) resulted in convulsions and lethality in rats treated with 8 mg/kg DOI (FIG. 26). DOI headshakes produced by 1 or 3 mg/kg DOI were also reduced in rats exposed to lithium diet (2.2 g/kg) (FIG. 27). Moreover, convulsions and lethality were observed following 3 mg/kg DOI.

Pilocarpine-Induced Cholinergic Signs and Convulsions

Figure 28C:
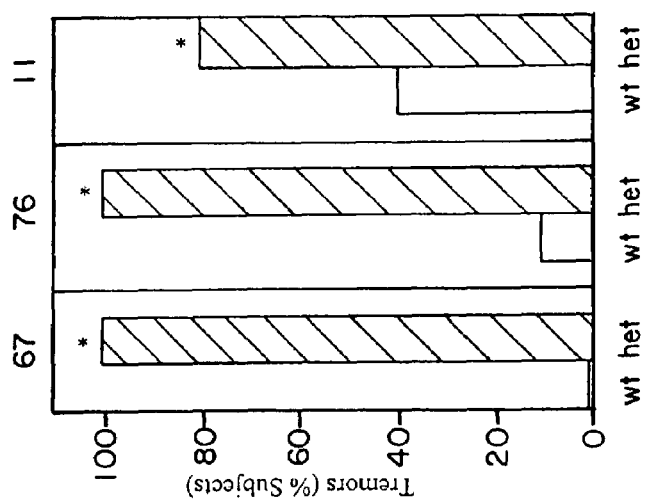
FIG. 28 (A-C) shows effects of a muscarinic agonist in inducing tremors (A), convulsions (B) or death (C) in Gq transgenic rats.
Figure 28B:
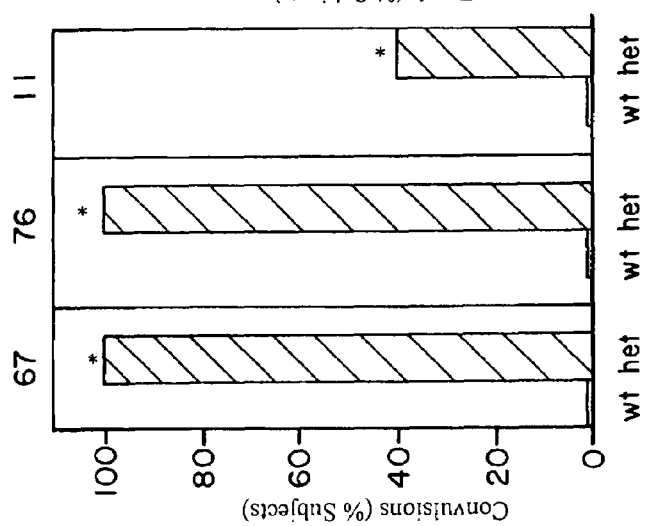
Figure 28A:
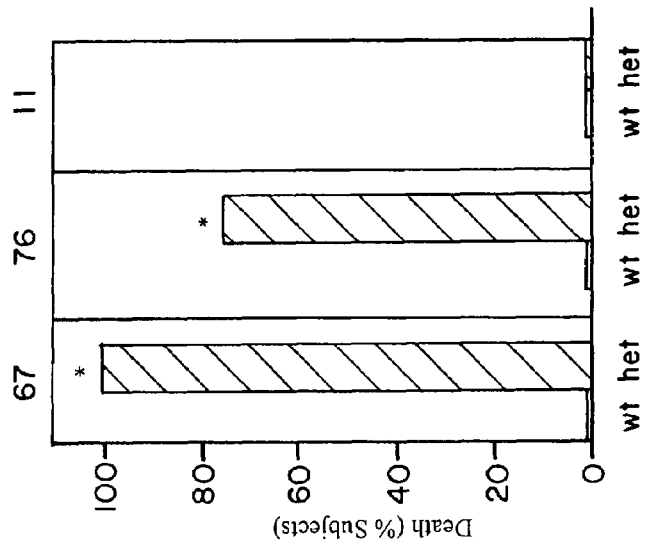
Figure 29A:
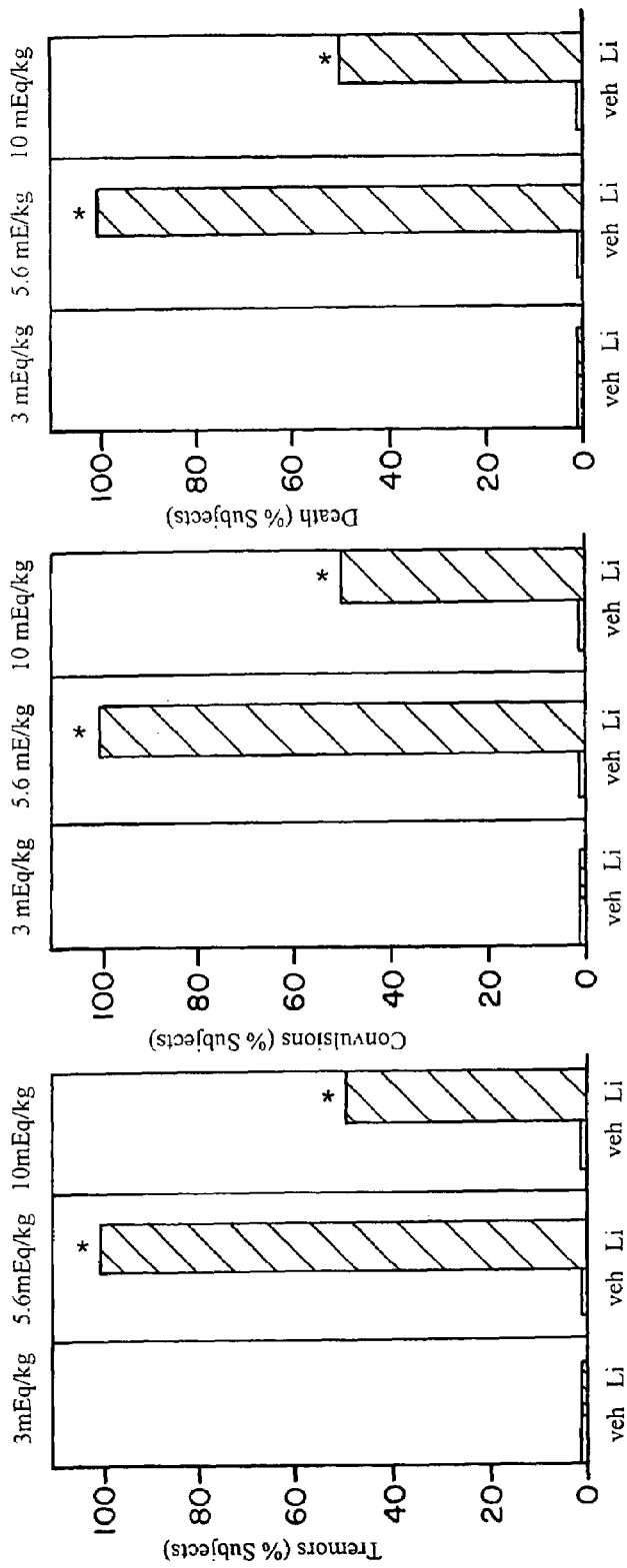
FIG. 29 (A-C) shows effects of a muscarinic agonist over following acute lithium treatment.
Figure 29B:
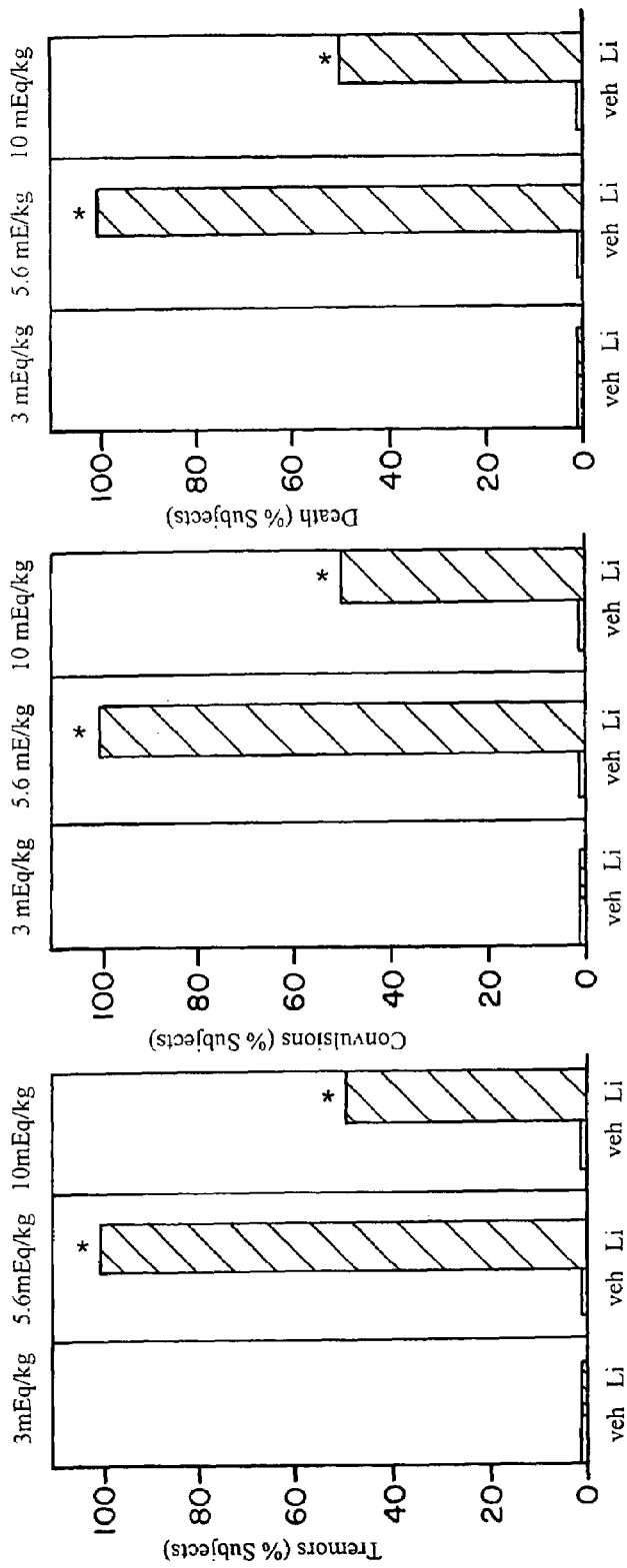
Figure 29C:
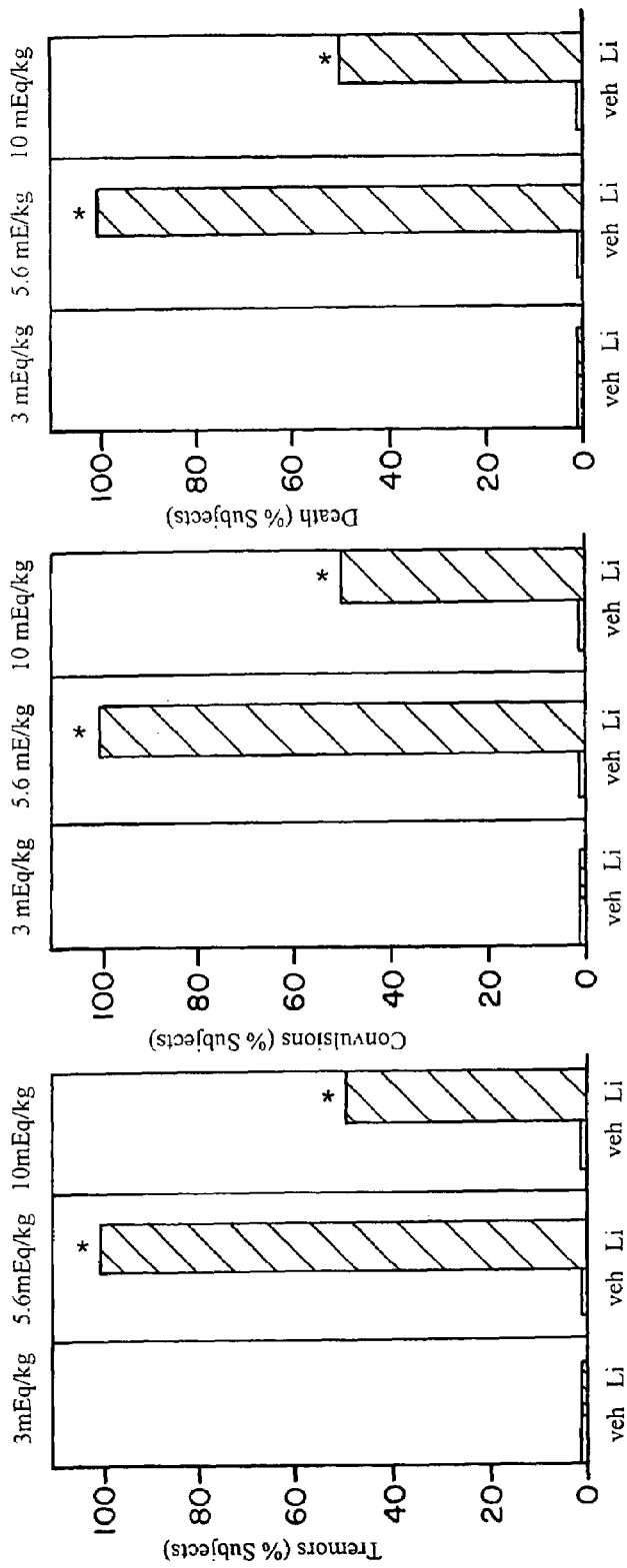
Figure 30A:
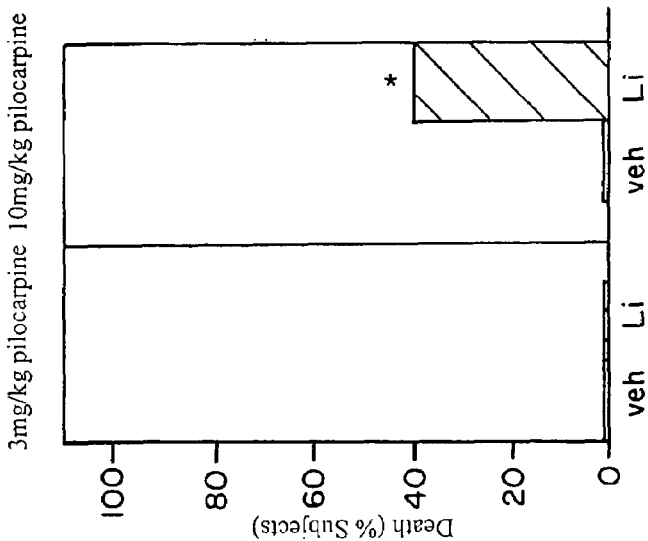
FIG. 30 (A-C) shows effects of a muscarinic agonist in inducing tremors (A), convulsions (B) and death (C) on rats maintained on a LiCl diet.
Figure 30B:
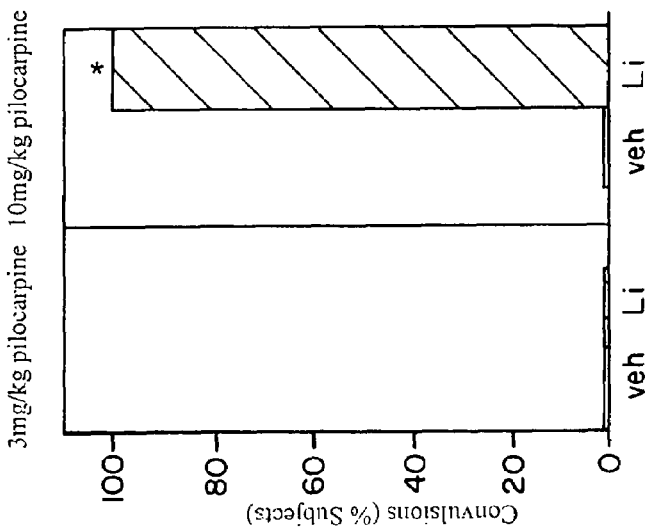
Figure 30C:
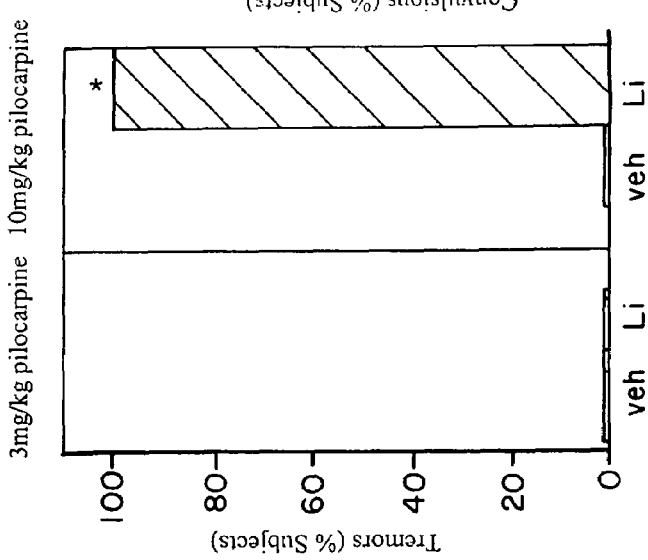

Muscarinic cholinergic agonists produce a series of cholinergic signs (chromodacryrhea, salivation, diarrhea, hypoactivity, tremors, foaming, convulsions and death) at high doses via a Gαq modulated pathway. Studies were conducted with the muscarinic agonist pilocarpine to determine if muscarinic agonist activity was modified in the transgenic rats (FIG. 28). Studies were conducted with the muscarinic agonist pilocarpine to determine if muscarinic agonist activity was modified by acute lithium (FIG. 29 or chronic lithium (FIG. 30). Both acute and chronic lithium potentiated the cholinergic signs produced by pilocarpine.

The similarities between acute treatment with lithium (10 mEq/kg, 20-24 h pretreatment), chronic lithium diet (1.7-4.3 g/kg) and Gαq mutant transgenic rats are summarized in Table 5 below. All phenotypic effects that are observed in Gαq mutant transgenic rats are observed following either acute or chronic treatment with lithium. The phenotypic effects observed occur on non-pharmacologically-induced behaviors and on pharmacologically-induced behaviors. For example, lithium treated and Gαq mutant transgenic rats show similar behavioral effects with respect to vibration, open field behavior, food intake, body weight and prepulse inhibition. In addition lithium treated and Gαq mutant transgenic rats show similar potentiations of behavioral effects induced by stimulation of Gαq coupled receptors (5-HT2C, 5-HT2A, muscarinic). Additionally, they also show similar modifications of the effects of indirect dopamine agonists (attenuate) and NMDA antagonists (enhance).

The parallels observed between the Gαq mutant transgenic rats and lithium treatment indicate that Gαq mutant transgenic rats represent a model of lithium treated bipolar affective disorder. Since the Gαq mutant transgenic animals mimic the effects of RGS-blockade, these parallels suggest that RGS-blockers may be useful in the treatment of bipolar affective disorder. In addition, transgenic rats are useful for studying the effects of compounds in RGS-blocked animals, which is important for evaluating drug interactions and conflicts.

TABLE 5

Comparative Profile of Acute or Chronic Lithium and Gαq mutant Transgenic Rats
(a Model of RGS Blockade)

|  | Lithium (10 mEq/kg) 20–24 hr pretreatment | Lithium Diet (1.7 g/kg) | Gαq mutant Transgenics |
|---|---|---|---|
| Global Behavioral Assessment | — | Vibration | All lines vibration |
| Open Field |  |  |  |
| Center Return Time | ↑ CRT | nsd | 2 of 5 lines ↑ CRT |
| Line Crosses | Marked ↓ LC | nsd | 2 of 5 lines ↓ LC |
| Food Intake | Marked ↓ food intake | nsd | ↓ food intake |
| Body Weight | — | ↓ body weight | ↓ body weight |
| 5-HT2C Agonist (RO60-0175) Inhibition of Food Intake | Lithium effect overshadows any 2C effect | ↑ sensitivity to RO 60-0175 | 2 of 5 lines ↑ sensitivity to RO 60-0175 |
| 5-HT2A Agonist (DOI) Induction of Head Shakes | ↓ headshakes | ↓ headshakes | 4 of 5 lines ↓ headshakes |
| 5-HT2A Agonist (DOI) Flattened Body Posture (FBO), Convulsions (CONY), Death | Conv and Death (8 mg/kg) | Conv and Death (3 mg/kg) | 4 of 5 lines show FBP, cony, and death (1.0 mg/kg); higher doses required for line 11 |
| Muscarinic Agonist (Pilocarpine) Induction of cholinergic signs | ↑ cholinergic signs | ↑ cholinergic signs. | 3 of 3 lines tested ↑ cholinergic signs |
| Muscarinic Agonist (Pilocarpine) Convulsions, Death | Conv and Death (30 mg/kg) | Conv and Death (10 mg/kg). | 3 of 3 lines tested conv and death (10–30 mg/kg) |
| Prepulse Inhibition (PPI) | ↓ PPI | ↓ PPI | All lines ↓ PPI |
| Noncompetitive NMDA antagonist (PCP) Locomotor Activity | ↑ hyperactivity | ↑ hyperactivity | 4 of 5 lines ↑ hyeractivity (delayed) |
| Indirect DA agonist (d-amph) Locomotor Activity | ↓ hyperactivity | nsd | All lines ↓ hyperactivity | n.s.d. = no significant difference
n.t. = not tested

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

We claim:

1. A transgenic rat containing in its genome a nucleotide sequence encoding a mutant Gαq subunit protein, wherein said mutant Gαq subunit protein has glycine 188 substituted with serine (G188S) and wherein said mutant Gαq subunit protein is uncoupled from regulation by Regulators of G-protein Signaling (RGS) proteins, said nucleotide sequence being operatively linked with a neuron-specific expression control sequence, wherein the transgenic rat expresses the Gαq subunit protein in neural cells resulting in extended G-protein coupled receptor signaling mediated by the Gαq subunit protein, and wherein said transgenic rat exhibits a phenotype selected from the group consisting of vibration as assessed by global behavior assessment; increased center return time as assessed by an open field test; decreased contextual fear conditioning; decreased food intake; decreased body weight; increased sensitivity to 5-HT2A agonists and 5-HT2C agonists; increased cholinergic signs in response to muscarinic agonists; decreased prepulse inhibition; increased hyperactivity in response to N-methyl D-aspartate (NMDA) antagonists; and decreased hyperactivity in response to dopamine (DA) agonists, as compared to a wild type control.

2. The transgenic rat of claim 1, wherein a G-protein coupled receptor that demonstrates extended signaling is selected from the group consisting of a muscarinic receptor, a 5-hydroxytryptamine (HT)2A receptor, a 5-HT2C receptor, an N-methyl D-aspartate (NMDA) receptor, and a dopamine (DA) receptor.

3. The transgenic rat of claim 1, wherein the G188S mutation in the mutant Gαq subunit protein is a dominant-negative mutation.

4. A transgenic rat containing in its genome a nucleotide sequence encoding a mouse mutant Gαq subunit that has glycine 188 substituted with serine (G188S), wherein said mutant Gαq subunit has a dominant-negative mutation and is uncoupled from regulation by Regulators of G-protein Signaling (RGS) proteins, said nucleotide sequence being operatively linked with a neuron-specific expression control sequence such that the mutant Gαq subunit protein is expressed in neural cells resulting in extended G-protein coupled receptor signaling mediated by the Gαq subunit protein, and wherein said transgenic rat exhibits a phenotype selected from the group consisting of vibration as assessed by global behavior assessment; increased center return time as assessed by an open field test; decreased contextual fear conditioning; decreased food intake; decreased body weight; increased sensitivity to 5-HT2A agonists and 5-HT2C agonists; increased cholinergic signs in response to muscarinic agonists; decreased prepulse inhibition; increased hyperactivity in response to NMDA antagonists; and decreased hyperactivity in response to DA agonists, as compared to a wild type control.

5. The transgenic rat of claim 4, wherein the mutant Gαq subunit does not interact with RGS proteins.

6. The transgenic rat of claim 1, wherein the neuron-specific expression control sequence comprises a Thy 1.2 promoter.

7. A method for identifying a potential agent that modulates RGS modulation of Gαq hydrolysis of GTP, which method comprises comparing a phenotype of a test wild-type rat to which a test compound is administered to a phenotype of the transgenic rat of claim 1, wherein the test compound modulates RGS modulation of Gαq hydrolysis of GTP when the phenotype of the test rat is similar to the phenotype of the transgenic rat.

8. The method of claim 7, wherein the phenotype being compared between the test wild-type rat and the transgenic rat is selected from the group consisting of vibration as assessed by global behavior assessment; increased center return time as assessed by an open field test; decreased contextual fear conditioning; decreased food intake; decreased body weight; increased sensitivity to 5-HT2A agonists and 5-HT2C agonists; increased cholinergic signs in response to muscarmnic agonists; decreased prepulse inhibition; increased hyperactivity in response to NMDA antagonists; and decreased hyperactivity in response to DA agonists.

9. The method of claim 7, wherein the G188S mutation in the mutant Gαq subunit protein is a dominant-negative mutation.

10. The method of claim 9, wherein the Gαq is a mouse Gαq.

11. A method for identifying a potential agent that modulates RGS modulation of Gαq hydrolysis of GTP, comprising comparing a phenotype of a test wild-type rat to which a test compound is administered to a phenotype of the transgenic rat of claim 4, wherein the test compound modulates RGS modulation of Gαq hydrolysis of GTP when the phenotype of the test rat is similar to the phenotype of the transgenic rat, and wherein the phenotype being compared between the test wild-type rat and the transgenic rat is selected from the group consisting of vibration as assessed by global behavior assessment; increased center return time as assessed by an open field test; decreased contextual fear conditioning; decreased food intake; decreased body weight; increased sensitivity to 5-HT2A agonists and 5-HT2C agonists; increased cholinergic signs in response to muscarmnic agonists; decreased prepulse inhibition; increased hyperactivity in response to NMDA antagonists; and decreased hyperactivity in response to DA agonists.

12. The method of claim 11, wherein the mutant Gαq subunit does not interact with RGS proteins.

13. The method according to claim 7, wherein the compound is a lead for treating bipolar disorders.

14. A method for identifying the effect of a compound on an animal in which Gαq is uncoupled from RGS proteins, which method comprises evaluating the phenotype of the transgenic rat of claim 1 to which a test compound is administered, wherein a change in phenotype relative to a control transgenic rat to which the compound is not administered indicates the effect of the compound in an animal in which Gαq is uncoupled from RGS proteins.

15. The method according to claim 14, wherein the compound is a 5-HT2C agonist and the phenotype is inhibition of food intake.

16. The method according to claim 14, wherein the compound is a 5-HT2A agonist and the phenotype is increased sensitivity to 5-HT2A agonists, wherein said increased sensitivity is manifested by an effect selected from the group consisting of induction of headshakes, flattened body posture, convulsions, and death.

17. The method according to claim 14, wherein the compound is a muscarinic agonist and the phenotype is manifested by an effect selected from the group consisting of increase in cholinergic signs, convulsions, and death.

18. The method according to claim 14, wherein the compound is an NMDA antagonist and the phenotype is an increase in hyperactivity.

19. The method according to claim 14, wherein the compound is a DA agonist and the phenotype is a decrease in hyperactivity.

20. A method for generating a transgenic rat of claim 1 that has extended GPCR signaling, which method comprises introducing a nucleotide sequence encoding a mutant Gαq subunit protein that has glycine 188 substituted with serine (G188S) into the genome of the rat, said nucleotide sequence being operatively linked with a neuron-specific expression control sequence, whereby the transgenic rat expresses the Gαq subunit protein in neural cells resulting in extended GPCR signaling.

21. The method of claim 20, wherein the G188S mutation in the mutant Gαq subunit protein is a dominant negative mutation.

22. The method of claim 20, wherein the mutant Gαq subunit protein is mouse Gαq.

23. The transgenic rat of claim 4, wherein the neuron-specific expression control sequence comprises a Thy 1.2 promoter.

24. A method for identifying the effect of a compound on an animal in which Gαq is uncoupled from RGS proteins, which method comprises evaluating the phenotype of the transgenic rat of claim 4 to which a test compound is administered, wherein a change in phenotype relative to a control transgenic rat to which the compound is not administered indicates the effect of the compound in an animal in which Gαq is uncoupled from RGS proteins.

* * * * *